US012599381B2

(12) United States Patent (10) Patent No.: US 12,599,381 B2
Satti, III et al. (45) Date of Patent: Apr. 14, 2026

(54) SURGICAL STAPLER WITH REMOVABLE POWER PACK

(71) Applicant: RevMedica, Inc., Middletown, CT (US)

(72) Inventors: C. Robert Satti, III, Westbrook, CT (US); Thomas G. Wenchell, Jr., Durham, CT (US); Peter Nielsen, Ridgefield, CT (US)

(73) Assignee: RevMedica, Inc., Middletown, CT (US)

( * ) Notice: Subject to any disclaimer, the term of this patent is extended or adjusted under 35 U.S.C. 154(b) by 0 days.

(21) Appl. No.: 18/935,845

(22) Filed: Nov. 4, 2024

(65) Prior Publication Data

US 2025/0127509 A1 Apr. 24, 2025

Related U.S. Application Data

(63) Continuation of application No. 18/222,548, filed on Jul. 17, 2023, now Pat. No. 12,213,669, which is a
(Continued)

(51) Int. Cl.
*A61B 17/072* (2006.01)
*A61B 17/068* (2006.01)
(Continued)

(52) U.S. Cl.
CPC .......... *A61B 17/072* (2013.01); *A61B 17/068* (2013.01); *A61B 2017/00017* (2013.01);
(Continued)

(58) Field of Classification Search
CPC ............ A61B 17/0644; A61B 17/0682; A61B 17/068; A61B 17/072; A61B 17/07207;
(Continued)

(56) References Cited

U.S. PATENT DOCUMENTS 4,940,061 A 7/1990 Terwilliger et al.
5,129,570 A 7/1992 Schulze et al.
(Continued)

FOREIGN PATENT DOCUMENTS

JP 2000-071116 3/2000
WO WO 2024/201198 10/2024

OTHER PUBLICATIONS

EP 22 76 3759 European Search Report & Written Opinion dated: Jan. 2, 2025.
PCT/US2024/016128 International Search Report (Jul. 3, 2024).

*Primary Examiner* — Joshua G Kotis
(74) *Attorney, Agent, or Firm* — Neil D. Gershon

(57) ABSTRACT

A surgical fastener applier having a housing containing a compartment therein, an elongated member extending distally from the housing and first and second jaws. A firing mechanism is positioned within the housing movable to a second position to effect firing of fasteners. A power pack is removably loadable into the compartment, the power pack having one or both of a) a first motor and a first engagement member removably engageable with the firing mechanism when the power pack is loaded into the compartment to effect movement of the firing mechanism; and b) a second motor and a second engagement member removably engageable with an articulating mechanism in the housing of the surgical fastener applier to effect movement of an articulation mechanism to effect articulation. One or both of a firing position and an articulation position are tracked during the surgical procedure. Sensors are provided to detect select parameters and instrument functions.

19 Claims, 69 Drawing Sheets

Related U.S. Application Data continuation of application No. 18/078,308, filed on Dec. 9, 2022, now Pat. No. 12,167,850, which is a continuation of application No. 17/269,907, filed as application No. PCT/US2020/042033 on Jul. 15, 2020, now Pat. No. 11,564,685.

(60) Provisional application No. 62/962,388, filed on Jan. 17, 2020, provisional application No. 62/876,586, filed on Jul. 19, 2019.

(51) Int. Cl.

| | |
|---|---|
| *A61B 17/29* | (2006.01) |
| *A61B 17/00* | (2006.01) |
| *A61B 17/115* | (2006.01) |
| *A61B 17/32* | (2006.01) |
| *A61B 34/20* | (2016.01) |
| *A61B 34/30* | (2016.01) |
| *A61B 90/00* | (2016.01) |

(52) U.S. Cl.
CPC .............. *A61B 2017/00022* (2013.01); *A61B 2017/00398* (2013.01); *A61B 2017/00473* (2013.01); *A61B 2017/00734* (2013.01); *A61B 17/07207* (2013.01); *A61B 2017/07214* (2013.01); *A61B 2017/07257* (2013.01); *A61B 2017/07271* (2013.01); *A61B 17/1155* (2013.01); *A61B 2017/2927* (2013.01); *A61B 2017/320052* (2013.01); *A61B 2034/2059* (2016.02); *A61B 34/30* (2016.02); *A61B 2090/0807* (2016.02); *A61B 2090/0811* (2016.02)

(58) Field of Classification Search
CPC .............. A61B 17/115; A61B 17/1155; A61B 17/2909; A61B 17/00234; A61B 2017/00017; A61B 2017/00022; A61B 2017/00473; A61B 2017/00477; A61B 2017/320052; A61B 2017/07214; A61B 2017/07278; A61B 2017/2927; A61B 2017/2929; A61B 34/20; A61B 34/30; A61B 34/71; A61B 34/76; A61B 2090/0807; A61B 2090/0808; A61B 2090/0811
USPC .............. 227/19, 175.1, 175.2, 176.1, 180.1; 606/1, 139, 219
See application file for complete search history.

(56) References Cited

U.S. PATENT DOCUMENTS

| | | | |
|---|---|---|---|
| 5,383,880 | A | 1/1995 | Hooven |
| 5,704,534 | A | 1/1998 | Huitema et al. |
| 5,878,938 | A | 3/1999 | Bittner et al. |
| 8,011,555 | B2 | 9/2011 | Tarinelli et al. |
| 8,414,577 | B2 | 4/2013 | Boudreaux et al. |
| 9,011,471 | B2 | 4/2015 | Timm et al. |
| 9,078,653 | B2 | 7/2015 | Leimbach et al. |
| 9,265,501 | B2 | 2/2016 | Tiwari |
| 9,717,498 | B2 | 8/2017 | Aranyi et al. |
| 9,782,214 | B2 | 10/2017 | Houser et al. |
| 10,154,841 | B2 | 12/2018 | Weaner et al. |
| 10,278,702 | B2 | 5/2019 | Shelton, IV et al. |
| 10,456,140 | B2 | 10/2019 | Shelton, IV et al. |
| 10,478,190 | B2 | 11/2019 | Miller et al. |

| | | | | |
|---|---|---|---|---|
| 10,492,785 | B2 | 12/2019 | Overmyer et al. | |
| 10,639,034 | B2 | 5/2020 | Harris et al. | |
| 10,835,247 | B2 | 11/2020 | Shelton, IV et al. | |
| 10,874,393 | B2 | 12/2020 | Satti, III et al. | |
| 10,881,401 | B2 | 1/2021 | Baber et al. | |
| 10,980,536 | B2 | 4/2021 | Weaner et al. | |
| 11,096,689 | B2 | 8/2021 | Overmyer et al. | |
| 11,116,485 | B2 | 9/2021 | Scheib et al. | |
| 11,166,716 | B2 | 11/2021 | Shelton, IV et al. | |
| 11,191,543 | B2 | 12/2021 | Overmyer et al. | |
| 11,197,668 | B2 | 12/2021 | Shelton, IV et al. | |
| 11,229,433 | B2 | 1/2022 | Schings et al. | |
| 11,234,698 | B2 | 2/2022 | Shelton, IV et al. | |
| 11,311,293 | B2 | 4/2022 | Roberts et al. | |
| 11,389,143 | B2 | 7/2022 | Ranucci et al. | |
| 11,406,382 | B2 | 8/2022 | Shelton, IV et al. | |
| 11,439,390 | B2 | 9/2022 | Patel et al. | |
| 11,452,524 | B2 | 9/2022 | Chavan et al. | |
| 11,517,312 | B2 | 12/2022 | Wixey | |
| 11,523,825 | B2 | 12/2022 | Becerra et al. | |
| 11,564,685 | B2 * | 1/2023 | Satti, III | ........... A61B 17/2909 |
| 11,666,330 | B2 | 6/2023 | Whitfield et al. | |
| 11,751,871 | B2 | 9/2023 | Roberts et al. | |
| 11,896,223 | B2 | 2/2024 | Baxter, III et al. | |
| 11,903,601 | B2 * | 2/2024 | Shelton, IV | ........... A61B 34/76 |
| 11,937,812 | B2 | 3/2024 | Schings et al. | |
| 11,998,201 | B2 | 6/2024 | Huang et al. | |
| 12,004,745 | B2 | 6/2024 | Shelton, IV et al. | |
| 12,035,909 | B2 | 7/2024 | Fernandes et al. | |
| 12,167,850 | B2 * | 12/2024 | Satti, III | ........... A61B 17/2909 |
| 12,213,669 | B2 * | 2/2025 | Satti, III | .............. A61B 17/068 |
| 2007/0023477 | A1 * | 2/2007 | Whitman | ......... A61B 17/07207 |
| | | | | 227/175.1 |
| 2007/0175950 | A1 * | 8/2007 | Shelton | ........... A61B 17/07207 |
| | | | | 227/176.1 |
| 2008/0255413 | A1 * | 10/2008 | Zemlok | .............. A61B 17/1155 |
| | | | | 600/106 |
| 2011/0022032 | A1 * | 1/2011 | Zemlok | ........... A61B 17/07207 |
| | | | | 606/1 |
| 2014/0249557 | A1 * | 9/2014 | Koch, Jr. | ............... A61B 90/98 |
| | | | | 606/170 |
| 2015/0230793 | A1 * | 8/2015 | Kostrzewski | ...... A61B 17/0644 |
| | | | | 227/176.1 |
| 2015/0316431 | A1 | 11/2015 | Collins et al. | |
| 2015/0374360 | A1 | 12/2015 | Scheib et al. | |
| 2016/0066916 | A1 * | 3/2016 | Overmyer | ............ G06F 1/3287 |
| | | | | 227/176.1 |
| 2016/0367245 | A1 | 12/2016 | Wise et al. | |
| 2017/0189020 | A1 * | 7/2017 | Harris | .................. A61B 17/072 |
| 2017/0296173 | A1 * | 10/2017 | Shelton, IV | ........... H02J 7/007 |
| 2018/0168608 | A1 | 6/2018 | Shelton, IV et al. | |
| 2019/0290274 | A1 | 9/2019 | Shelton, IV | |
| 2019/0293828 | A1 | 9/2019 | Calderoni et al. | |
| 2020/0315726 | A1 | 10/2020 | Zemlok et al. | |
| 2020/0405406 | A1 | 12/2020 | Harris et al. | |
| 2021/0169487 | A1 | 6/2021 | Nicholas et al. | |
| 2022/0031312 | A1 * | 2/2022 | George | .............. A61B 17/0686 |
| 2022/0054130 | A1 | 2/2022 | Overmyer et al. | |
| 2022/0249096 | A1 | 8/2022 | Son et al. | |
| 2022/0378418 | A1 | 12/2022 | Huang et al. | |
| 2023/0149016 | A1 | 5/2023 | Williams et al. | |
| 2023/0248360 | A1 | 8/2023 | Shelton, IV et al. | |
| 2023/0255626 | A1 | 8/2023 | Marecki et al. | |
| 2023/0338021 | A1 | 10/2023 | Zhang | |
| 2023/0338027 | A1 | 10/2023 | Schings et al. | |
| 2024/0032914 | A1 * | 2/2024 | Satti, III | ........... A61B 17/2909 |
| 2024/0074749 | A1 | 3/2024 | Schings et al. | |
| 2024/0148376 | A1 | 5/2024 | Williams | |
| 2024/0164771 | A1 * | 5/2024 | Wenchell, Jr. | ....... A61B 17/072 |
| 2024/0350140 | A1 | 10/2024 | Leimbach et al. | |

* cited by examiner

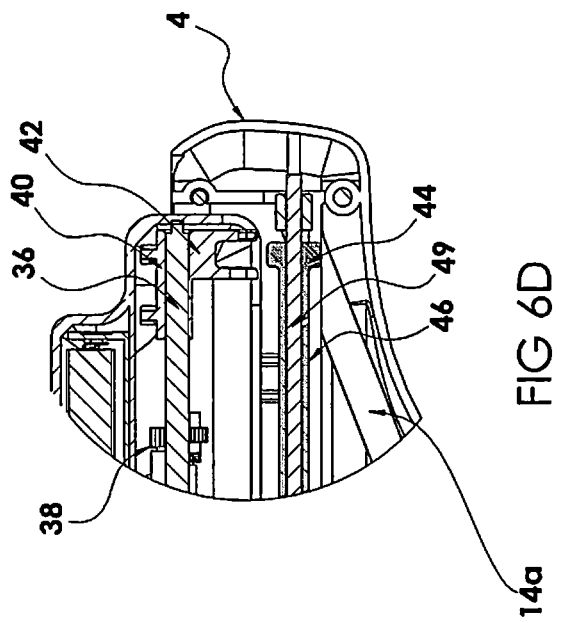
FIG 6D
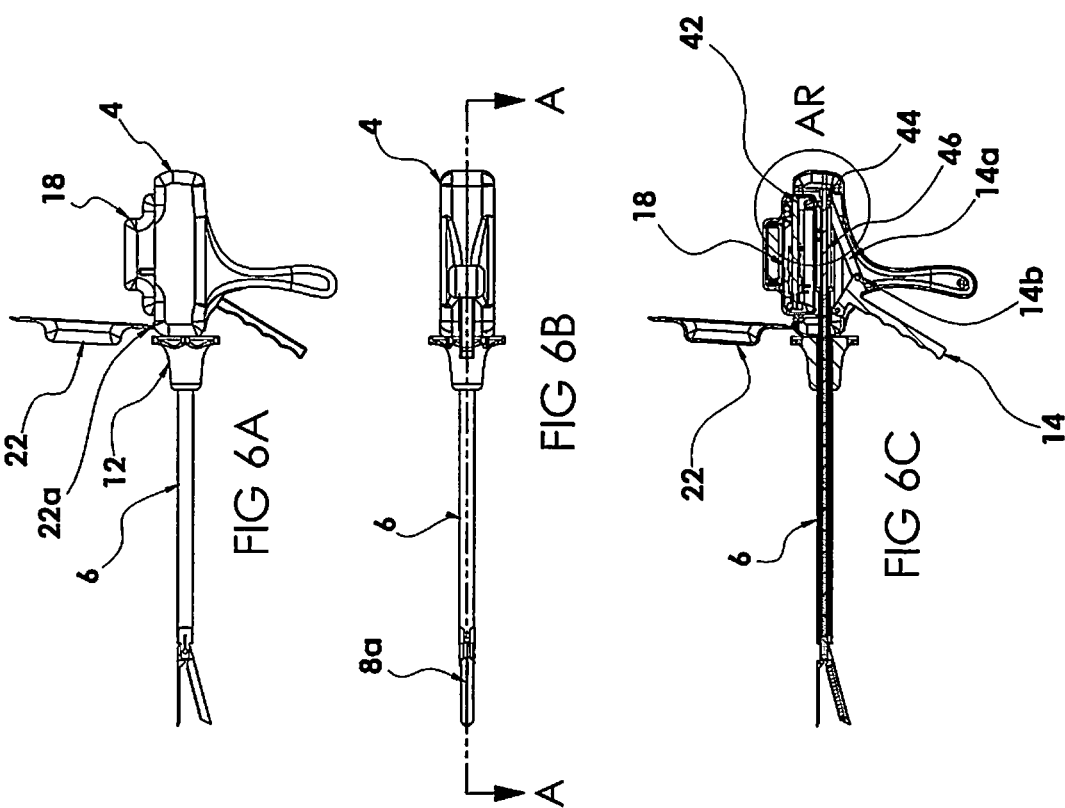
FIG 6A
FIG 6B
FIG 6C

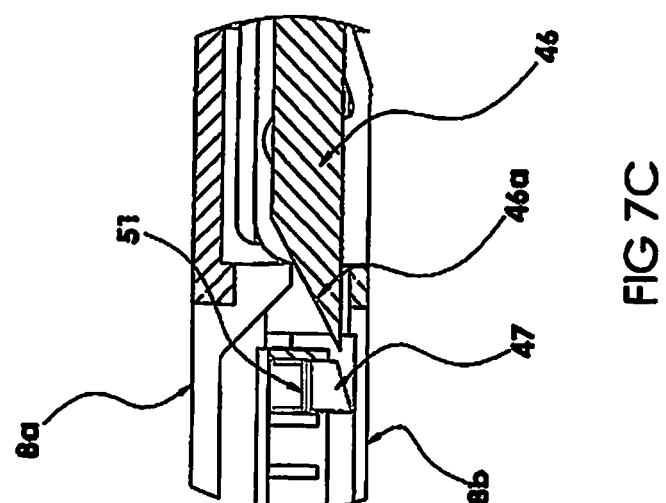
FIG 7C
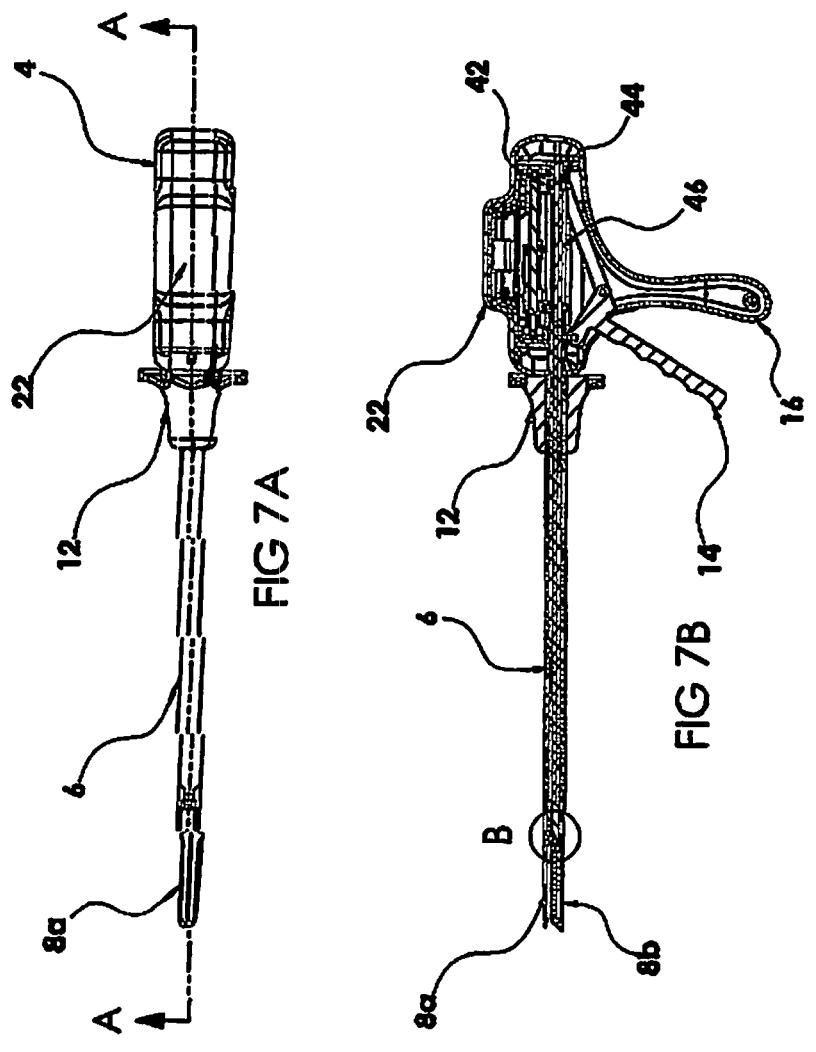
FIG 7A
FIG 7B

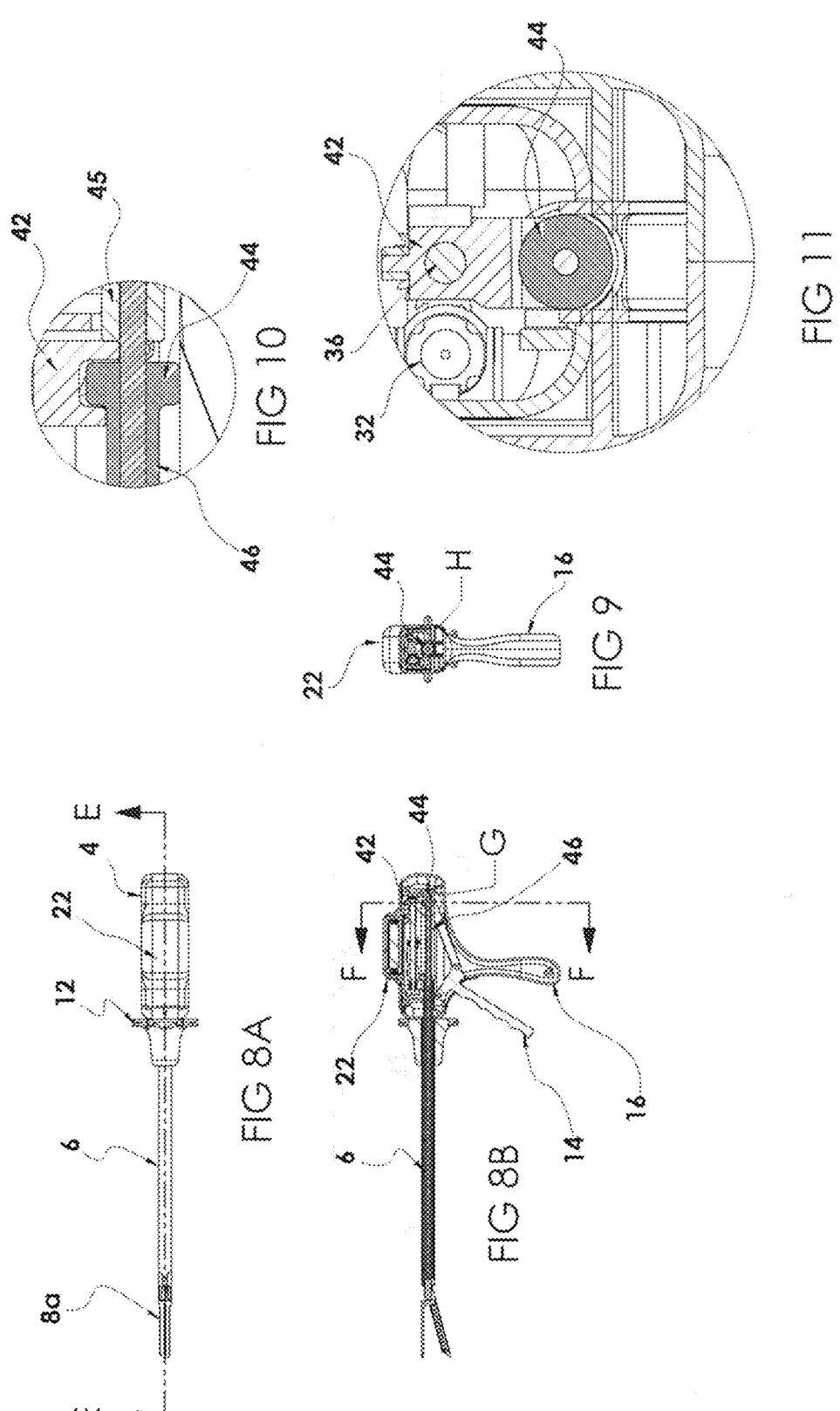

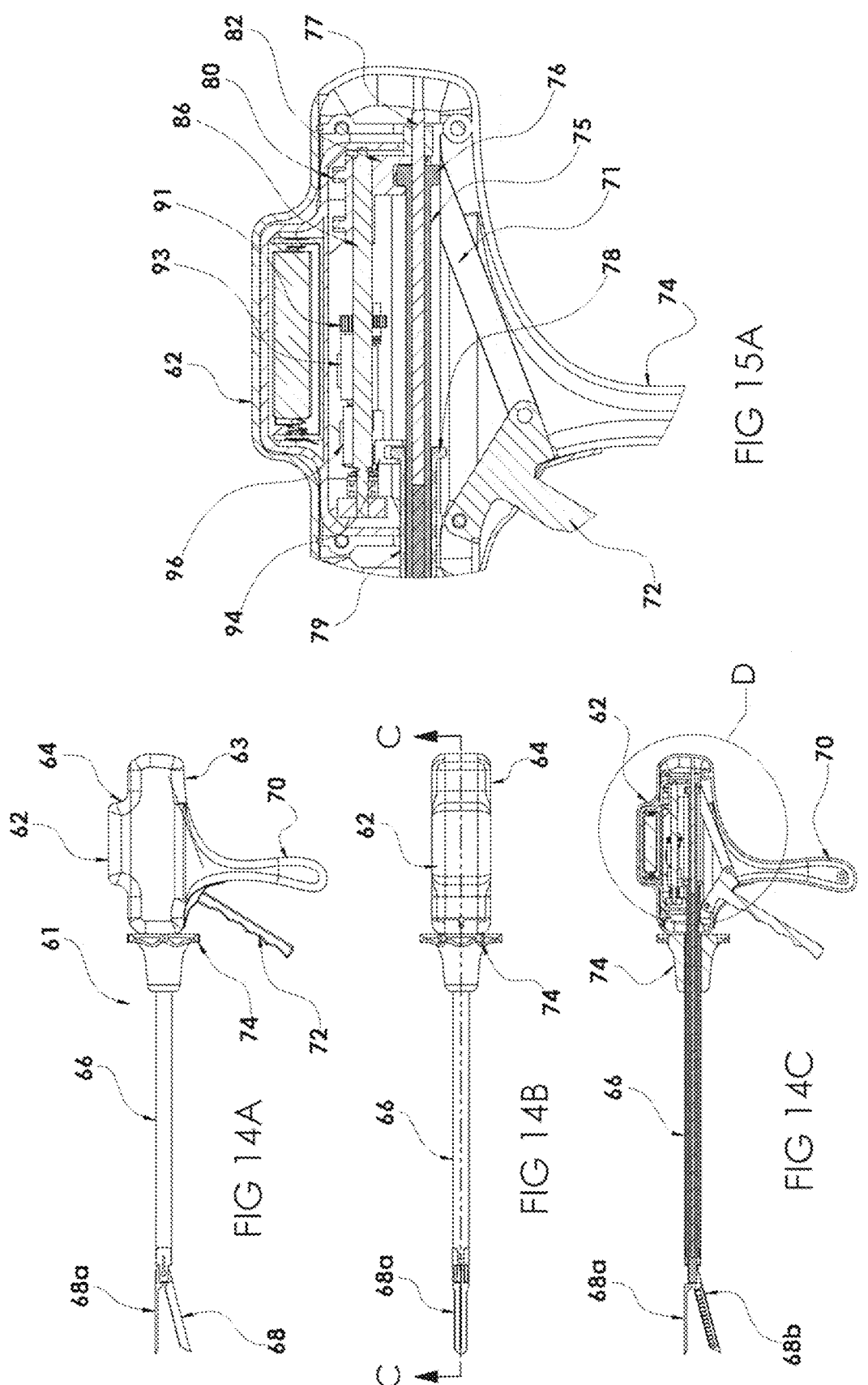

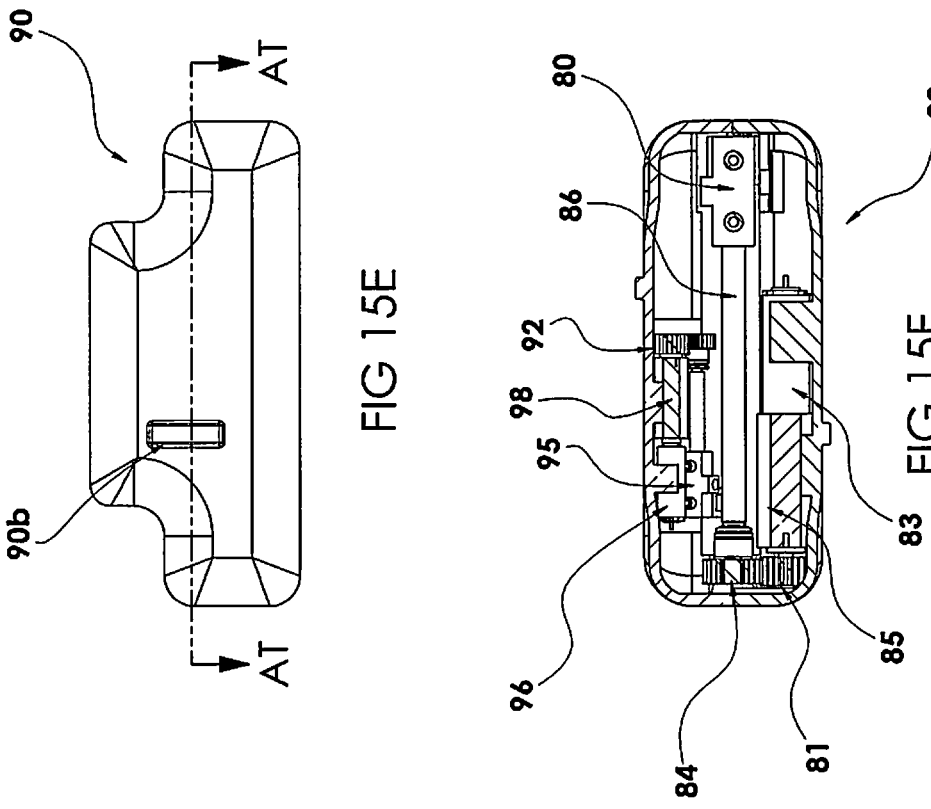
FIG 15E
FIG 15F
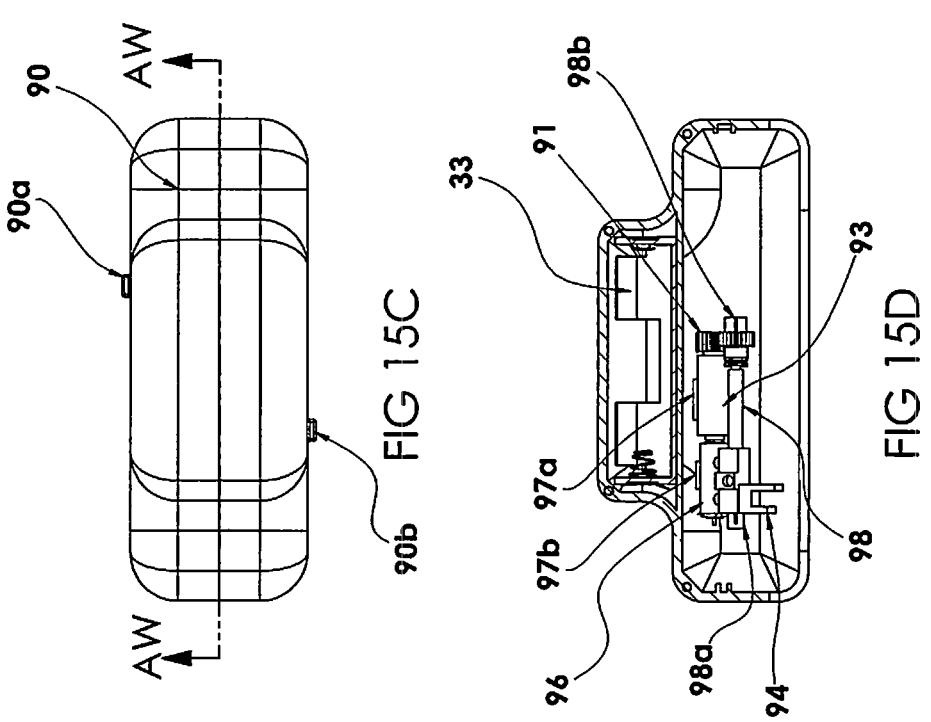
FIG 15C
FIG 15D

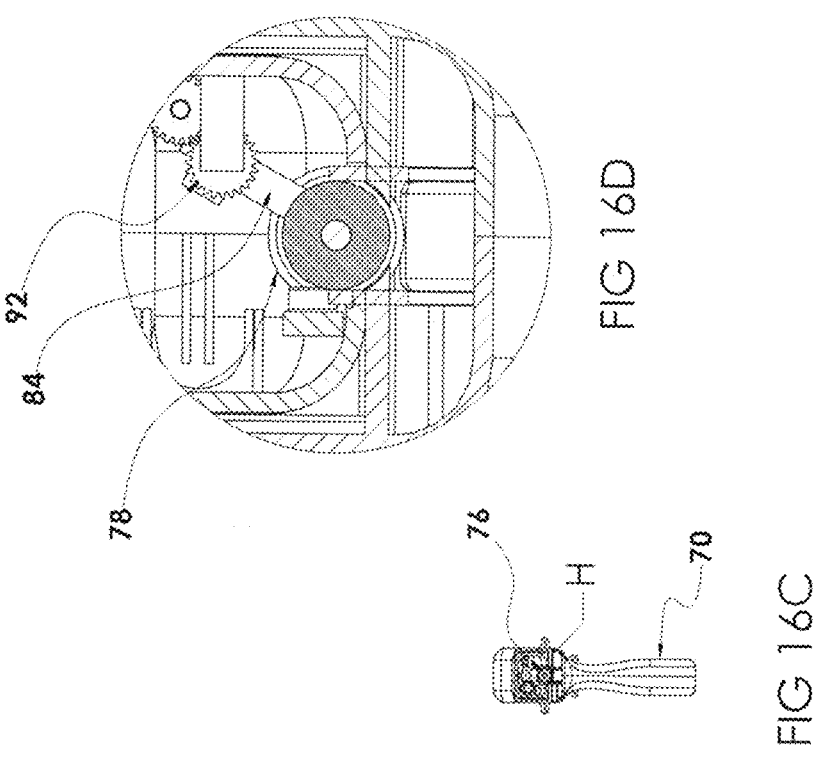
FIG 16D
FIG 16C
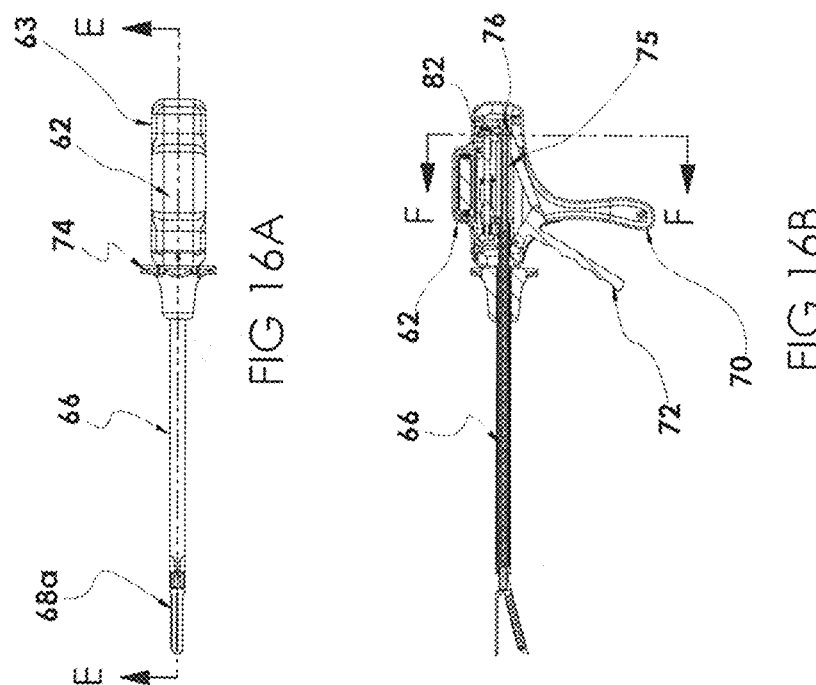
FIG 16A
FIG 16B

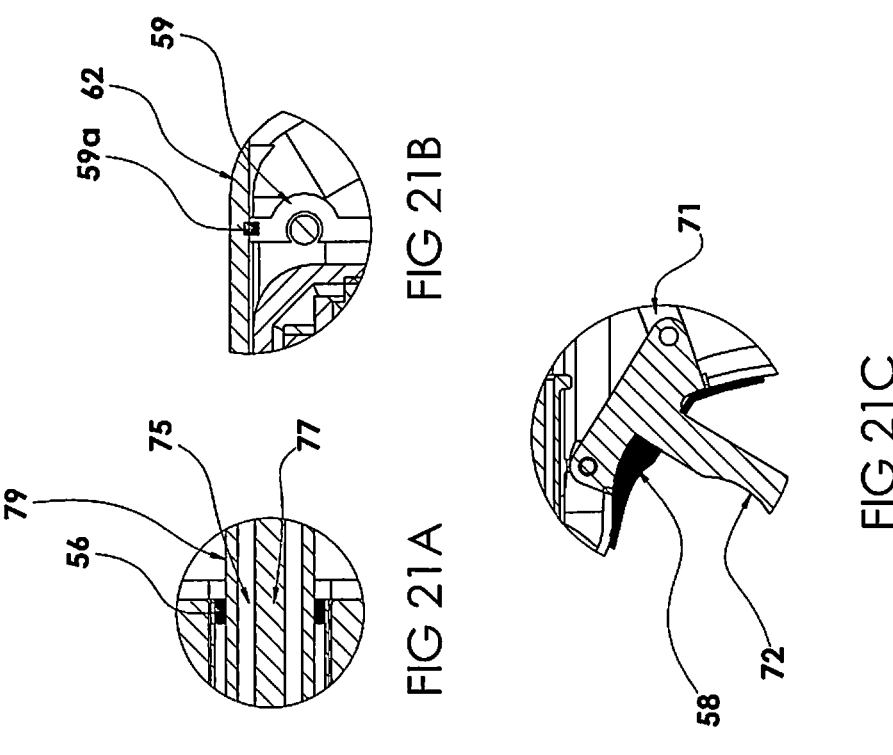
FIG 21B
FIG 21A
FIG 21C
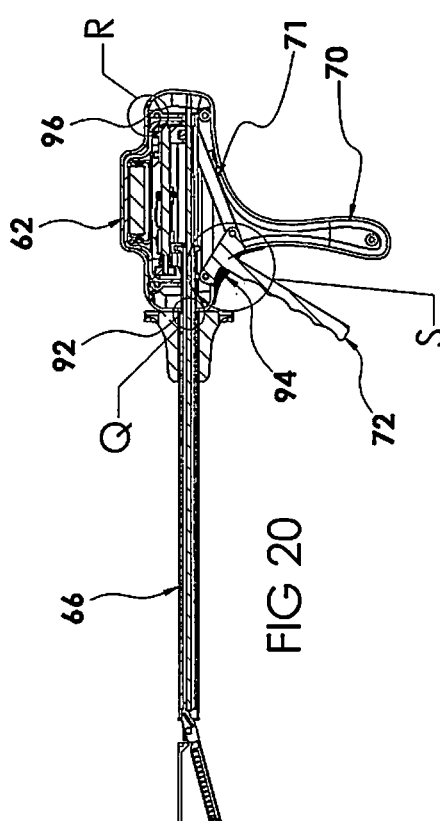
FIG 20

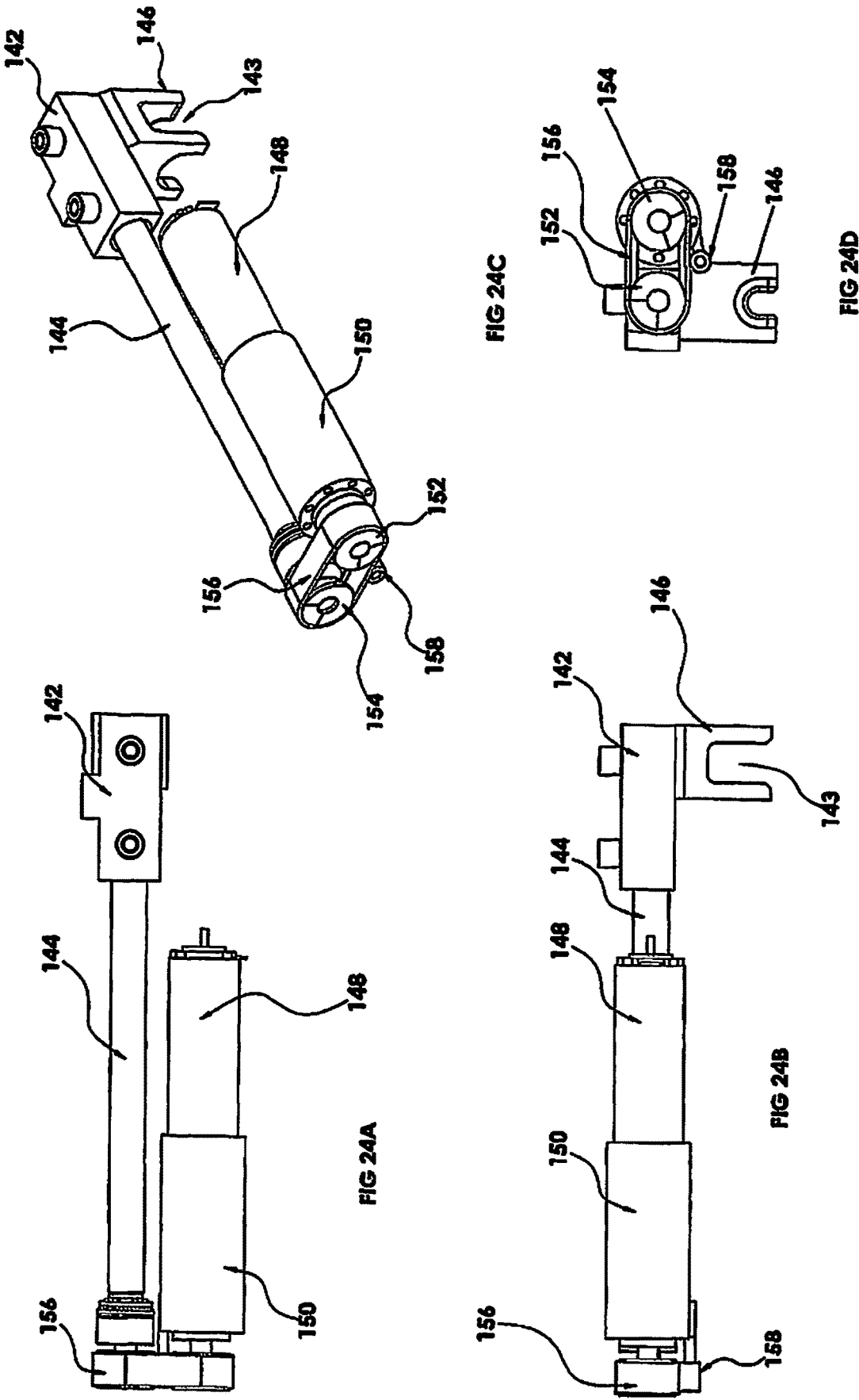

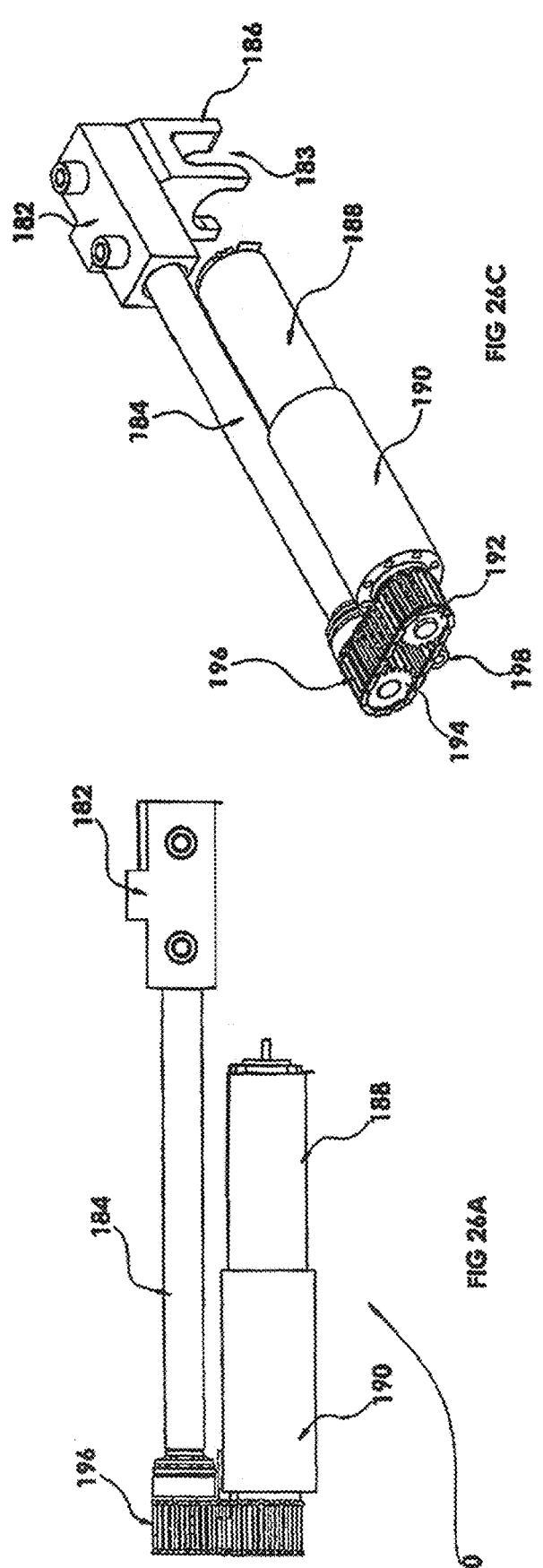
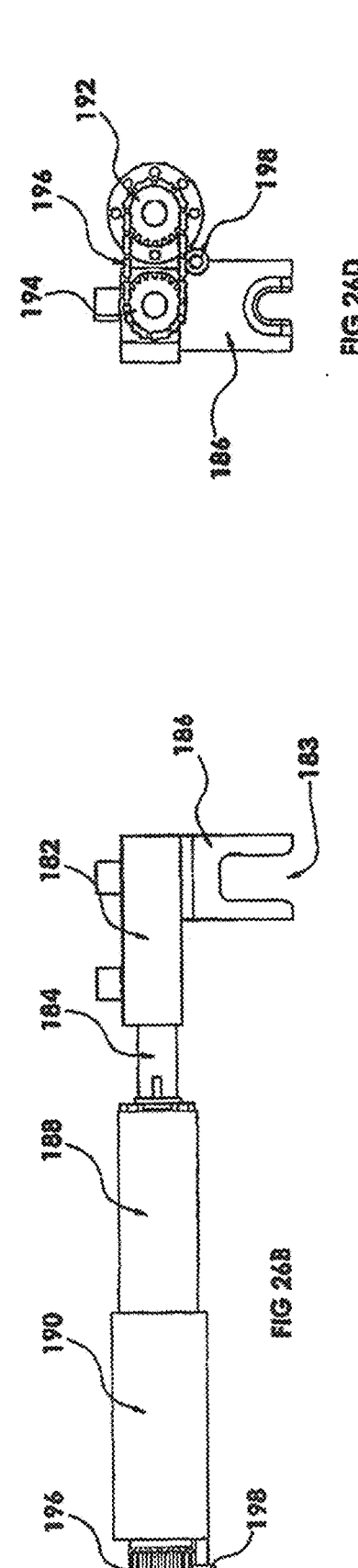

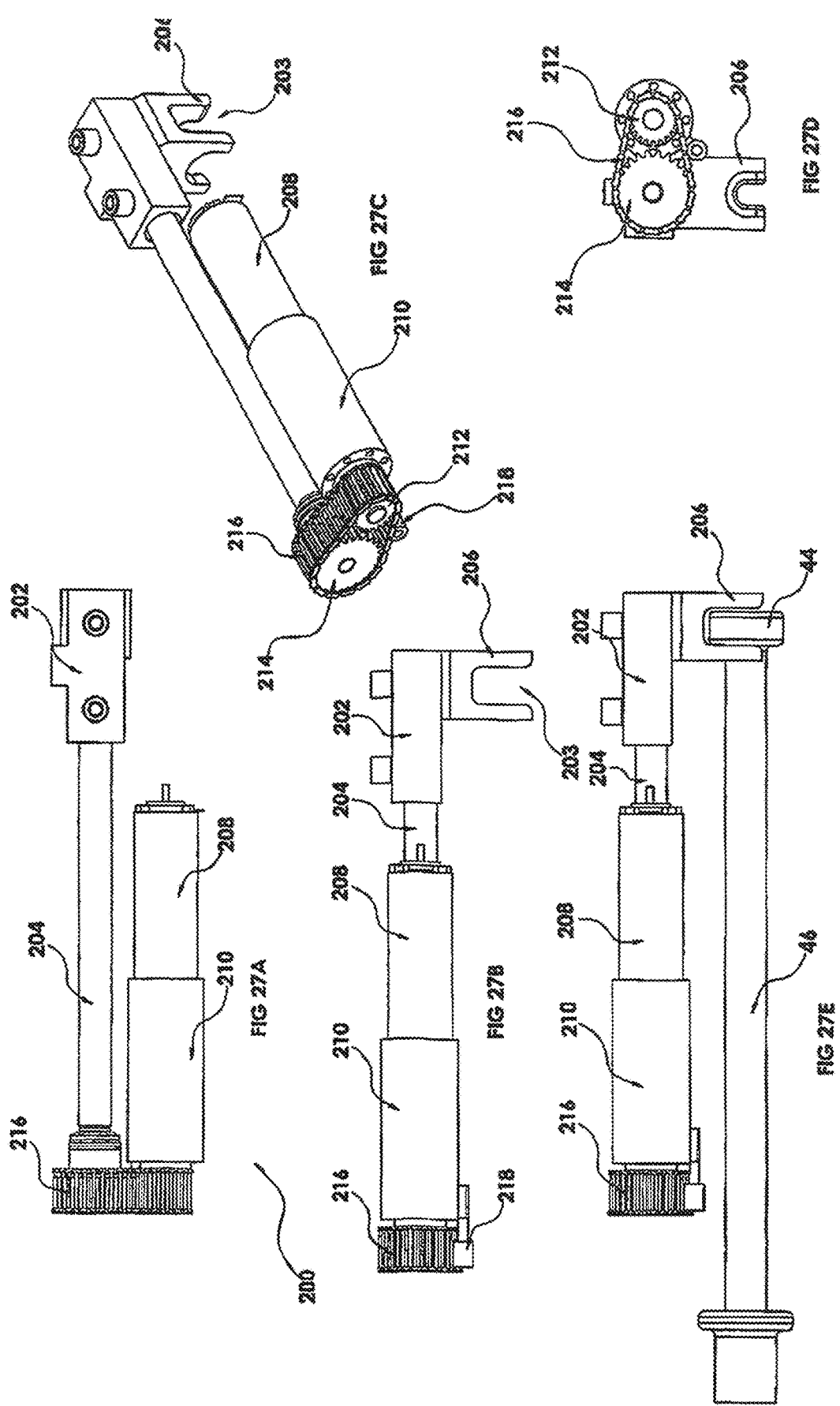

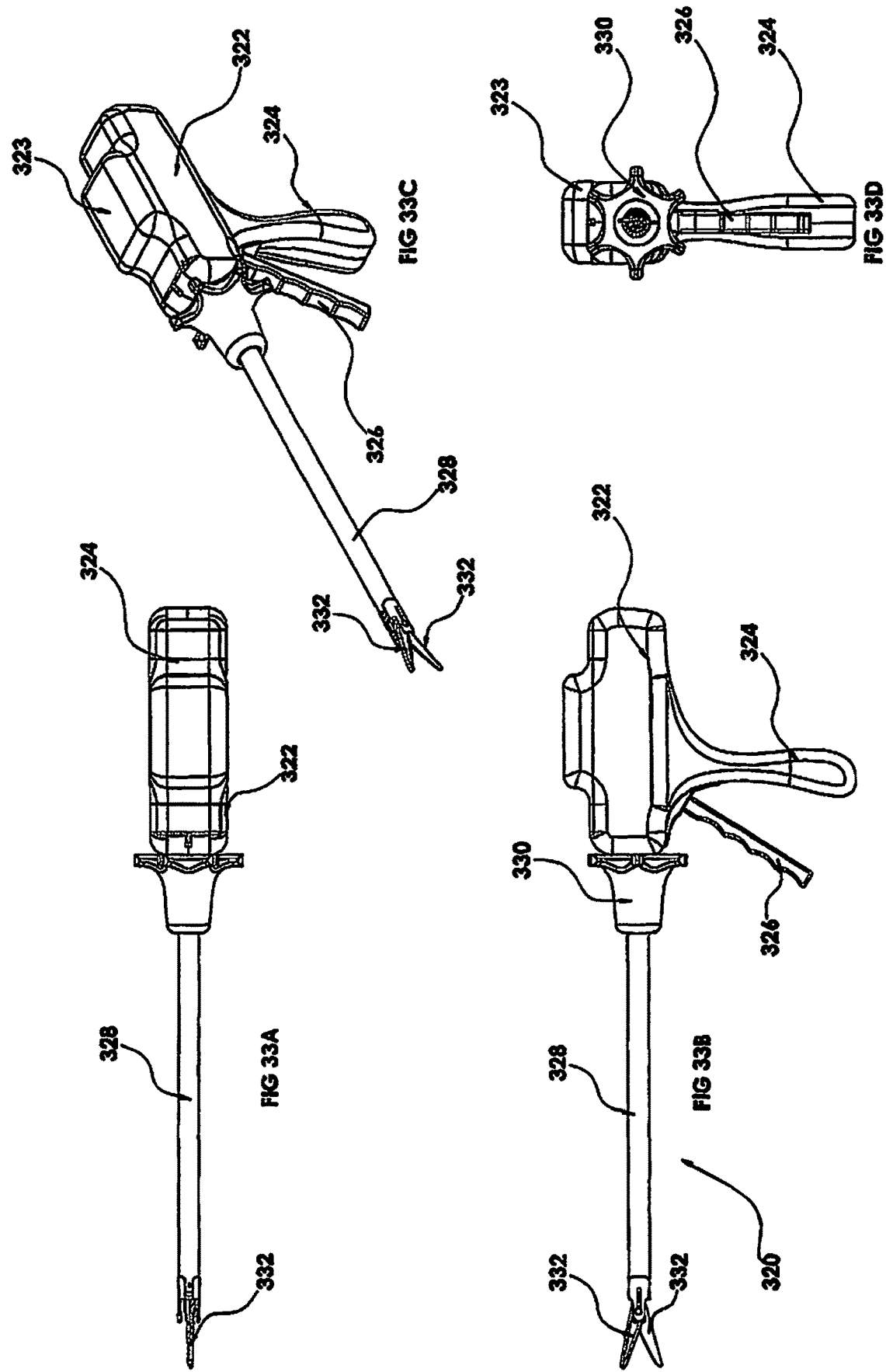

DETAIL CB
SCALE 2:1

SURGICAL STAPLER WITH REMOVABLE POWER PACK

This application is a continuation of application Ser. No. 18/222,548, filed Jul. 17, 2023, which is a continuation of application Ser. No. 18/078,308, filed Dec. 9, 2022, which is a continuation of application Ser. No. 17/269,907, filed Feb. 19, 2021, now U.S. Pat. No. 11,564,685, which is a 371 of PCT application PCT/US2020/042033, filed Jul. 15, 2020, which claims priority from provisional application Ser. No. 62/962,388, filed Jan. 17, 2020 and from provisional application Ser. No. 62/876,586, filed Jul. 19, 2019. The entire contents of each of these applications are incorporated herein by reference.

BACKGROUND OF THE INVENTION

1. Field of the Invention

This application relates to surgical staplers and removable power packs loadable into the surgical staplers to effect firing of the staples.

2. Background

Surgical staplers are used in various medical applications where a device is needed to join and dissect anatomical tissue. However, there are drawbacks and costs associated with use of surgical staplers. Currently staplers are either fully disposable, reusable or partially reusable. Due to contamination during the surgical procedure, e.g., exposure to the patient's body fluids, the staplers are required to be sterilized after use, a time consuming and expensive process, with possible risks of infection if not properly sterilized as contaminants adhered to the surgical stapler from a previous use could be transferred to another patient. To avoid the risks of resterilization, some surgical staplers are disposed after use in the surgical procedure. These staplers can be reloaded to fire multiple cartridges of staples, but after the procedure, the staplers are discarded. However, the practice of using single use disposable surgical staplers is costly.

In certain procedures, high forces are required to fire the staples through tissue into contact with the anvil for formation. This is compounded when multiple rows of staples are fired either simultaneously or sequentially from the stapler. Therefore, powered staplers have been introduced to reduce the force requirements of the user. Such powered staplers have motor driven mechanisms (assemblies) to advance components within the stapler to fire the staples from the cartridge through tissue. Such powered staplers, if reusable, are subject to the same aforementioned costs and risk of resterilization. However they suffer from additional drawbacks since the sterilization process and/or heat or chemicals used in the sterilization process can damage the electronic components of the drive assemblies, which may shorten the lifespan of the surgical stapler or adversely affect its function if resterilization compromises the function of the motor or drive assembly. If the stapler is disposable, the stapler becomes more costly since the electronic components, which add to the cost of the stapler, are also discarded with the stapler.

It would be advantageous to provide a cost effective, efficient, simple to use and advanced assemblies for powering surgical instruments which overcome the drawbacks of manual actuation without suffering from the disadvantages of current power driven staplers.

Further, it would be advantageous to provide such surgical instruments which include systems to evaluate various parameters and functionalities to improve operation of the instruments and improve the surgical procedures and outcomes.

SUMMARY

The present invention overcomes the deficiencies and disadvantages of the prior art. The present invention advantageously provides surgical staplers that overcome the drawbacks discussed above by having a fully enclosed and removable power pack. The surgical staplers according to the present disclosure may be used multiple times without the need to sterilize the power pack between uses because the power pack is fully enclosed and sealed by the surgical stapler handle assembly or housing, thereby preventing contact between the power pack and the patient and/or patient's bodily fluids or the like. Thus, the surgical staplers of the present disclosure advantageously reduce the time, resources and/or costs for preparing the surgical stapler for its next use. The present disclosure also provides power packs that are cost effective, efficient and easily loadable into surgical staplers where they engage structure in the housing to effect varied functions of the stapler.

In accordance with one aspect of the present invention, a power pack removably loadable into a compartment of a surgical fastener applier is provided. The power pack has a) a first motor and b) a first drive mechanism having a first engagement member, the first drive mechanism operably connected to the motor and the first engagement member removably engageable with a firing mechanism of the surgical fastener applier when the power pack is loaded into the compartment to effect movement of the firing mechanism from a first position to the second position. A rotatable screw is rotatable by the motor to effect linear movement of the first engagement member and an encoder is positioned within the power pack to detect movement of the rotatable screw to determine a firing position of the firing mechanism.

In some embodiments, the encoder is mounted to the rotatable screw to detect a rotational position of the screw to determine the axial position of the first engagement member which in turn detects the axial position of the firing mechanism of the surgical stapler, the encoder rotatable with rotation of the rotatable screw and rotatable relative to a code wheel fixedly mounted within the power pack.

In other embodiments, the encoder is connected to the first drive mechanism and moves linearly with linear movement of the first drive mechanism to detect a linear position of the first drive mechanism to thereby detect a position of the firing mechanism. The encoder can be mounted to a collar of the first drive mechanism, the collar including a region forming the first engagement member.

In some embodiments, the power pack includes a second motor, a second rotatable screw operatively connected to and rotatable by the second motor and a second drive mechanism operatively connected to the second rotatable screw and having a second engagement member removably engageable with an articulating mechanism in the housing of the surgical fastener applier to effect movement of the articulation mechanism to effect articulation of first and second jaws of the surgical stapler from a linear position to an angled position. A second encoder is positioned within the power pack to detect movement of the second rotatable screw to determine an articulation position of the articulation mechanism.

In accordance with another aspect of the present invention, a surgical fastener applier is provided comprising a housing containing a compartment therein, an elongated member extending distally from the housing, and a first jaw and a second jaw at a distal portion of the elongated member, at least the first jaw movable with respect to the second jaw to clamp tissue between the first and second jaws. A firing mechanism is positioned within the housing, the firing mechanism movable between a first position and a second position, wherein movement to the second position effects firing of fasteners into the tissue clamped between the first and second jaws. A power pack is removably loadable into the compartment, the power pack having a) a first motor and a first engagement member removably engageable with the firing mechanism when the power pack is loaded into the compartment to effect movement of the firing mechanism from the first position to the second position; and b) a second motor and a second engagement member removably engageable with an articulating mechanism in the housing of the surgical fastener applier to effect movement of an articulation mechanism to effect articulation of the first and second jaws from a linear position to a position angled with respect to a longitudinal axis of the elongated member. A firing position is determined based on a first motor count of the first motor and an articulation position is determined based on a second motor count of the second motor.

In some embodiments, an encoder communicates the motor counts to a microprocessor within the power pack for adjustment of a motor speed. In some embodiments, a predetermined time for completion of a firing stroke of the firing mechanism is preset. In some embodiments, if an amperage of the first motor increases above a predetermined threshold, a speed of the motor is slowed and the present time is adjusted accordingly.

In accordance with another aspect of the present invention, a power pack removably loadable into a compartment of a surgical fastener applier is provided. The power pack has a first motor and a first engagement member removably engageable with a firing mechanism within the housing of the surgical fastener applier when the power pack is loaded into the compartment, the first engagement member movable axially in response to rotation of a first screw operatively connected to the first motor. At least one thrust bearing limits axial movement of the first screw. Linear movement of the first engagement member effects movement of the firing mechanism from the first position to the second position. A first load cell is engageable by the bearing to measure a force during firing.

In some embodiments, the power pack includes a second motor and a second engagement member removably engageable with an articulation mechanism within the housing when the power pack is loaded into the compartment, the second engagement member movable axially in response to rotation of a second screw operatively connected to the second motor, wherein linear movement of the second engagement member effects movement of the articulation mechanism to effect articulation of the first and second jaws and at least one bearing limits axial movement of the second screw. A second load cell is engageable by the bearing to measure an articulation force.

In accordance with another aspect of the present invention, a surgical fastener applier is provided comprising:

a housing containing a compartment therein, the compartment having an openable cover to provide access to the compartment for removably loading a power pack having a motor;

an elongated member extending distally from the housing;

a first jaw and a second jaw adjacent a distal portion of the elongated member, at least the first jaw movable with respect to the second jaw to clamp tissue between the first and second jaws; and a fastener firing mechanism positioned within the housing, the firing mechanism movable by the motor of the power pack loaded into the compartment, the firing mechanism movable between a first position and a second position, wherein in the second position, the firing mechanism effects firing of fasteners into the tissue clamped between the first and second jaws;

wherein the motor of the power pack received in the compartment is not actuable unless the cover is closed.

In some embodiments, the cover includes a member movable into contact with an activation switch in the power pack when the cover is closed. In some embodiments, the power pack has a printed circuit board in communication with the switch.

In accordance with another aspect of the present invention, a surgical fastener applier is provided comprising:

a housing containing a compartment therein, the compartment having an openable cover to provide access to the compartment for removably loading a power pack having a motor;

an elongated member extending distally from the housing;

a first jaw and a second jaw adjacent a distal portion of the elongated member, at least the first jaw movable with respect to the second jaw to clamp tissue between the first and second jaws;

a fastener firing mechanism positioned within the housing, the firing mechanism movable by the motor of the power pack loaded into the compartment, the firing mechanism movable between a first position and a second position, wherein in the second position, the firing mechanism effects firing of fasteners into the tissue clamped between the first and second jaws; and a power pack having an reader, such as an RFID reader, for detecting a type of staple cartridge prior to loading the staple cartridge in the instrument, the staple cartridge having an a code or tag, such as an RFID tag.

In some embodiments, the power pack presets the motor to correspond to the type of staple cartridge detected. The type of staple cartridge detected can be a length of a linear array of staples within the cartridge and/or a size of the staples within the cartridge.

In some embodiments, a motor in the power pack for firing staples cannot be actuated if the reader detects the staple cartridge has already been fired.

In some embodiments, the surgical fastener applier has a window adjacent the housing exhibiting a desired clamp force dependent on the type of cartridge and/or the type of cartridge selected.

In accordance with another aspect of the present invention, a surgical fastener applier is provided comprising:

a housing containing a compartment therein, the compartment having an openable cover to provide access to the compartment for removably loading a power pack having a motor, a first switch and a second switch;

an elongated member extending distally from the housing;

a first jaw and a second jaw adjacent a distal portion of the elongated member, at least the first jaw movable with respect to the second jaw to clamp tissue between the first and second jaws;

a fastener firing mechanism positioned within the housing, the firing mechanism movable by the first motor of the power pack loaded into the compartment, the firing mechanism movable between a first position and a second position, wherein in the second position, the firing mechanism effects firing of fasteners into the tissue clamped between the first and second jaws, the firing mechanism actuated by the first switch; and an articulation mechanism movable between a first position to a second position to angle the first and second jaws to an angled position with respect to a longitudinal axis of the elongated member, the articulation mechanism actuated by a second switch;

wherein the first switch cannot be activated if the second switch is activated and the second switch cannot be activated if the first switch is activated.

In some embodiments, the power pack has a first drive mechanism engageable with the firing mechanism, and the power pack cannot be removed from the compartment if the first drive mechanism in not in a home position. In some embodiments, the power pack has a second drive mechanism engageable with the articulation mechanism, and the power pack cannot be removed from the compartment if the articulation mechanism in not in a home position.

In some embodiments, opening of the jaws disables a firing mode. In some embodiments, closing of the jaws disables an articulation mode.

In accordance with another aspect of the present disclosure, a surgical fastener applier is provided comprising:

a housing containing a compartment therein;

an elongated member extending distally from the housing;

a first jaw and a second jaw at a distal portion of the elongated member, at least the first jaw movable with respect to the second jaw to clamp tissue between the first and second jaws;

a firing mechanism positioned within the housing, the firing mechanism movable between a first position and a second position, wherein movement to the second position effects firing of fasteners into the tissue clamped between the first and second jaws; and a power pack removably loadable into the compartment, the power pack having a) a first motor and a first engagement member removably engageable with the firing mechanism when the power pack is loaded into the compartment to effect movement of the firing mechanism from the first position to the second position, the first engagement having a home position and an advanced position; and b) a second motor and a second engagement member removably engageable with an articulating mechanism in the housing of the surgical fastener applier to effect movement of an articulation mechanism to effect articulation of the first and second jaws from a linear position to a position angled with respect to a longitudinal axis of the elongated member, the second engagement member having a home position and an advanced position, wherein the power pack can be loaded into the compartment only if the first and second engagements are in the home position.

In some embodiments, the power pack can be removed from the compartment only if the first and second engagement members are in the home position.

In some embodiments, neither a firing switch nor an articulation switch can be activated if the cover is not in the closed position.

In accordance with another aspect of the present invention, a method for powering a surgical stapler is provided comprising:

a) providing a surgical stapler having first and second jaws, an elongated shaft and a housing containing a compartment;

b) loading a reusable power pack into a homing cradle so an articulation mechanism and a firing mechanism within the power pack are in a home position, the power pack having a first motor for firing staples and a second motor for articulation of the jaws; and c) after step (b) removing the power pack from the homing cradle and placing the power pack into the compartment of the housing; and d) wherein the powertrain cannot be loaded into the compartment if the articulation mechanism and the firing mechanism are not in the home position.

In some embodiments, the firing mode cannot be effected if a cover of the compartment is not in the closed position. In some embodiments, the power pack cannot be removed from the compartment if the articulation mechanism and the firing mechanism are not in the home position. In some embodiments, a switch for actuating the firing mechanism cannot be actuated if a switch for the articulation mechanism is activated. In some embodiments, a switch for actuating the articulation mechanism cannot be actuated if a switch for the firing mechanism is activated.

BRIEF DESCRIPTION OF THE DRAWINGS

So that those having ordinary skill in the art to which the subject invention appertains will more readily understand how to make and use the surgical apparatus disclosed herein, preferred embodiments thereof will be described in detail hereinbelow with reference to the drawings, wherein:

FIG. 6A is a side view of the surgical stapler of FIG. 1 showing the handle compartment cover in the open position and further showing the power pack in the process of being inserted in the compartment of the handle;

FIG. 6B is a bottom view of the surgical stapler of FIG. 6A;

FIG. 6C is a cross-sectional view taken along line A-A of FIG. 6B;

FIG. 6D is a close up view of the area of detail AR of FIG. 6C;

FIG. 7A is a top view of the surgical stapler of FIG. 1 with the power pack fully inserted into the compartment in the handle and the cover in the closed position;

FIG. 7B is a cross-sectional view taken along line A-A of FIG. 7A;

FIG. 7C is a close up view of the area of detail B of FIG. 7B showing the firing mechanism at the distal end for firing staples;

FIG. 8A is a top view of the surgical stapler of FIG. 1 showing the power pack fully inserted and the cover of the handle compartment in the closed position, the view the same as FIG. 7A but having section line E-E;

FIG. 8B is a cross-sectional view taken along line E-E of FIG. 8A, the view being the same as FIG. 7B but having section lines F-F and identified area of detail B;

FIG. 9 is a cross-sectional view taken along line F-F of FIG. 8B;

FIG. 10 is a close up view of the area of detail G of FIG. 8B;

FIG. 11 is a close up view of the area of detail H of FIG. 9;

FIG. 14A is a side view illustrating an alternate embodiment having a power pack for effecting both firing and articulation of the surgical stapler, the power pack shown fully inserted into the compartment of the handle of the surgical stapler and the compartment cover shown in the closed position;

FIG. 14B is a top view of the surgical stapler of FIG. 14A;

FIG. 14C is a cross-sectional view taken along line C-C FIG. 14B;

FIG. 15A is a close up view of the area of detail D of FIG. 14C;

FIG. 15C is a top view of the power pack of FIG. 14A for effecting both firing and articulation of the surgical stapler;

FIG. 15D is a cross-sectional view taken along line AW-AW of FIG. 15C;

FIG. 15E is a side view of the power pack of FIG. 14A;

FIG. 15F is a cross-sectional view taken along line AT-AT of FIG. 15E;

FIG. 16A is a top view of the surgical stapler of FIG. 14A, the view being the same as FIG. 14B but having section line E-E;

FIG. 16B is a side view of the surgical stapler of FIG. 14A, the view being the same as FIG. 14C but having section line F-F and identified area of detail G;

FIG. 16C is a cross-sectional view taken along line F-F of FIG. 15C;

FIG. 16D is a close up view of the area of detail H of FIG. 16C;

FIG. 20 is a cross-sectional side view of the surgical stapler of FIG. 14A, the view being the same as FIG. 14C but having identified areas of detail Q, R and S;

FIG. 21A is an enlarged view of the area of detail Q of FIG. 20;

FIG. 21B is an enlarged view of the area of detail R of FIG. 19A;

FIG. 21C is an enlarged view of the area of detail S of FIG. 19A;

FIG. 24A is a top view of the motor and drive mechanism (assembly) of the power pack of an alternate embodiment having a belt drive;

FIG. 24B is a side view of the motor and drive mechanism of FIG. 24A;

FIG. 24C is a perspective view of the motor and drive mechanism of FIG. 24A;

FIG. 24D is a front view of the motor and drive mechanism of FIG. 24A;

FIG. 26A is a top view of the motor and drive mechanism (assembly) of the power pack of another alternate embodiment having a belt drive;

FIG. 26B is a side view of the motor and drive mechanism of FIG. 26A;

FIG. 26C is a perspective view of the motor and drive mechanism of FIG. 26A;

FIG. 26D is a front view of the motor and drive mechanism of FIG. 26A;

FIG. 27A is a top view of the motor and drive mechanism (assembly) of the power pack of an alternate embodiment having a belt drive;

FIG. 27B is a side view of the motor and drive mechanism of FIG. 27A;

FIG. 27C is a perspective view of the motor and drive mechanism of FIG. 27A;

FIG. 27D is a front view of the motor and drive mechanism of FIG. 27A;

FIG. 27E is a view similar to FIG. 27B showing engagement with the stapler firing rod;

FIG. 33A is a top view of an alternate embodiment of the surgical instrument containing the power pack of FIG. 3A within the handle compartment, the surgical instrument being an endoscopic scissor;

FIG. 33B is a side view of the endoscopic scissor of FIG. 33A;

FIG. 33C is a perspective view of the endoscopic scissor of FIG. 33A;

FIG. 33D is a front view of the endoscopic scissor of FIG. 33A;

FIG. 37B is a side view of the surgical instrument of FIG. 37A;

FIG. 37C is a perspective view of the surgical instrument of FIG. 37A showing the power pack and battery pack within the compartment of the surgical instrument;

FIG. 38 is a concept diagram of readying the power train for use in accordance with one embodiment of the present invention;

FIG. 39 is a concept diagram illustrating the relationship between instrument jaw position and articulation and firing enabling;

Figure 40A:
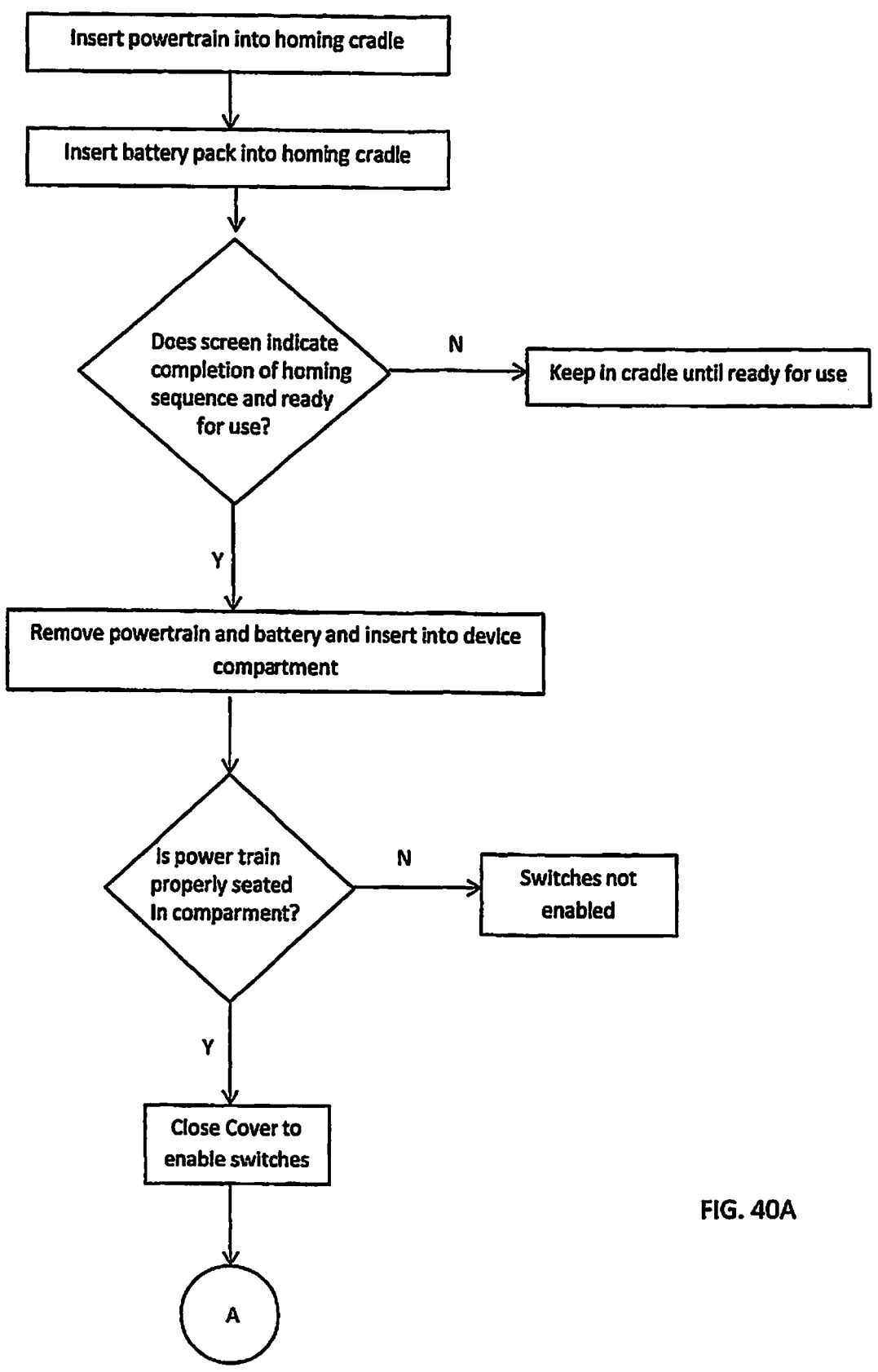
Figure 40B:
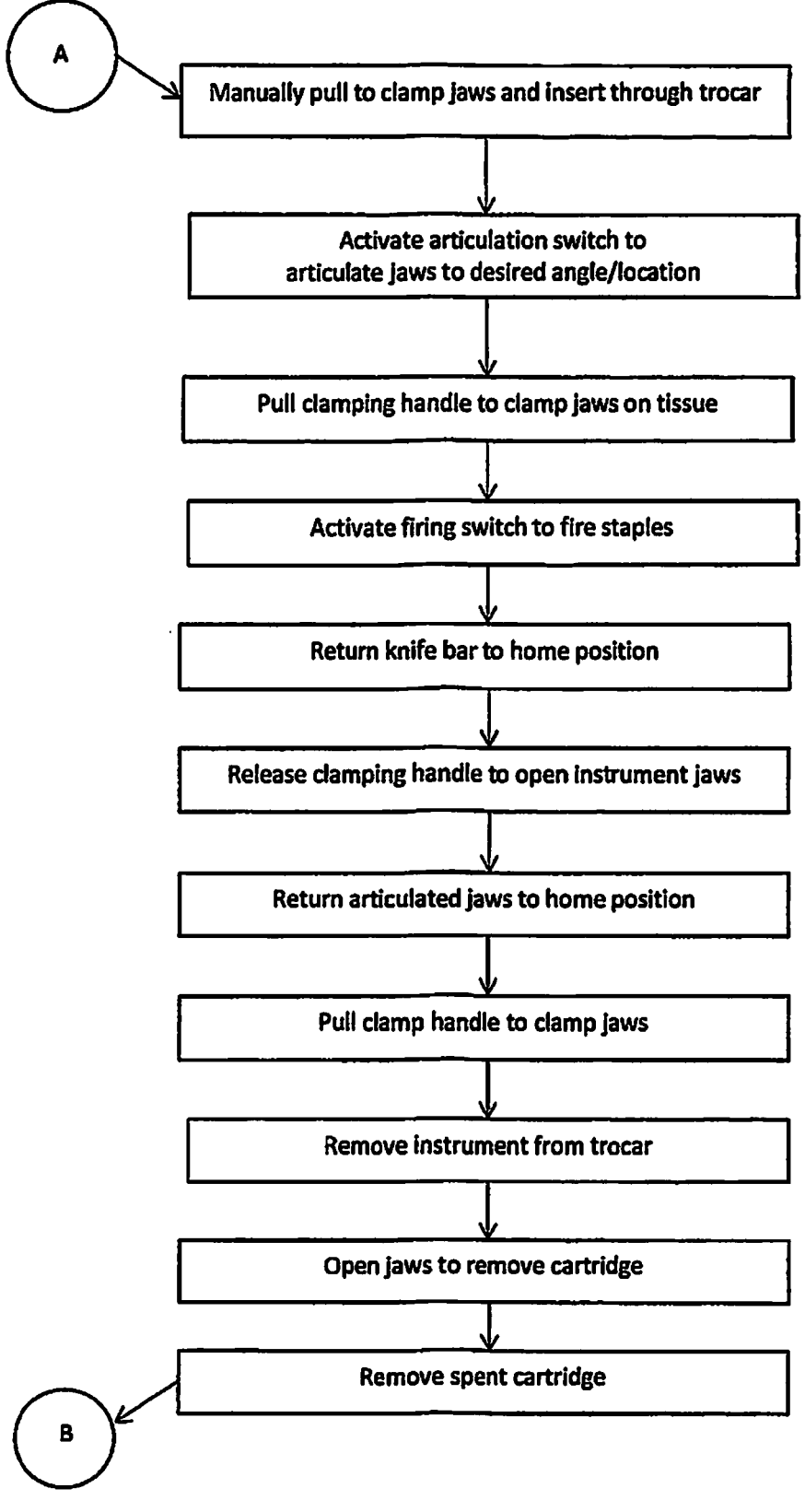
Figure 40C:
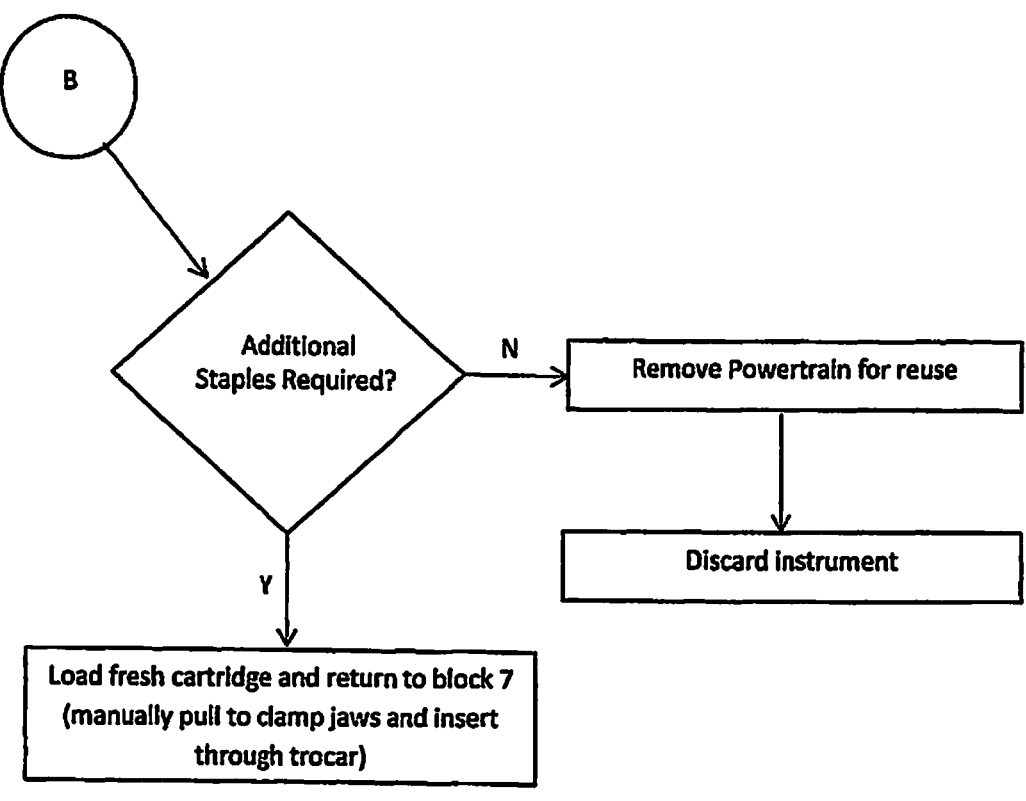
Figures 41A, 41B:
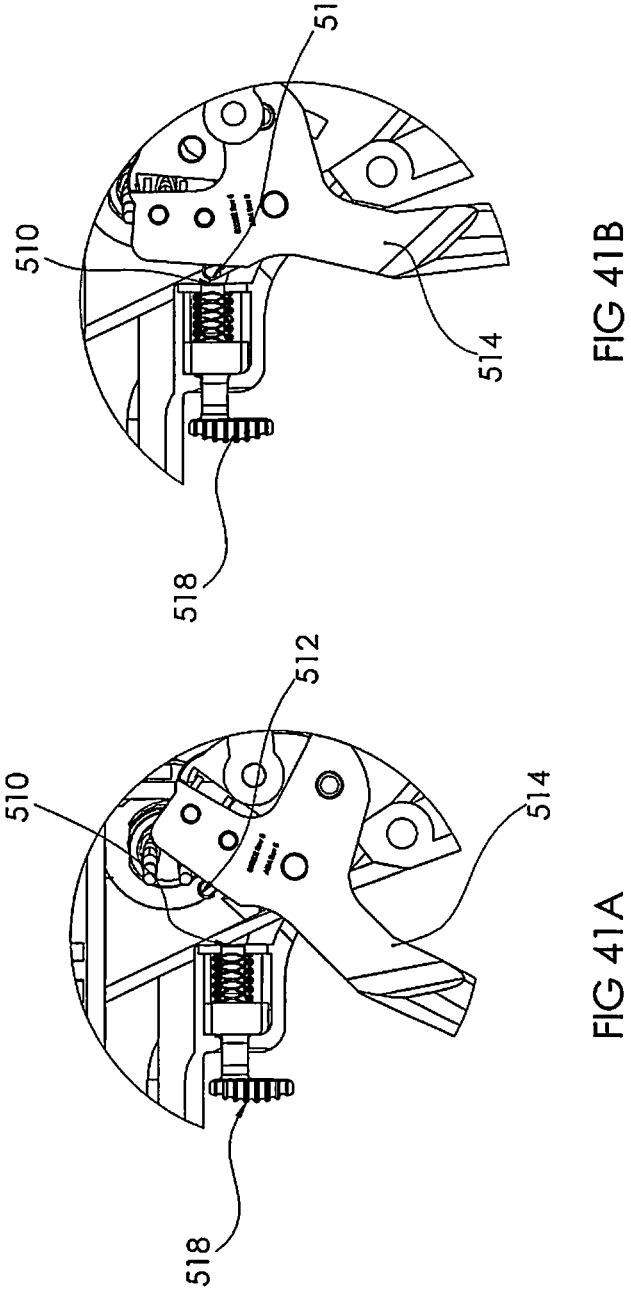
Figures 42A, 42B, 42C, 42D, 42E, 42F:
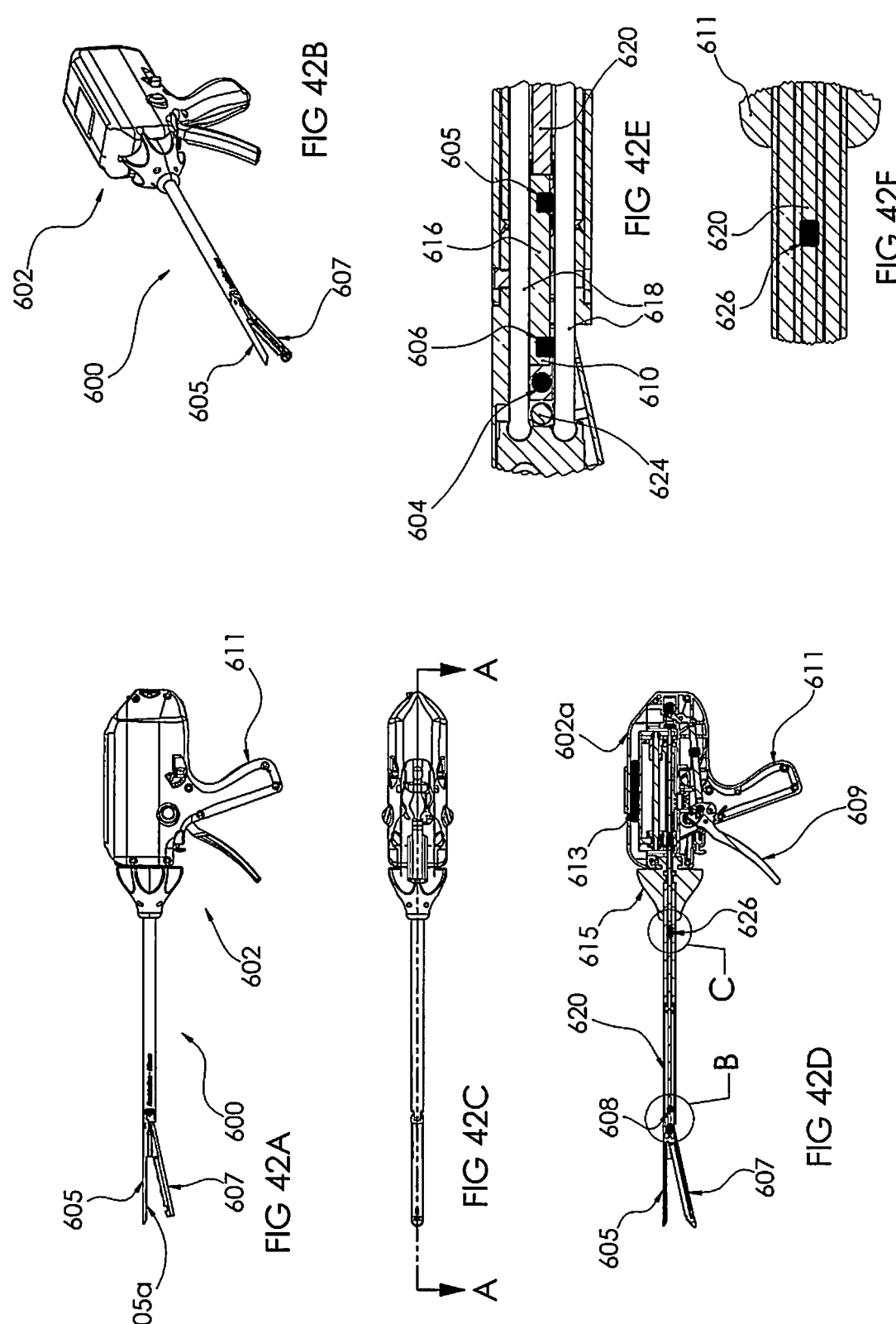
Figures 43A, 43B, 43C:
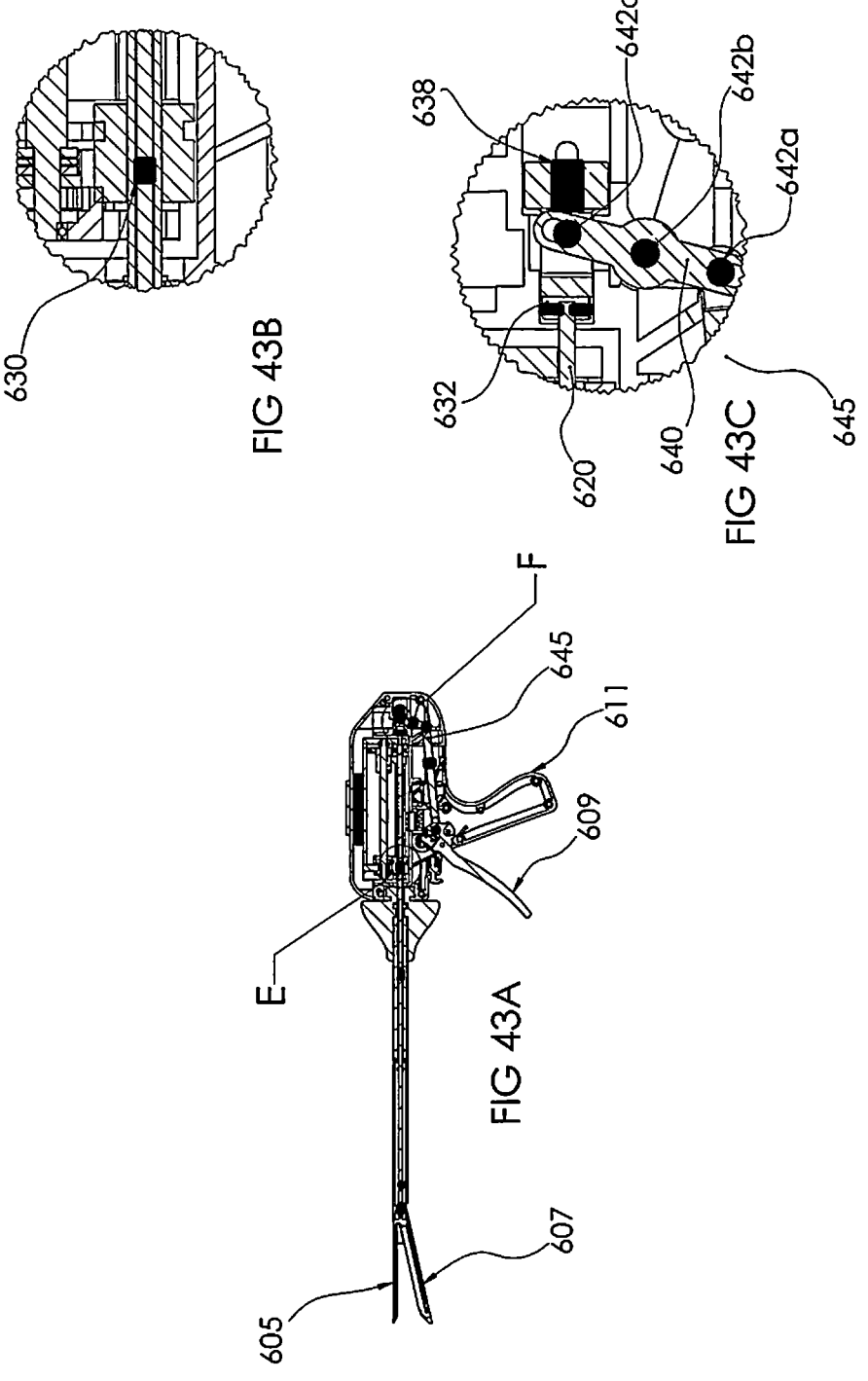
Figures 44A, 44B, 44C:
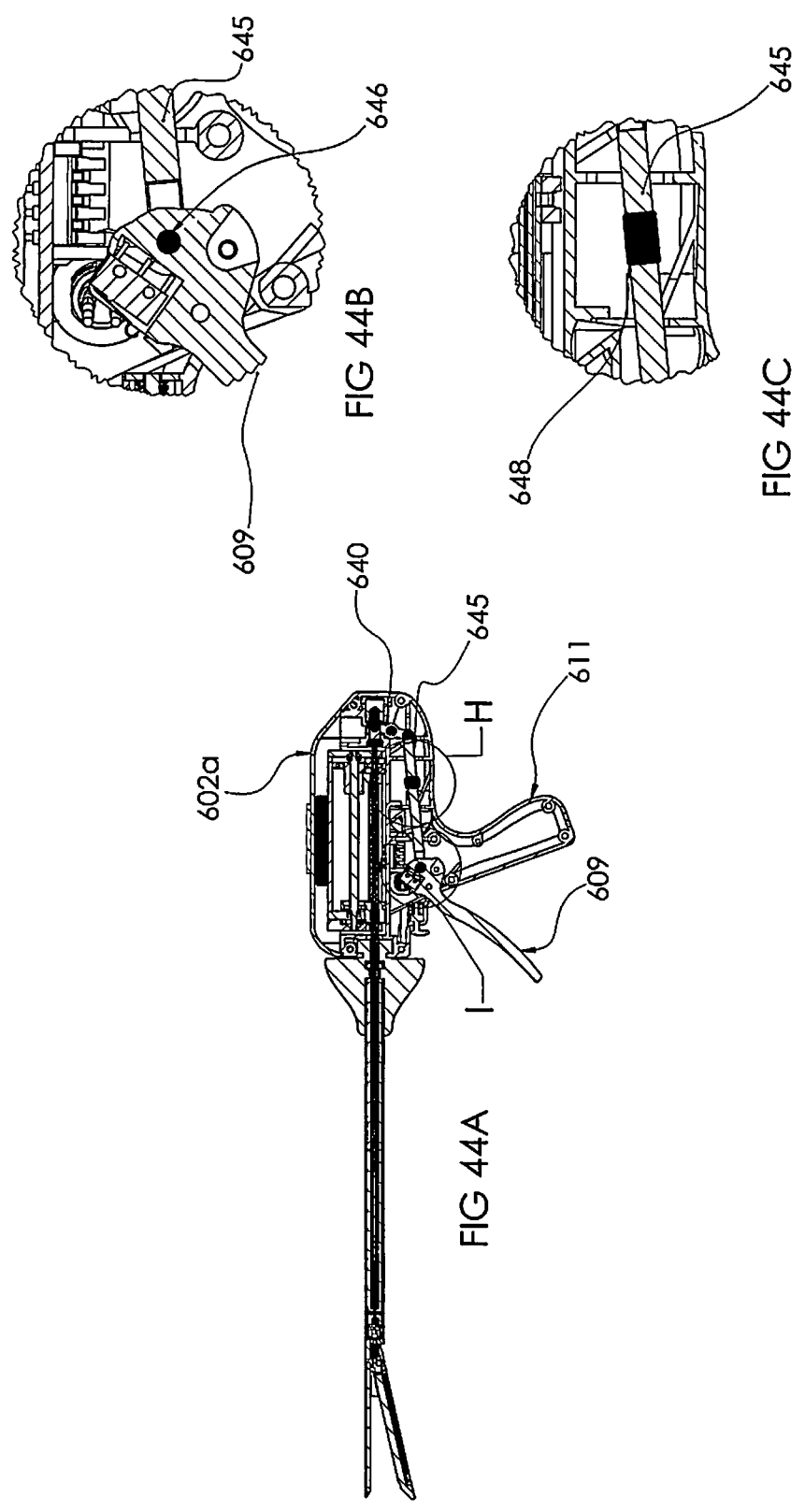
Figures 45A, 45B, 45C, 45D, 45E, 45F:
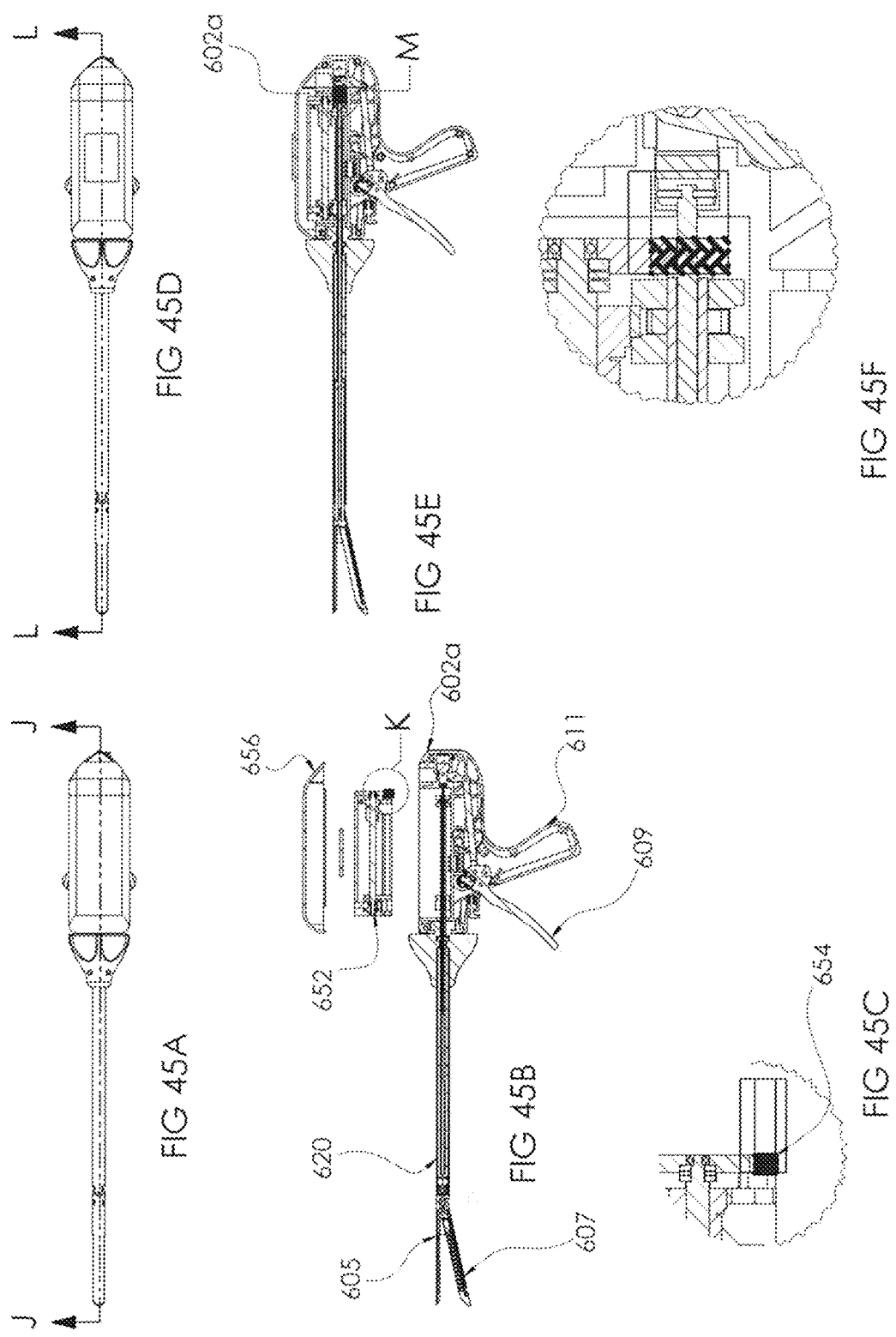
Figure 48:
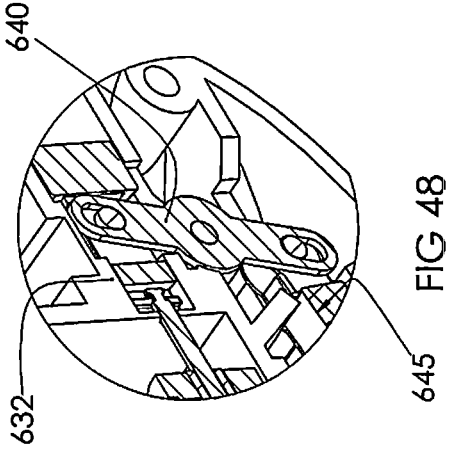
Figure 47:
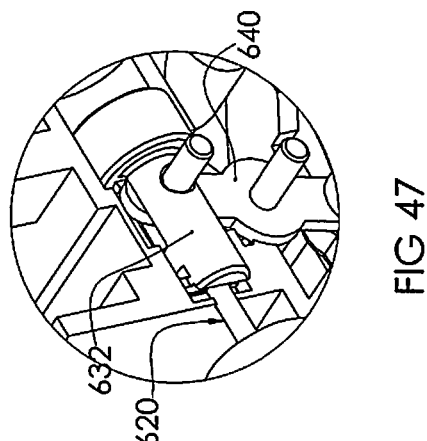
Figure 46:
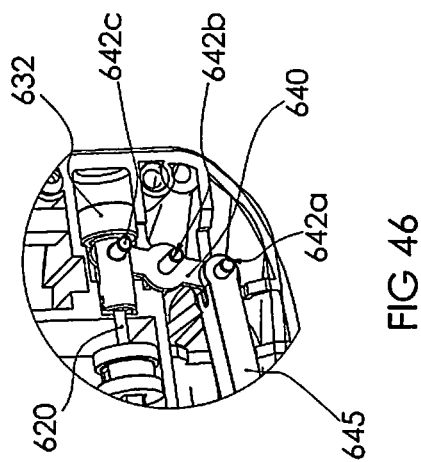
Figures 49, 50, 51:
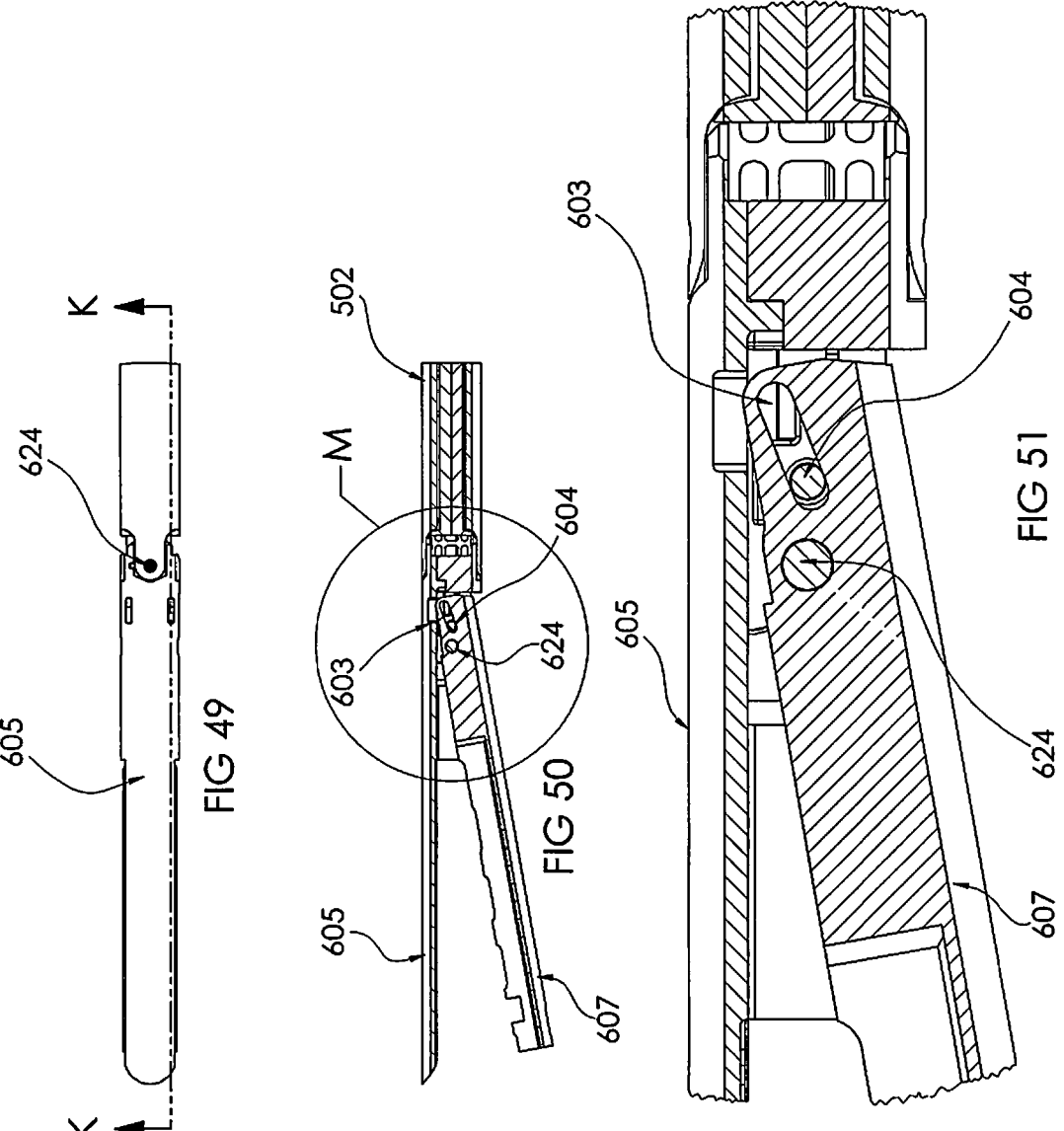
Figure 52:
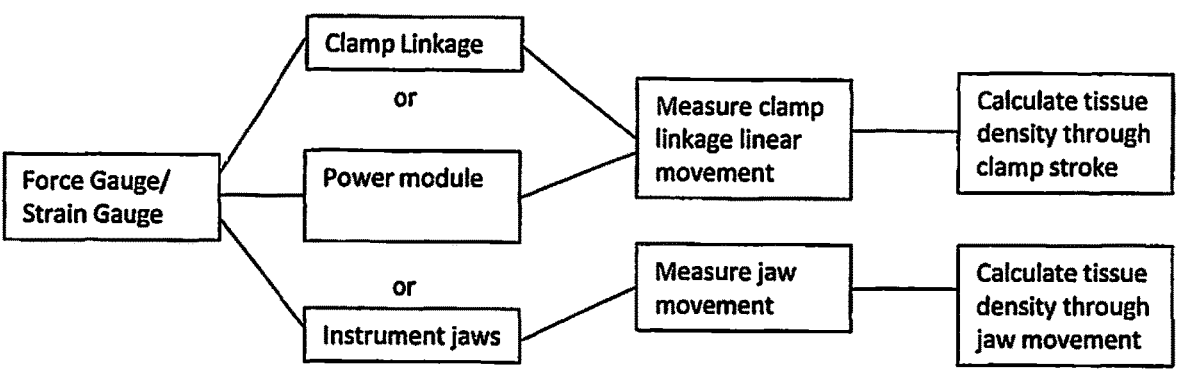
Figure 53:
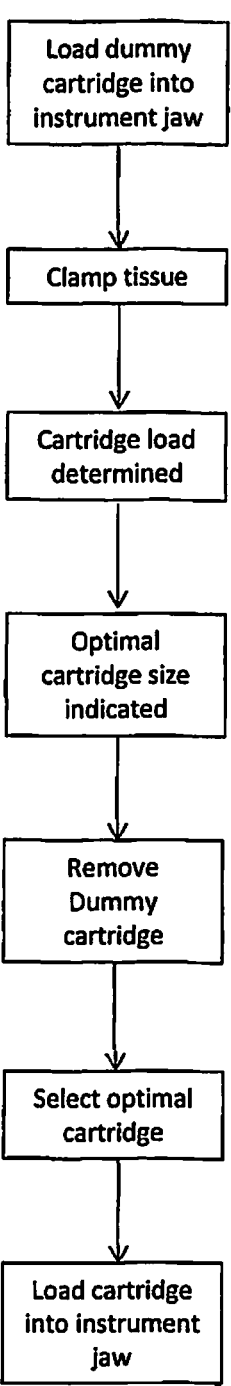
Figure 54:
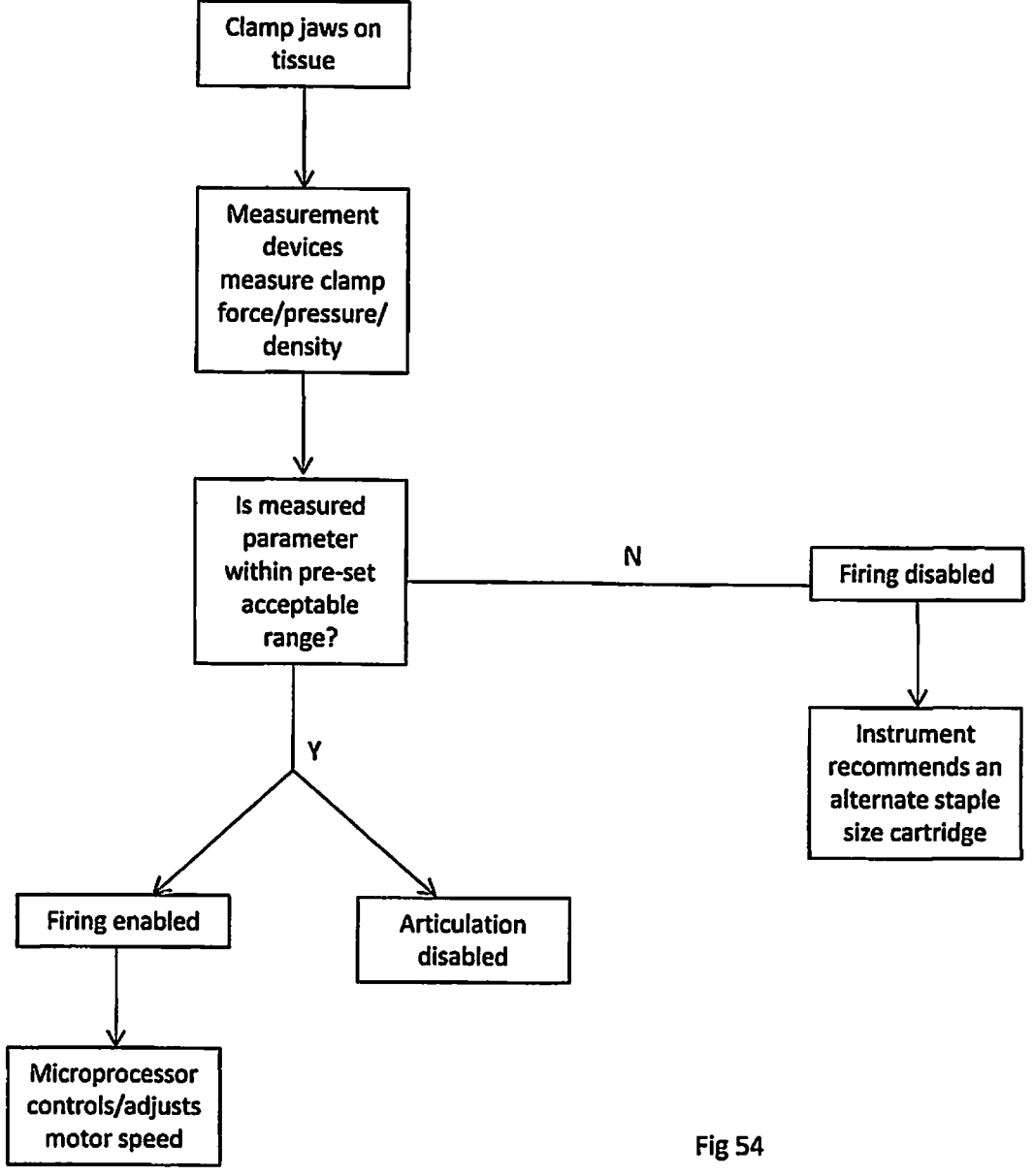

FIGS. 40A, 40B and 40C shown the steps of use of the instrument of the present invention;

FIG. 41A is a side view of one embodiment of the handle portion of the surgical instrument of the present invention illustrating the clamping handle in the open position so the firing switch cannot be activated;

FIG. 41B is a side view of the clamping handle in the closed position so the firing switch can be activated;

FIGS. 42A-43C illustrate alternate embodiments of the surgical instrument of the present invention having measurement devices to provide feedback, wherein:

FIG. 42A is a side view of the surgical instrument;

FIG. 42B is a perspective view of the surgical instrument;

FIG. 42C is a top view of the surgical instrument;

FIG. 42D is a cross-sectional view taken along line A-A of FIG. 42C;

FIG. 42E is an enlarged view of the area of detail B of FIG. 42D;

FIG. 42F is an enlarged view of the area of detail C of FIG. 42D;

FIG. 43A is a cross-sectional view identical to the cross-sectional view of FIG. 42D illustrated to identify the areas of detail E and F;

FIG. 43B is an enlarged view of the area of detail E of FIG. 43A;

FIG. 43C is an enlarged view of the area of detail F of FIG. 43A;

FIG. 44A is a cross-sectional view identical to the cross-sectional view of FIG. 42D illustrated to identify the areas of detail H and I;

FIG. 44B is an enlarged view of the area of detail I of FIG. 44A;

FIG. 44C is an enlarged view of the area of detail H of FIG. 44A;

FIGS. 45A-45F illustrate an alternate embodiment of the surgical instrument of the present invention having a feedback feature (measurement device) in the power pack, wherein:

FIG. 45A is a top view of the surgical instrument with the power pack being loaded into the instrument;

FIG. 45B is a cross-sectional view taken along line J-J of FIG. 45A showing the power pack being loaded into the instrument;

FIG. 45C is an enlarged view of the area of detail K of FIG. 45B;

FIG. 45D is a top view of the surgical instrument with the power pack loaded into the instrument;

FIG. 45E is a cross-sectional view taken along line L-L of FIG. 45A showing the power pack in the instrument;

FIG. 45F is an enlarged view of the area of detail M of FIG. 45E;

FIG. 46 is an enlarged perspective view of components within the handle assembly;

FIG. 47 is a perspective view of the darkened components of FIG. 46 (with the handle housing removed);

FIG. 48 is a top perspective view of the darkened components of FIG. 46 (with the handle housing removed);

FIG. 49 is an enlarged side view illustrating a cam slot arrangement for closing the jaws of the instrument, the cartridge jaw shown in the open (unclamped) position;

FIG. 49 is top view of the jaw assembly;

FIG. 50 is a cross-sectional view taken along line K-K of FIG. 49 showing the cartridge jaw in the open unclamped position;

FIG. 51 is an enlarged view of the area of detail designated in FIG. 50;

FIG. 52 is a block diagram depicting various measurement devices;

FIG. 53 is a flow chart depicting utilization of a dummy cartridge to measurement;

FIG. 54 is a flow chart depicting motor speed adjustment based on measurements.

Figures 55, 56, 57A, 57B:
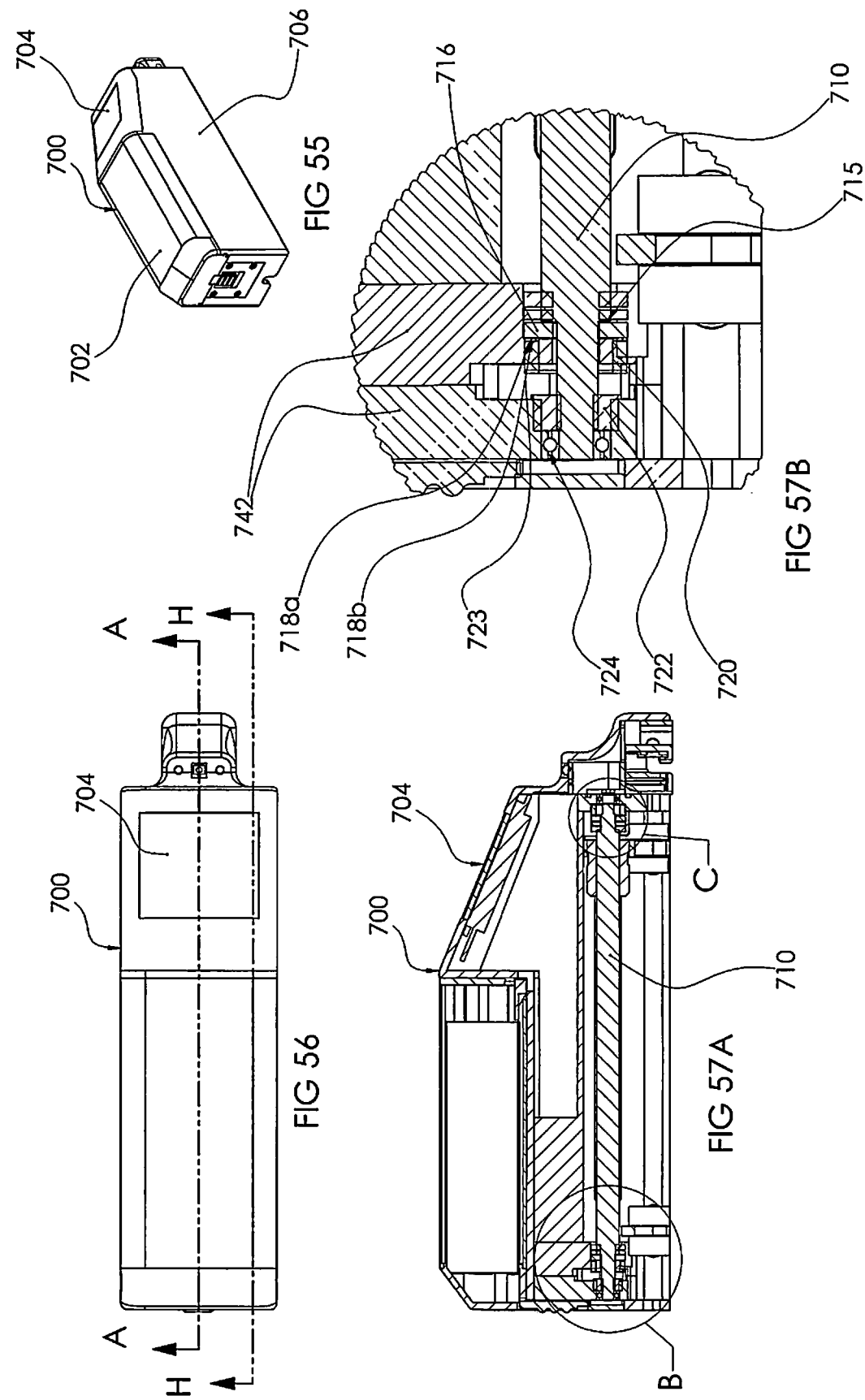
Figure 57C:
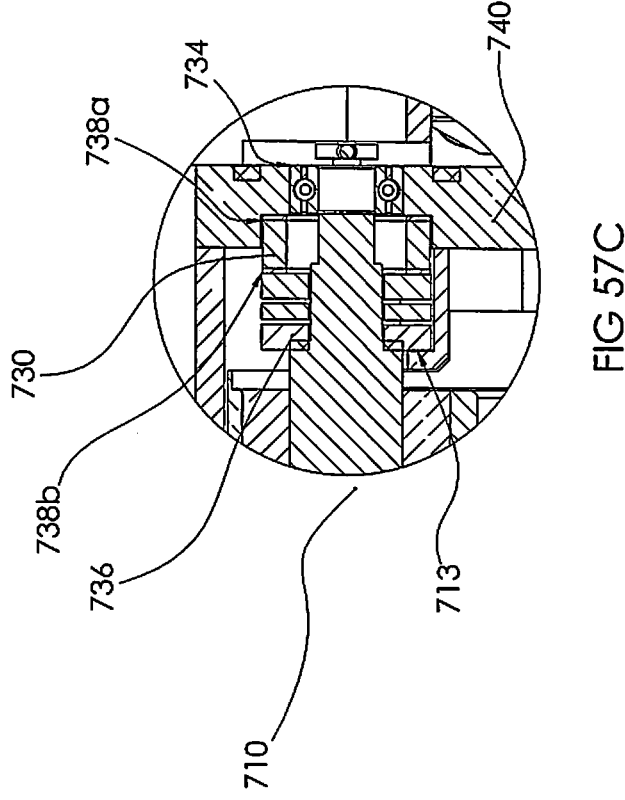
Figures 58, 59, 60A, 60B:
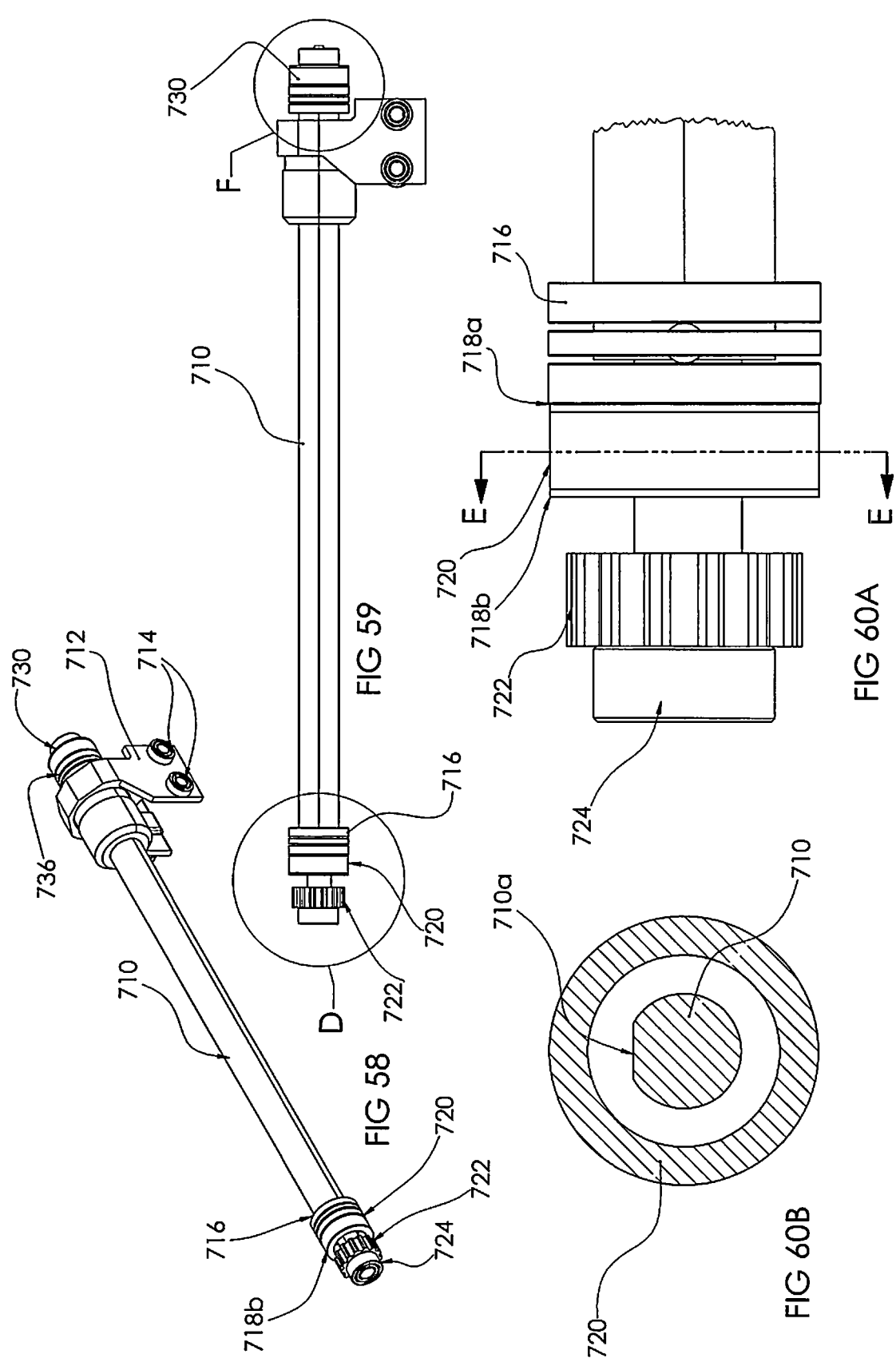
Figure 61A:
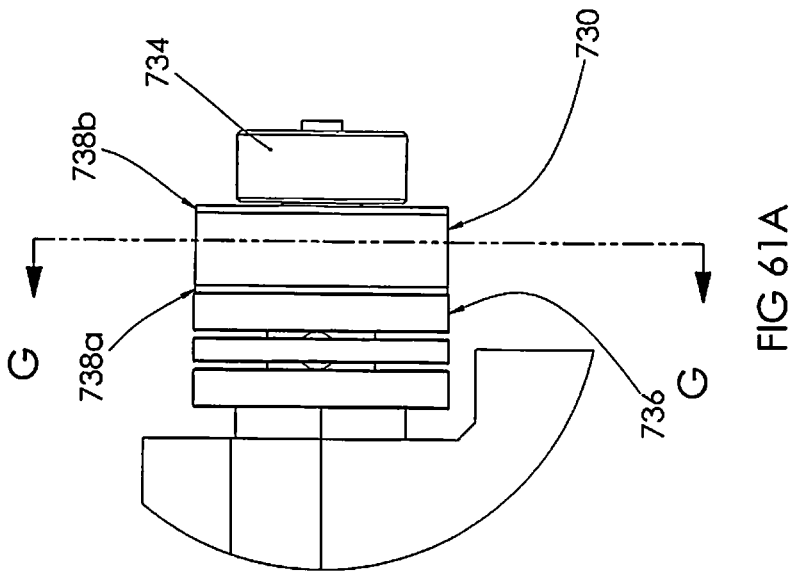
Figure 61B:
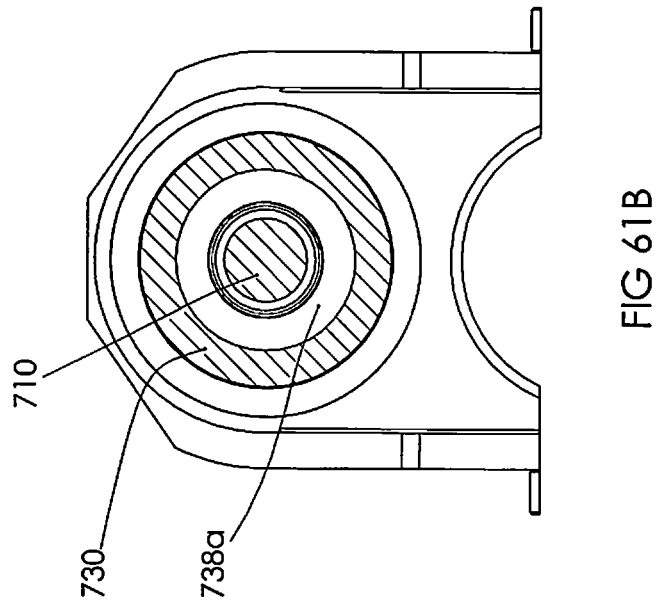
Figures 62A, 62B:
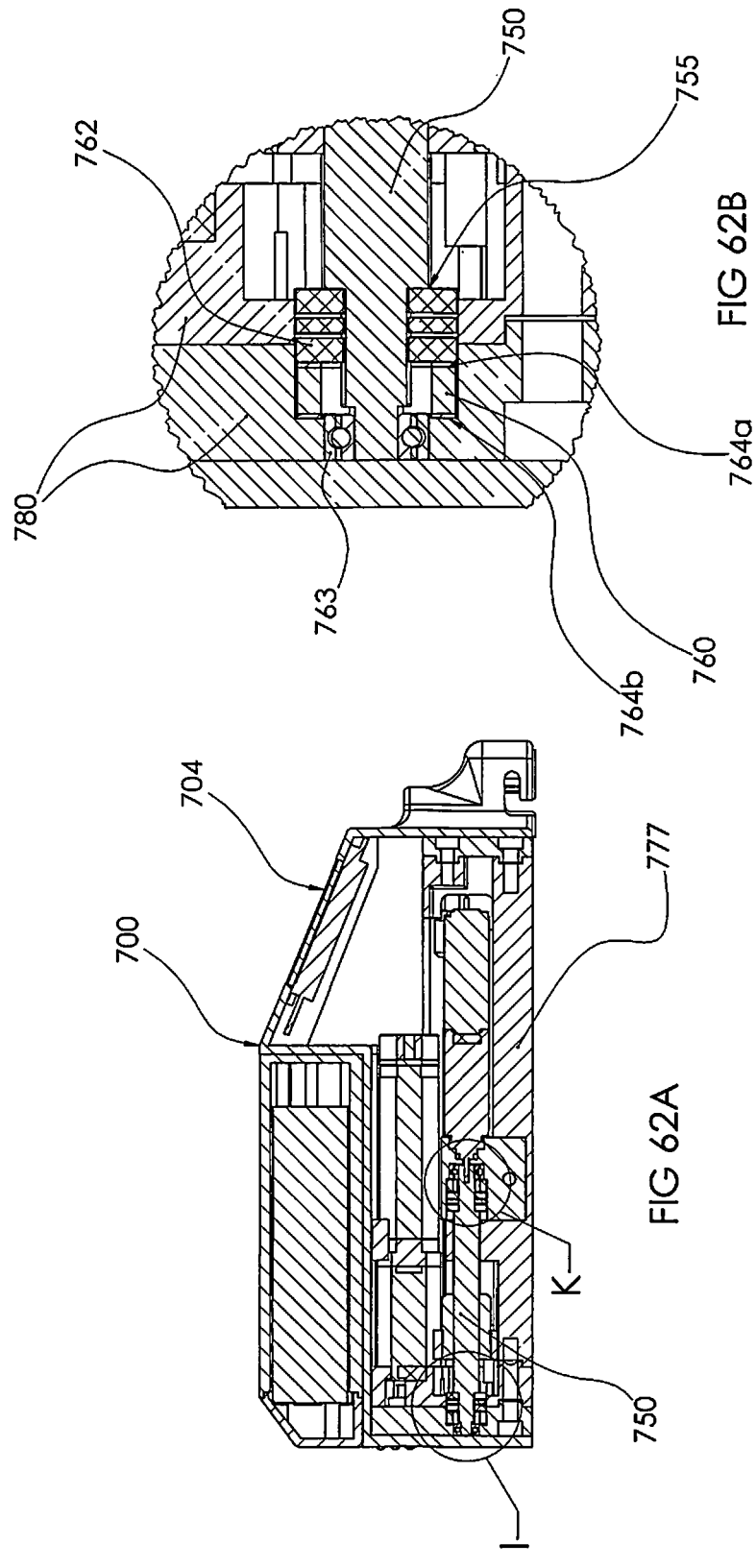
Figure 62C:
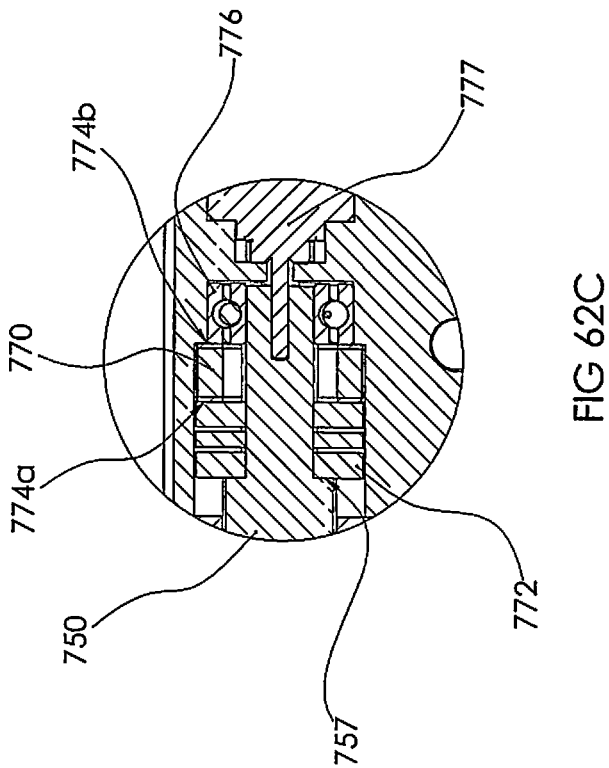
Figures 63, 64, 65A, 65B:
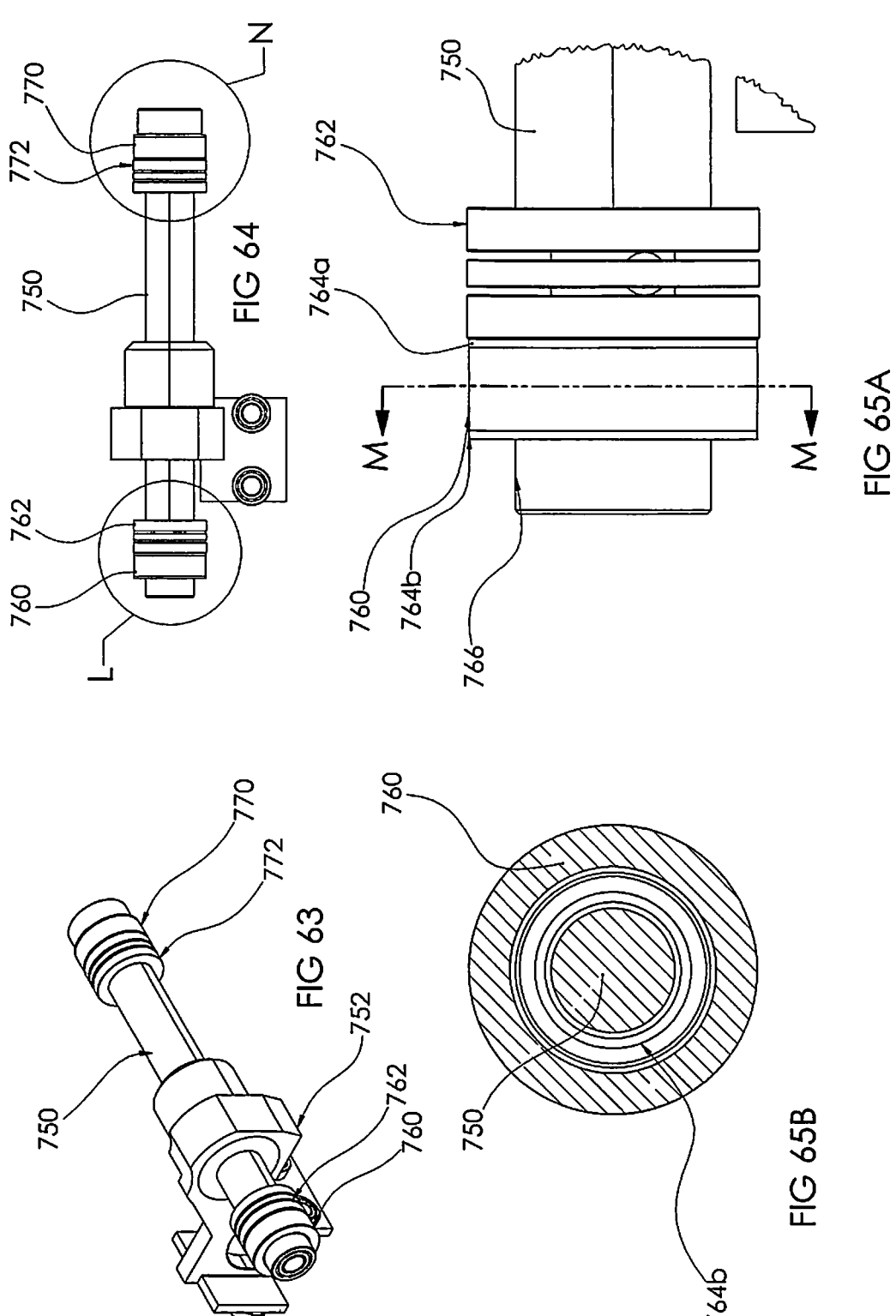
Figures 66A, 66B:
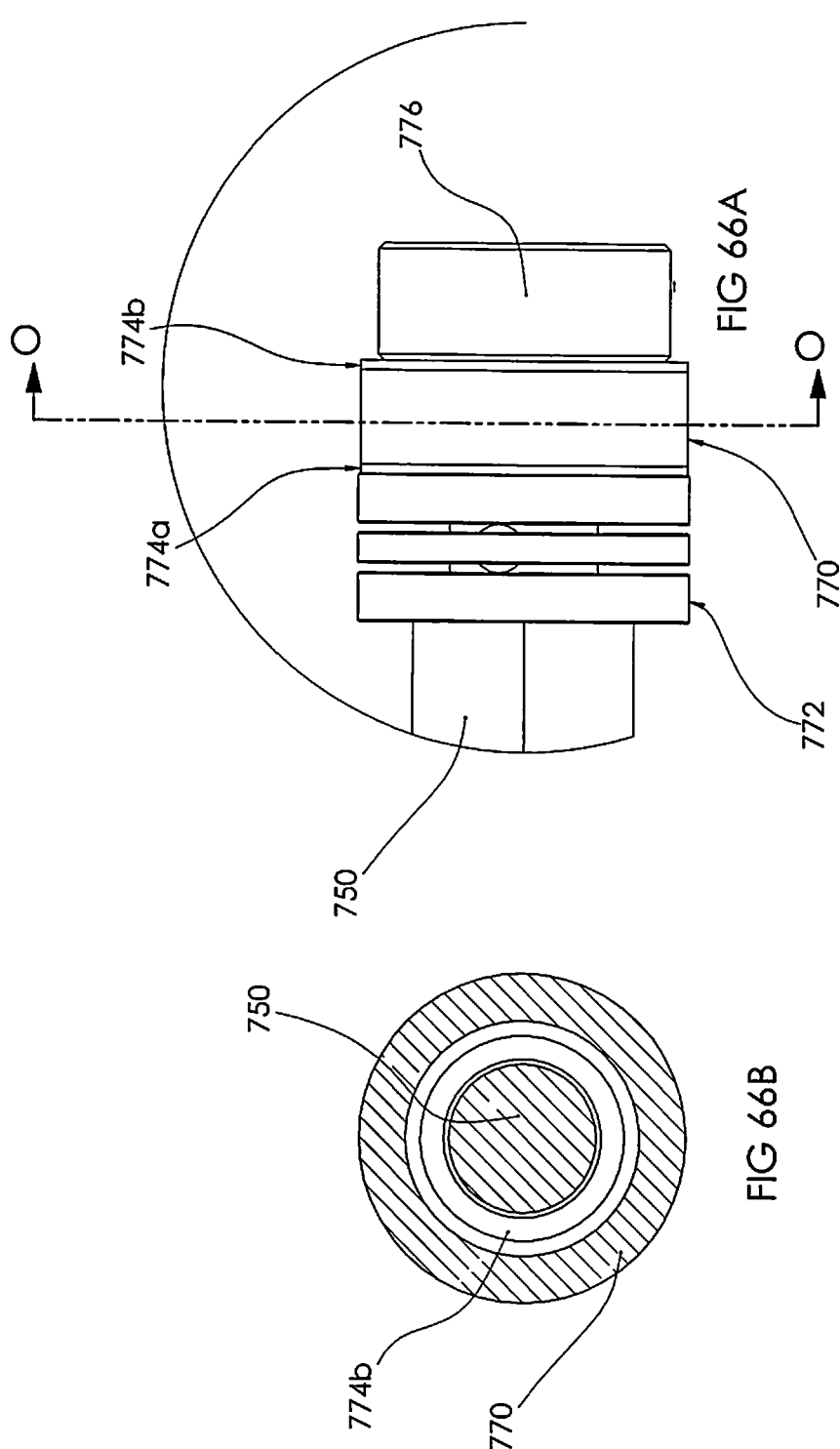
Figures 67, 69A, 69B, 69C, 69D:
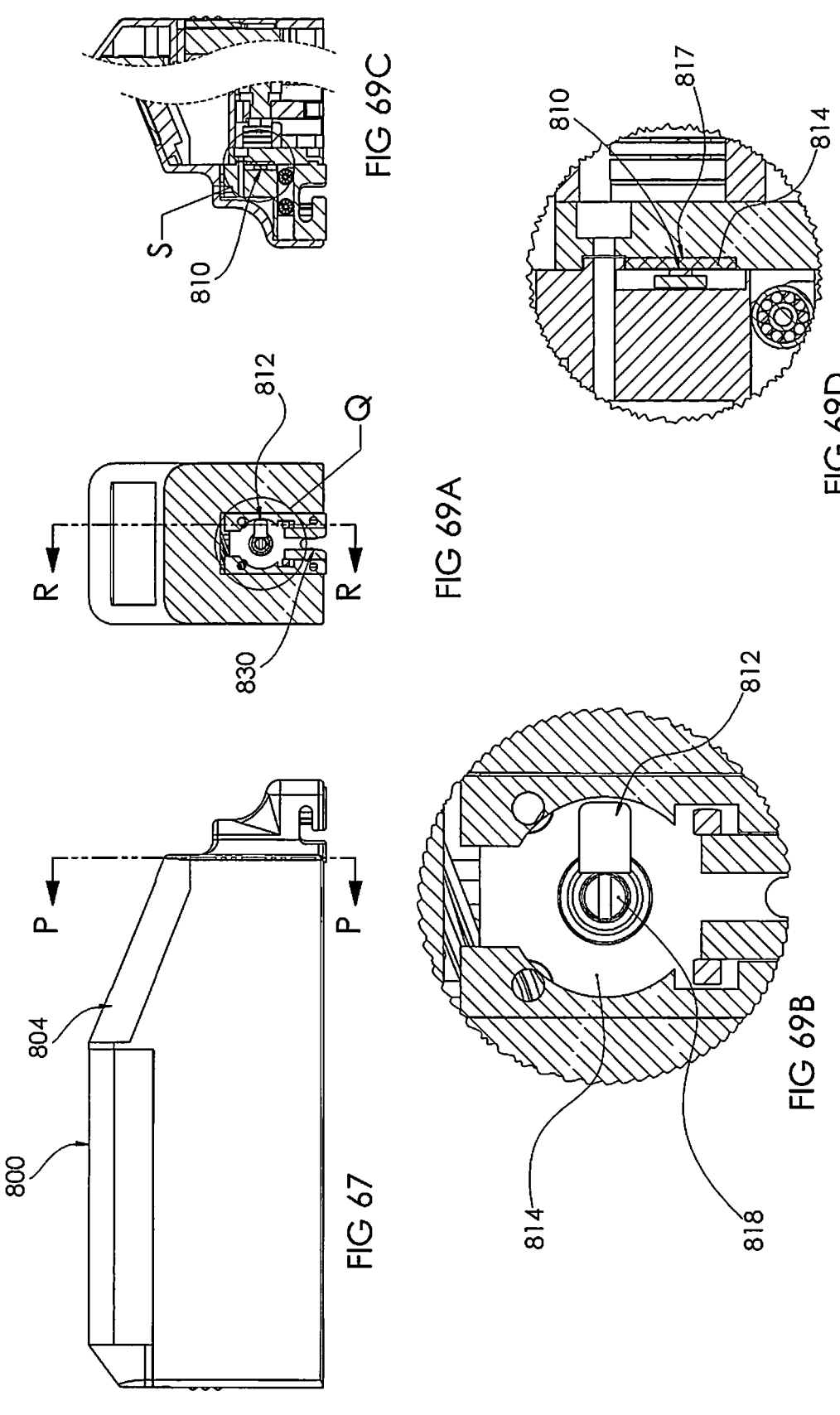
Figure 68:
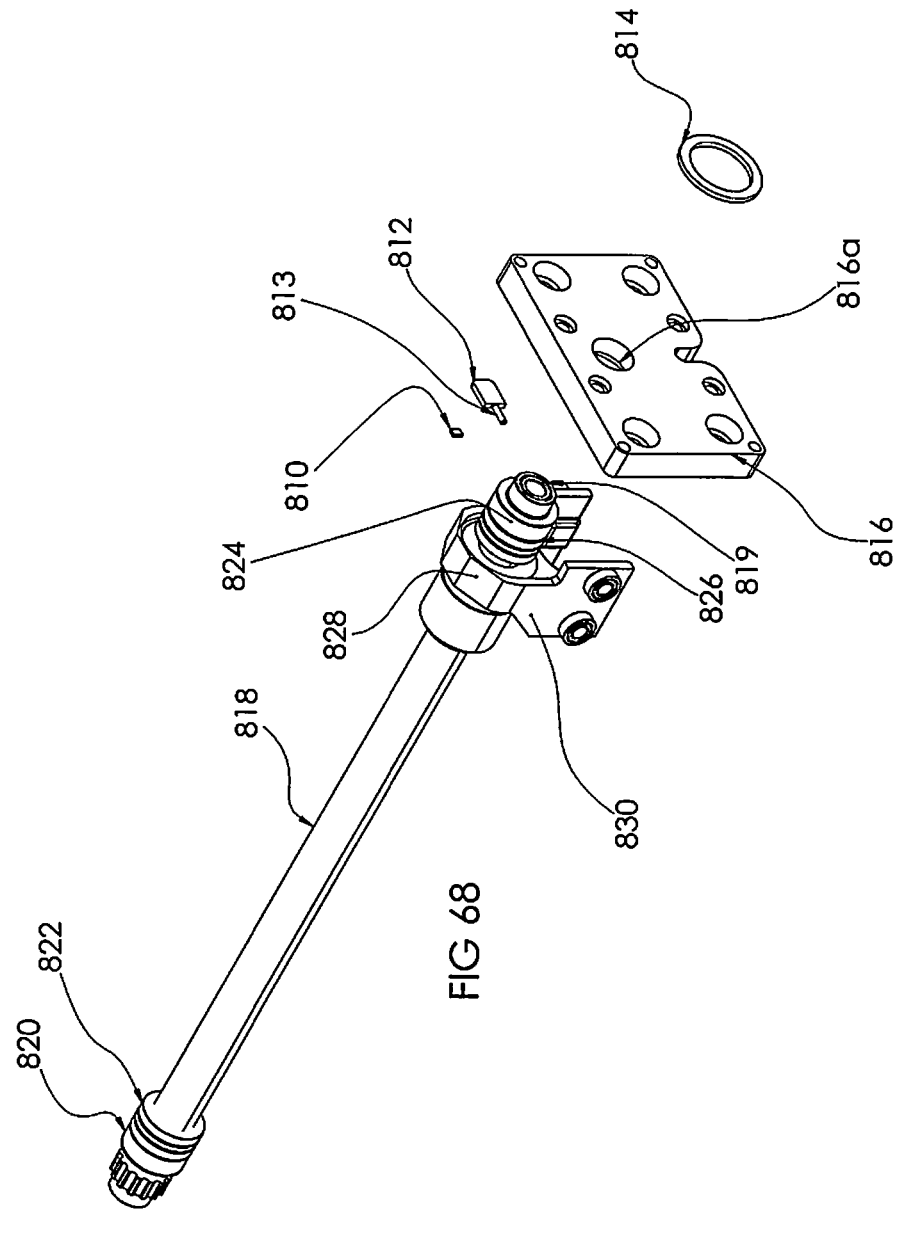
Figures 70, 71:
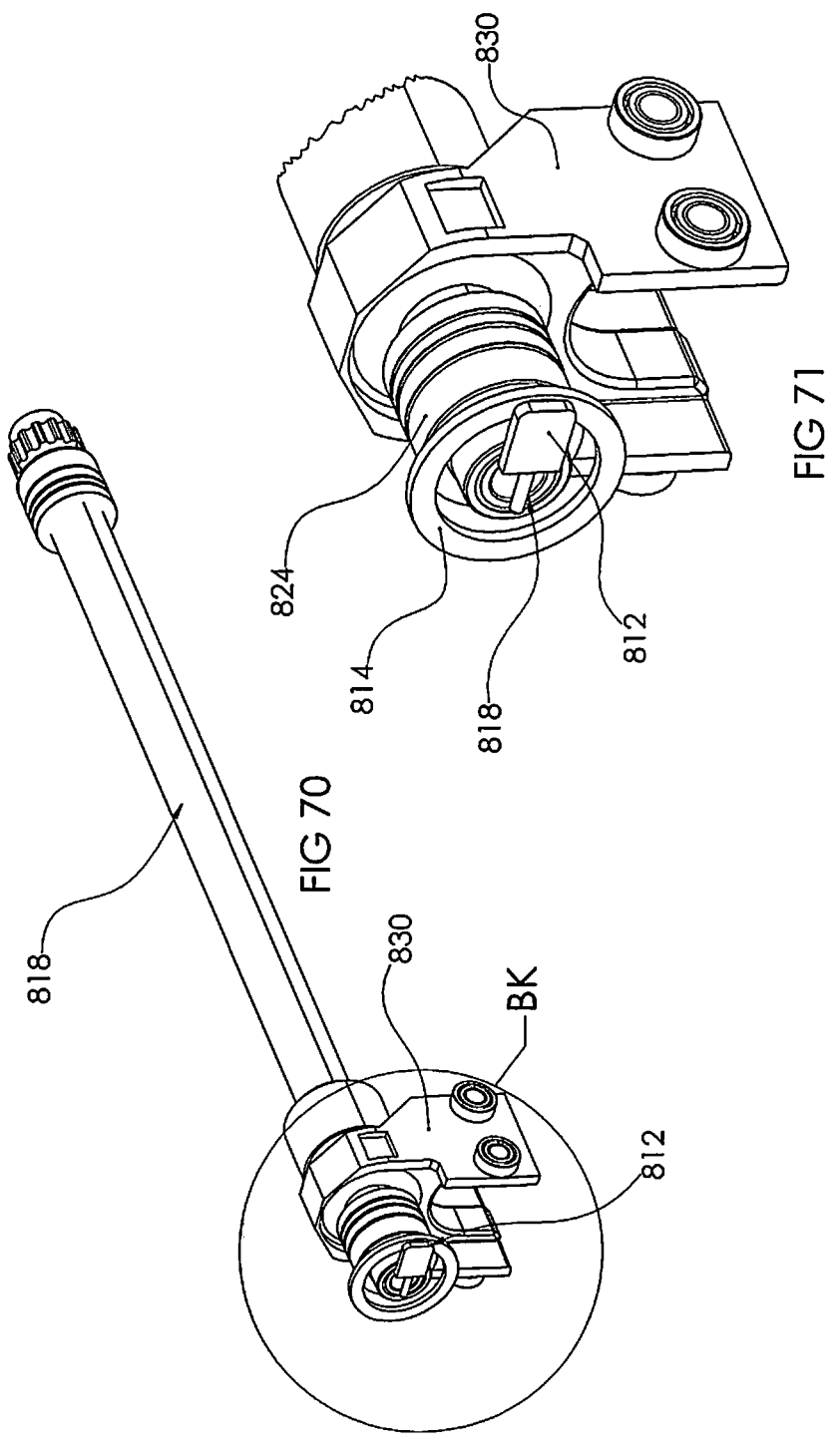
Figures 72, 73A, 73B:
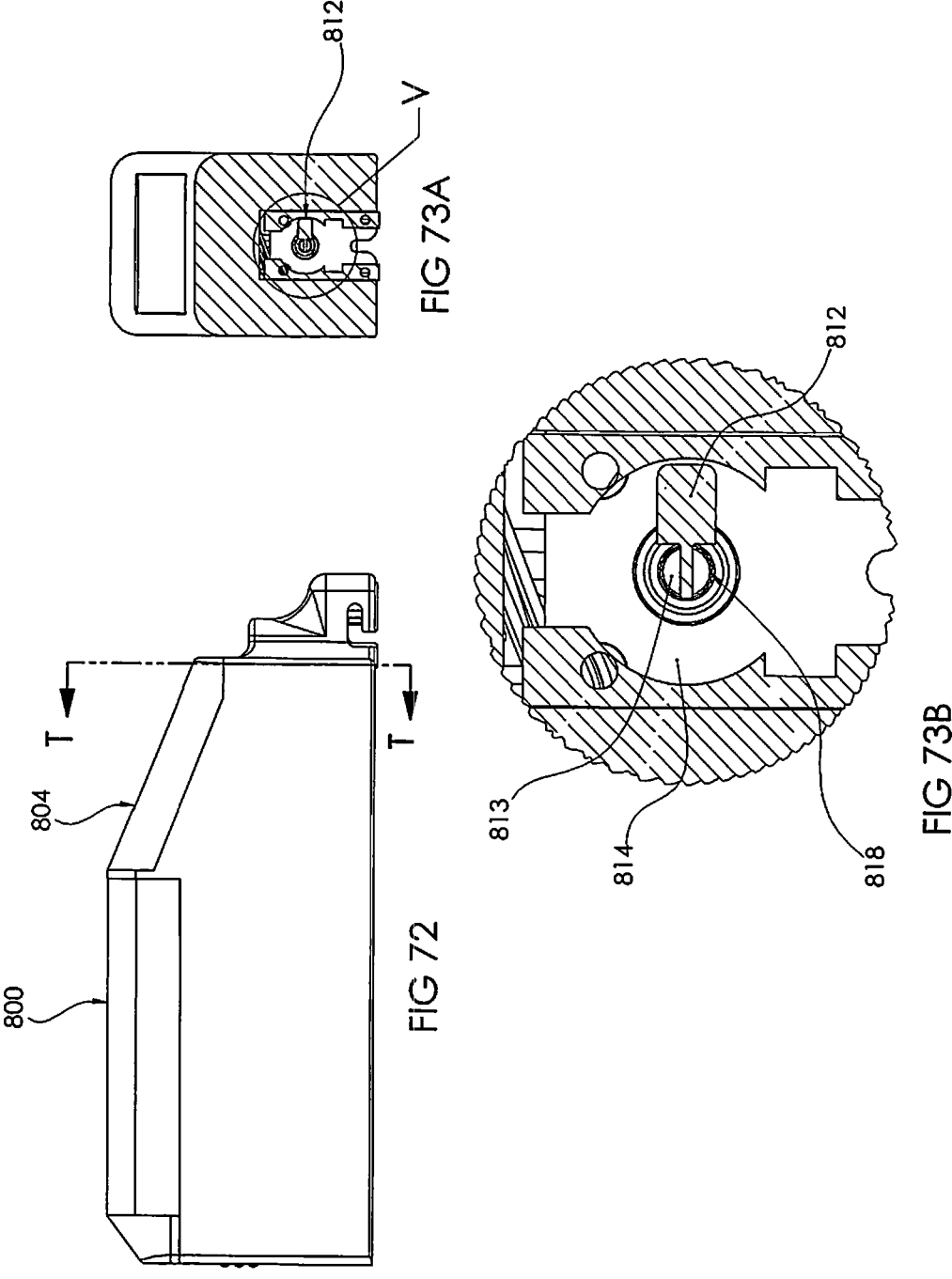
Figures 74, 75, 76A, 76B, 76C:
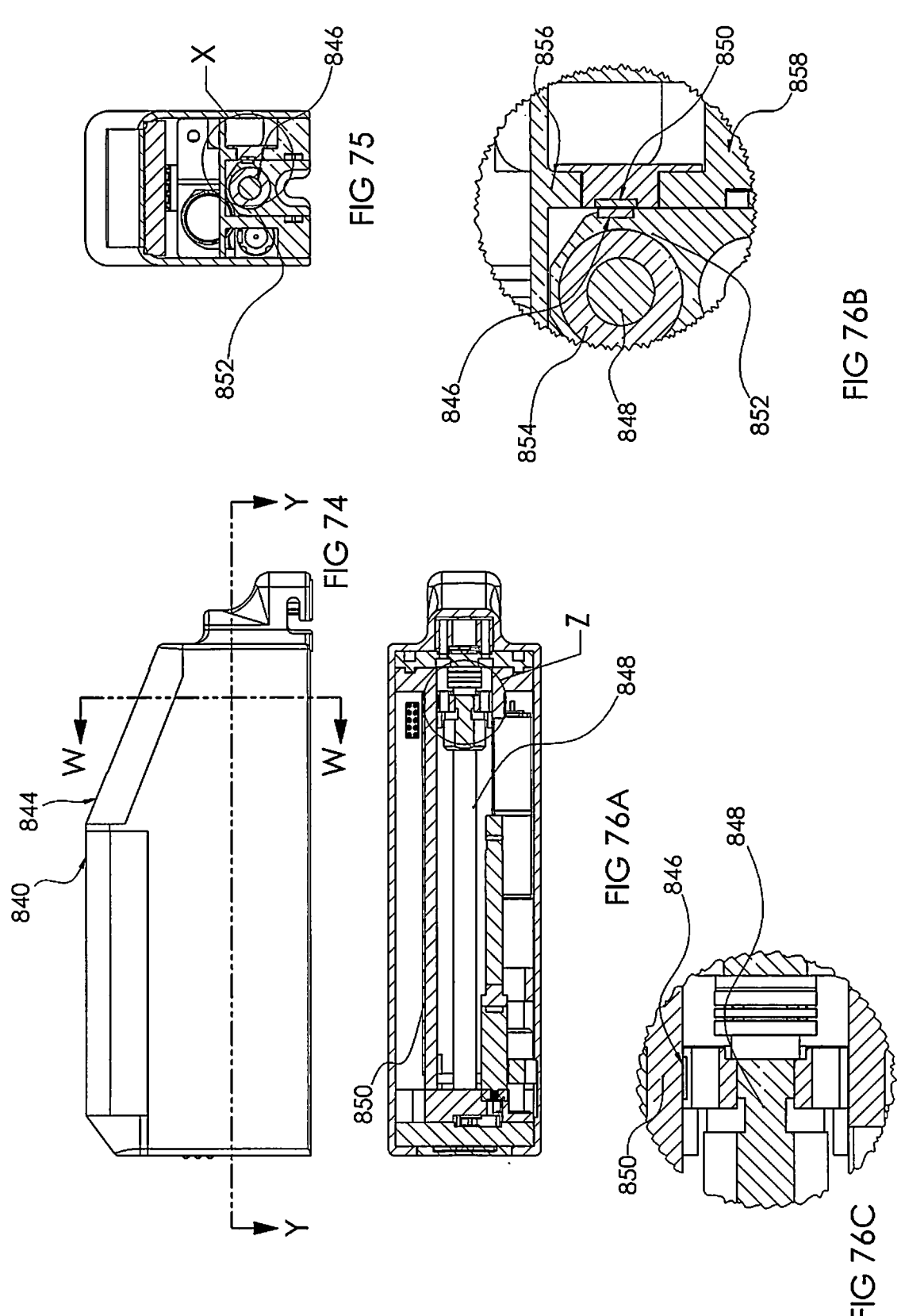
Figures 77, 78:
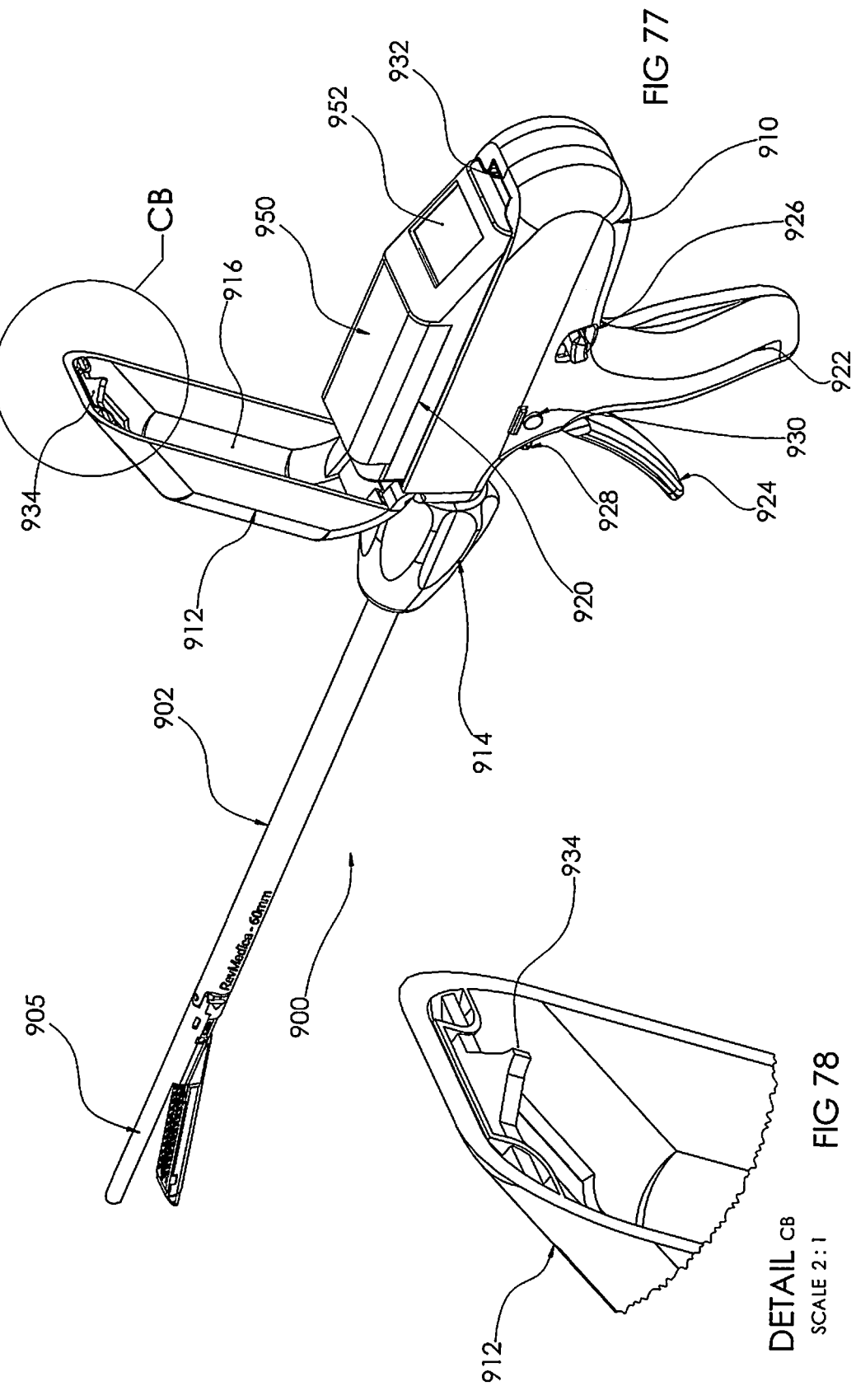
Figures 79, 80:
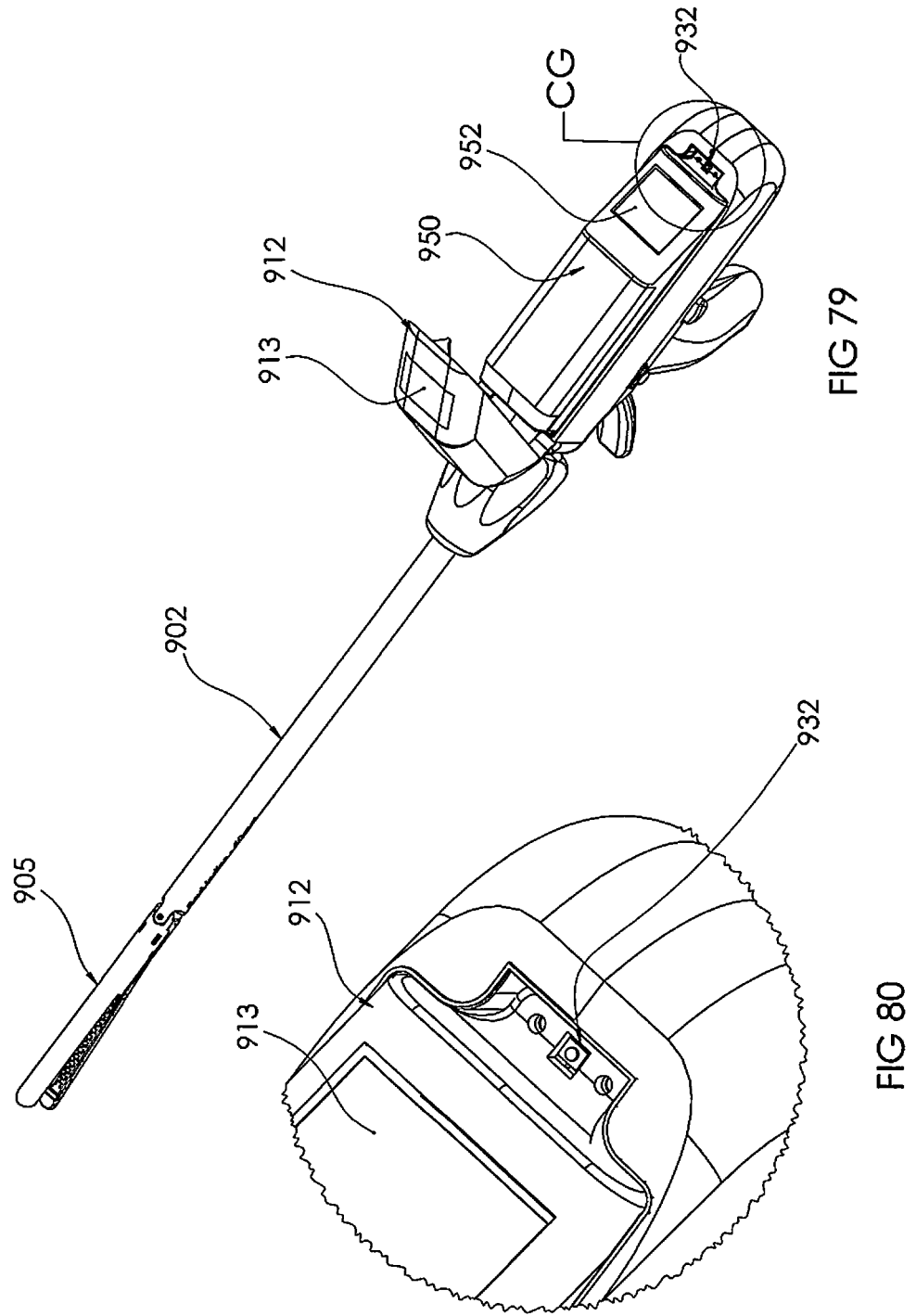
Figures 81, 82A, 82B:
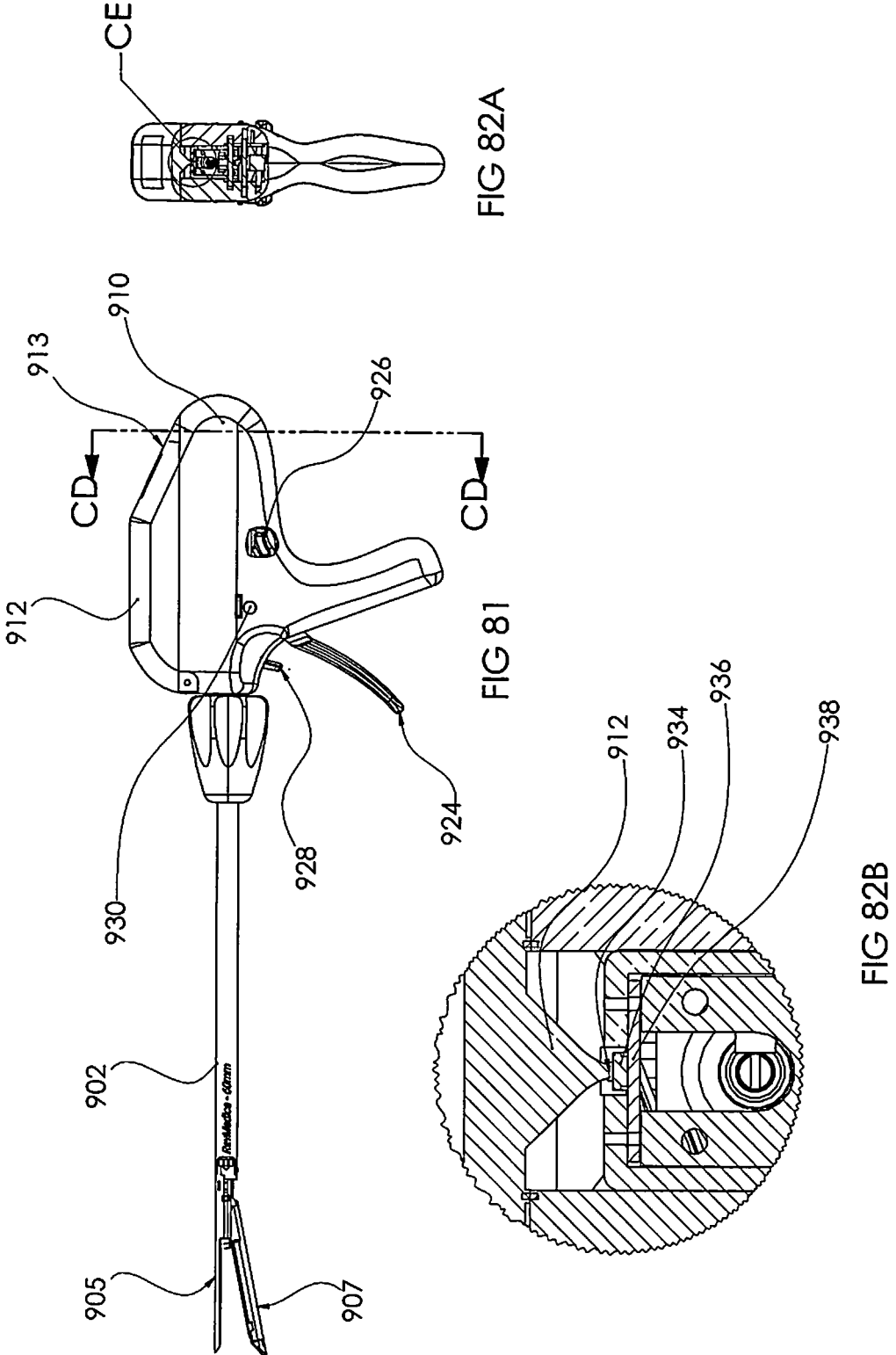

FIG. 55 is a perspective view of an alternate embodiment of the power pack of the present invention;

FIG. 56 is a top view of the power pack of FIG. 55;

FIG. 57A is a cross-sectional view taken along line A-A of FIG. 56;

FIG. 57B is an enlarged view of the area of detail B of FIG. 57A;

FIG. 57C is an enlarged view of the area of detail C of FIG. 57A;

FIG. 58 is a perspective of the deployment (firing) screw assembly of the power pack of FIG. 55;

FIG. 59 is a side view of the assembly of FIG. 58;

FIG. 60A is an enlarged view of the area of detail D of FIG. 59;

FIG. 60B is a cross-sectional view taken along line E-E of FIG. 60A;

FIG. 61A is an enlarged view of the area of detail F of FIG. 59;

FIG. 61B is a cross-sectional view taken along line G-G of FIG. 61A;

FIG. 62A is a cross-sectional view taken along line H-H of FIG. 56;

FIG. 62B is an enlarged view of the area of detail I of FIG. 62A;

FIG. 62C is an enlarged view of the area of detail K of FIG. 62A;

FIG. 63 is a perspective of the articulation screw assembly of the power pack of FIG. 55;

FIG. 64 is a side view of the assembly of FIG. 63;

FIG. 65A is an enlarged view of the area of detail L of FIG. 64;

FIG. 65B is a cross-sectional view taken along line M-M of FIG. 65A;

FIG. 66A is an enlarged view of the area of detail N of FIG. 64;

FIG. 66B is a cross-sectional view taken along line O-O of FIG. 66A;

FIG. 67 is side view of the power pack in accordance with an alternate embodiment of the present invention having an encoder;

FIG. 68 is an exploded view of the deployment screw assembly and encoder of the power pack of FIG. 67;

FIG. 69A is a cross-sectional view taken along line P-P of FIG. 68;

FIG. 69B is an enlarged view of the area of detail Q of FIG. 69A;

FIG. 69C is a cross-sectional view taken along line R-R of FIG. 69A;

FIG. 69D is an enlarged view of the area of detail S of FIG. 69C;

FIG. 70 is a perspective view of the deployment screw assembly and encoder of the power pack of FIG. 67;

FIG. 71 is an enlarged view of the area of detail BK of FIG. 70;

FIG. 72 is a side view of the power pack of FIG. 67 showing section line T-T;

FIG. 73A is a cross-sectional view taken along line T-T of FIG. 72;

FIG. 73B is an enlarged view of the area of detail V of FIG. 73A;

FIG. 74 is side view of the power pack of an alternate embodiment of the present invention having an encoder;

FIG. 75 is a cross-sectional view taken along line W-W of FIG. 74;

FIG. 76A is a cross-sectional view taken along line Y-Y of FIG. 74;

FIG. 76B is an enlarged view of the area of detail X of FIG. 75;

FIG. 76C is an enlarged view of the area of detail Z of FIG. 76A;

FIG. 77 is a perspective view of an alternate embodiment of the surgical instrument of the present invention having a cover to activate a switch of the power pack, the cover shown in an open position;

FIG. 78 is an enlarged view of the area of detail CB of FIG. 77;

FIG. 79 is a top perspective view of the instrument of FIG. 77;

FIG. 80 is an enlarged view of the area of detail CG of FIG. 79;

FIG. 81 is a side view of the surgical instrument of FIG. 77;

FIG. 82A is a rear view of the surgical instrument of FIG. 81; and

FIG. 82B is a cross-sectional view taken along line CD-CD of FIG. 81.

Figure 83:
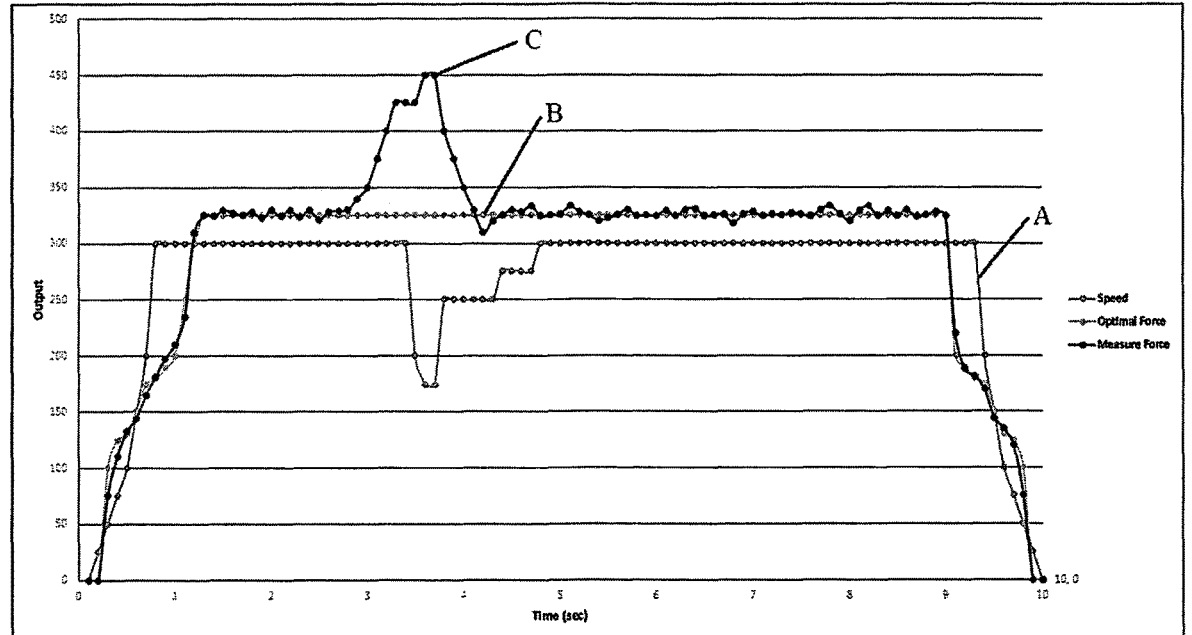

FIG. 83 is a chart depicting the relationship between force and motor speed.

DETAILED DESCRIPTION OF PREFERRED EMBODIMENTS

The present disclosure provides power packs, containing a battery and power train, which are loadable into a surgical stapler to power various functions of the surgical stapler to reduce the forces exerted by the clinician otherwise required if manual force was utilized. The present disclosure also provides surgical staplers designed to receive the power pack and to interact with the power pack to effect firing of the staplers. In some embodiments, the power pack can be used to effect articulation of the jaw assembly of the stapler to pivot the jaw assembly with respect to the longitudinal axis of the stapler. Each of these embodiments is discussed in detail below.

The power pack can also be utilized for powering endoscopic linear staplers, other types of staplers as well as other surgical instruments. Examples of these instruments are also discussed below.

The loadable power packs of the present disclosure are mountable into the handle housing of the surgical instrument, and are maintained in a sterile environment within the surgical instrument so they can be removed and reused. This enables the power pack to be removed from the stapler and reused in another procedure and/or instrument without the complexities, time, costs and risks of resterilization of the power pack. The sealed environment of the battery and power train within the housing also enables certain features/components to be used which might not otherwise be practical if sterilization of the internal power pack was required. Thus, by preventing contact between the power pack and the patient and/or bodily fluids and the external environment, resterilization is not required. The power pack can be used with surgical instruments discarded after use (fully disposable instruments), partially disposable surgical instruments or with fully reusable/sterilizable instruments with the advantage that the power pack need not be discarded or sterilized. Thus, the surgical stapler of the present disclosure advantageously reduces the time, resources and/or costs for preparing the surgical stapler for its next use.

The power packs are easily loadable in the surgical instrument, preferably the handle assembly or housing of the instrument, to easily and securely engage structure in the housing to effect movement of such structure in the instrument. The power packs are also easily disengageable from the structure for removal from the housing for subsequent reuse. The power packs can be configured so they can be loadable and engageable in various types of surgical instruments. The power pack is fully enclosed and sealed by the handle housing so there is no need to sterilize the power pack between uses. The power pack can include a replaceable battery pack so the battery can be changed during a surgical procedure.

In some embodiments the power packs includes sensors, encoders or measurement devices to assess/detect certain functions of the surgical instruments. In some embodiments, automatic adjustments are made via a microprocessor in the power pack to account for such assessment and detection.

Referring now to the drawings and particular embodiments of the present disclosure, wherein like reference numerals identify similar structural features of the devices disclosed herein, there are illustrated several embodiments of the surgical instruments and removable power pack of the present disclosure.

With reference to FIGS. 1-23B, the power pack is used with endoscopic linear staplers which are inserted through trocars and fire linear rows of surgical staples from a cartridge through tissue into contact with an anvil which forms the individual staples. The staplers include an openable compartment in the handle housing that enables easy loading of the power pack within the stapler. The staplers also provide a tight seal to protect the power pack from contaminants so that the power pack does not need to be sterilized for multiple uses.

The power pack is engageable with a staple drive (staple firing) mechanism of the surgical stapler so that once it is loaded in the stapler, actuation of the motor within the power pack effects firing of the staples through tissue. In some embodiments, the power pack is engageable with an articulation mechanism wherein actuation of the motor effects articulation of the stapler. The powered articulation can be in addition to the powered staple firing or alternatively the stapler could have powered articulation and manual staple firing. A specific embodiment of such powered articulation included with powered firing is shown in FIGS. 14A-23B and discussed in detail below.

The term "surgical fasteners" as used herein encompasses staples having legs which are deformed by an anvil, two part fasteners wherein a fastener or staple component with legs is received and retained in a second component (retainer), and other types of fasteners which are advanced through tissue of a patient in performing surgical procedures.

The term "proximal" as used herein denotes the region closer to the user and the term "distal" as used herein denotes the region further from the user. The terms "top" or "upper" and "bottom" or "lower" refer to the orientation of the instruments as shown in the orientation of the instrument in FIG. 2A, with the cover being on the top and the handle extending at the bottom.

Turning first to FIGS. 1-12, a first embodiment of the surgical stapler and removable power pack are illustrated. In this embodiment, the power pack, which contains a battery, motor, drive mechanism and stapler engagement structure, effects firing of the surgical fasteners (staples).

Figures 1, 2A, 2B, 2C:
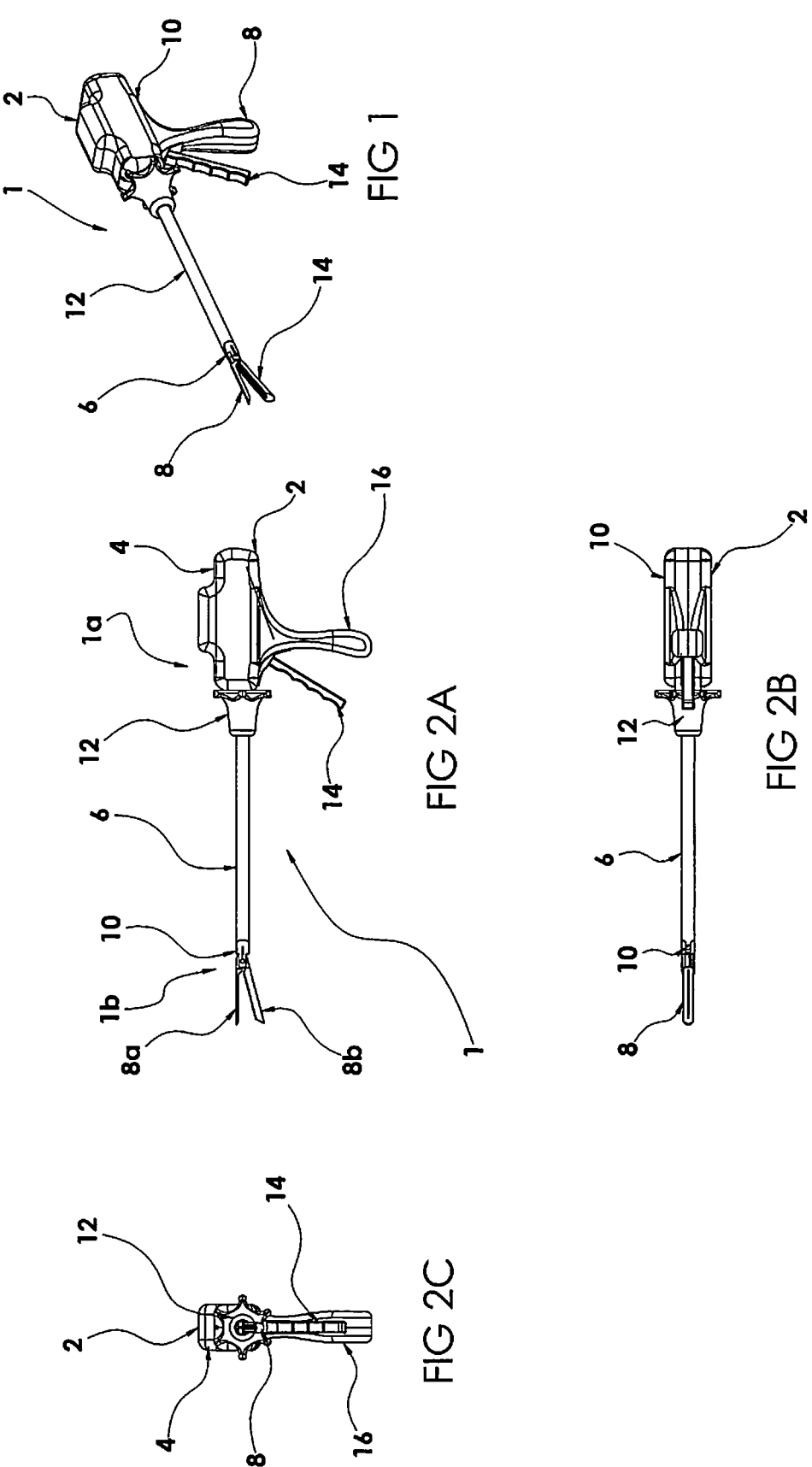
FIG. 1 is a perspective view of a first embodiment of the surgical stapler of the present disclosure having a removable power pack.
FIG. 2A is a side view of the surgical stapler of FIG. 1.
FIG. 2B is a bottom view of the surgical stapler of FIG. 1.
FIG. 2C is a front view of the surgical stapler of FIG. 1A.

The surgical stapler, also referred to herein as the or surgical fastener applying instrument or surgical fastener applier, is designated generally by reference numeral 1 and includes a proximal portion 1*a*, a distal portion 1*b* and an elongated or endoscopic portion 6 (also referred to as an elongated tubular portion or shaft) extending between the proximal portion 1*a* and the distal portion 1*b*. A handle assembly 2 with a housing 4 (also referred to herein as a handle housing) is positioned at the proximal portion 1*a* and is configured to house and protect internal mechanisms of the stapler including the removable power pack when loaded (mounted) therein. At the distal portion 1*b* are opposing members, i.e., jaws, 8*a*, 8*b*, configured to clamp and constrain tissue during operation of the surgical stapler. At least one of the jaws is movable with respect to the other jaw from an open position to receive tissue between the jaws and a closed position to clamp tissue between the jaws. Thus, one of the jaws can be stationary and the other jaw movable with respect to the stationary jaw or alternatively both jaws can move, e.g., pivot, toward each other. In the embodiment of FIG. 1, jaw 8*b*, which contains at least one row of surgical fasteners (staples) is movable with respect to non-pivoting (stationary) jaw 8*a* which contains an anvil with staple forming pockets. Jaws 8*a*, 8*b* are collectively referred to herein as jaws 8. The fasteners are fired (advanced) from jaw 8*b* by linear movement of a firing mechanism which engages staple drivers within the jaw 8*b* which move transverse to the longitudinal axis, i.e., transverse to the direction of movement of the firing mechanism, to sequentially advance (from proximal to distal) the staples in the linear rows of staples from the jaw 8*b* and through tissue to engage the anvil pockets on jaws 8*a* for formation of the staples. Such firing of the staples is illustrated in FIG. 7C and discussed below.

The elongated tubular member 6 extends distally from the housing 4 and is configured to fit through a surgical port (trocar) used for laparoscopic surgery. The endoscopic portion 6 can be of varying dimensions and in some embodiments is configured to fit through a 10 mm trocar, although other dimensions for fitting through other size trocars are also contemplated such as trocars ranging from 5 mm to 15 mm. It is advantageous to minimize the diameter of the endoscopic portion to minimize the size of the patient's incision. With the jaws 8 in the clamped position, the outer diameter of the elongated member 6 is maintained as the cross-sectional dimension of the closed jaws 8 preferably does not exceed the cross-sectional dimension (i.e., diameter) of the tubular member 6.

The surgical stapler 1 can in some embodiments include a joint 10 that provides for the articulation of the opposing members 8, i.e., pivoting of the jaw assembly (jaws 8) to angular positions with respect to the longitudinal axis of elongated member 6. Articulation can be achieved by linear motion of elongated members extending through the endoscopic portion 6 which are slidable to angle the jaw assembly. A rotational member or knob 12 is configured to rotate, with respect to the handle assembly, the elongated member 6 and connected jaws 8 about the axis of the elongated member 6 to change the position of the jaws 8. Articulation is effected by manual manipulation of a lever adjacent the handle 2. A handle lever 14, linked to an axially movable clamping bar, is pivotable from a first position to a second position closer to stationary handle 16 to effect movement of the jaw 8*b* toward the jaw 8*a* from an open (unclamped) position to a clamping position, also referred to as a closed position of the jaws 8. Release of handle lever 14 returns the jaw 8*b* to its open position. Stationary handle 16 for grasping by the user is ergonomically designed for comfort of use. In summary, the surgical stapler operates by manual pivoting of the lever 14 toward stationary handle 16 to clamp the tissue between jaws 8, followed by powered firing of the staples from jaw 8*b*, through the clamped tissue and into contact with the staple forming pockets of the anvil of jaw 8*b*. Prior to firing, the jaws 8 can be rotated to a desired orientation by rotation of endoscopic portion 6 via knob 12 and/or articulated about joint 10, via movement of the elongated articulation members, to a desired angled position with respect to the longitudinal axis of endoscopic portion 6. In the embodiment of FIG. 1, articulation is performed by manual manipulation of a lever (not shown) which is operatively connected to an internal elongated member within tubular member 6 which extends to joint 10. A force applied to the internal elongated member pivots/articulates the jaws 8 about the joint 10. In later described embodiments (FIG. 14A), powered articulation is provided.

Figures 3A, 3B, 3C:
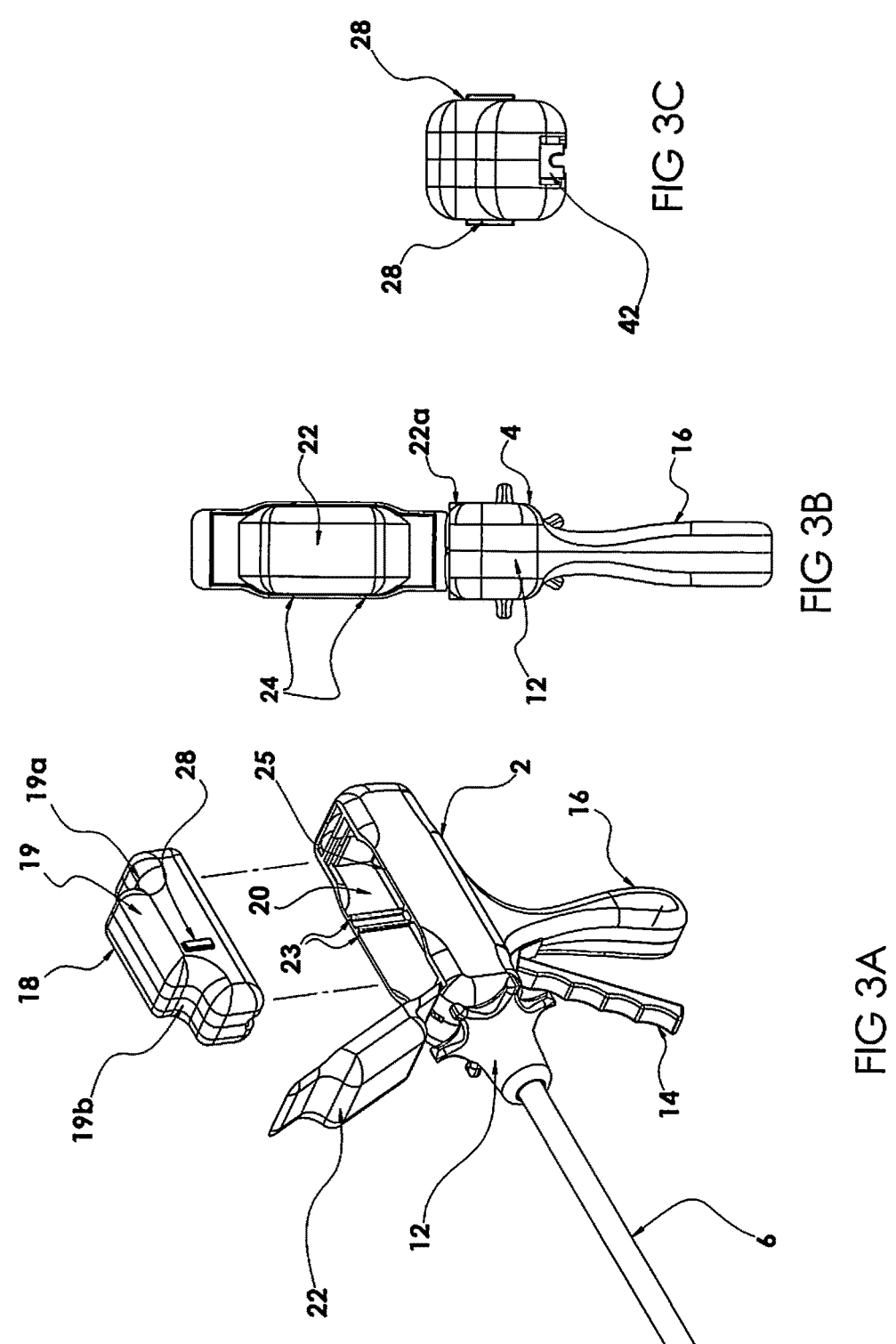
FIG. 3A is a perspective view of the surgical stapler of FIG. 1 showing the handle compartment cover in the open position and further showing the power pack prior to insertion into the handle compartment.
FIG. 3B is front view of the surgical stapler of FIG. 3A showing the handle compartment cover in the open position.
FIG. 3C is a front view of the power pack of FIG. 3A.
Figure 3D:
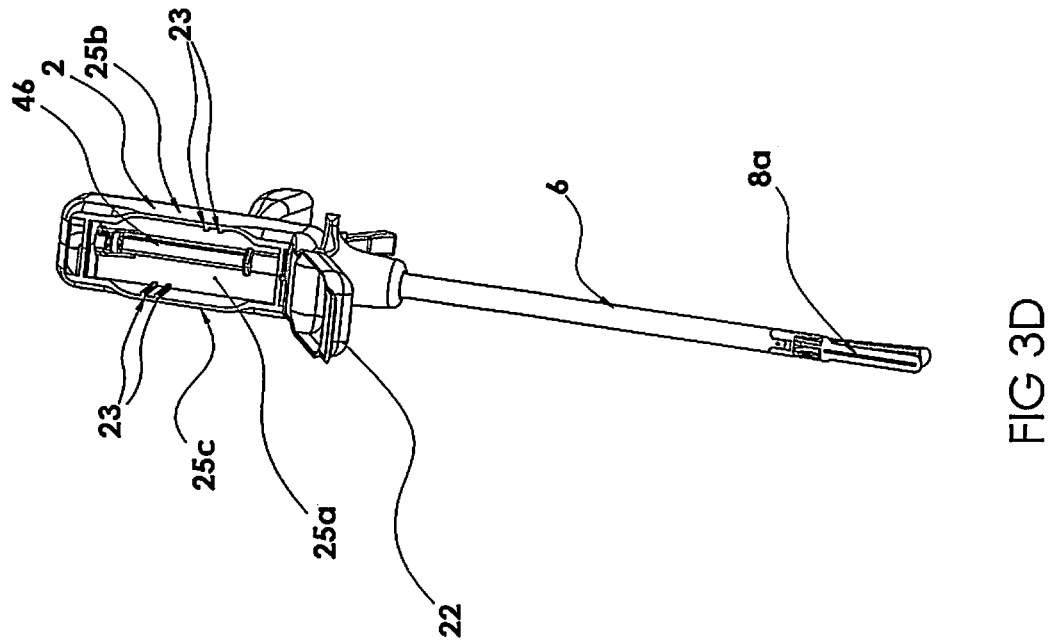
FIG. 3D is a top perspective view of the surgical staple of FIG. 3A showing the compartment for receiving the power pack.

The housing 4 of the handle assembly 2 of the surgical stapler is configured to receive the loadable/removable power pack 18 in a receptacle (compartment) 20 as shown in FIGS. 3A and 3D. The receptacle includes a base 25*a* and side walls 25*b* and 25*c* having one or more guides 23 that cooperate with corresponding guiding structures 28 on the outer wall of the housing 19 of power pack 18 for proper alignment of the power pack 18 in the handle assembly 2 during insertion into the receptacle 20. In the embodiment of FIG. 3A, the guides 28 on power pack housing 19 are in the form of a pair of ribs or projections 28 extending transversely to a longitudinal axis of the power pack 18 for receipt within grooves formed between guides, e.g., ribs or projections, 23 of the compartment 20, also extending transversely with respect to a longitudinal axis of the stapler 1. In the illustrated embodiment, the ribs 23 are on opposing sides of the power pack 18 and are axially offset from each other, although in alternate embodiments they can be axially aligned. Additionally, a different number of ribs (axially or non-axially aligned) can be provided (with corresponding receiving structure in the compartment 20). It should be appreciated that alternatively, the grooves could be provided on the power pack 18 and the ribs provided in the compartment 20 to provide the guiding structure for the power pack 18. The guiding structure also helps to retain power pack 18 in position within the compartment 20. The power pack 18 has front and rear concave regions 19*a*, 19*b* to reduce its overall size.

The handle assembly 2 includes a cover 22 for opening and closing the receptacle 20. The compartment cover 22 is shown as being hingedly attached to the housing 4, but may alternatively be fully removable or attached in some other manner such as a slidable connection or the like. The cover 22 is shown pivotable mounted to a top portion of the housing 4 (in the orientation of FIG. 2A) for top loading of the power pack, although alternatively, side or bottom loading can be provided. The cover 22 is shown pivotable from a closed position of FIG. 2A to an open position of FIG. 3A to enable loading of power pack into the compartment 20 of the housing 4. In some embodiments, the cover 20 is spring loaded to an open position so it remains open for loading of the power pack 18. Once loaded, the cover 22 is pivoted about hinge 22*a* to its closed position. A latch can be provided to latch the cover 22 to the housing 4 in the closed position. When the cover 22 is in an open position, e.g., as shown in FIG. 3A, the power pack 18 may be removed from the receptacle 20 or inserted into the receptacle 20.

When the cover 22 is in a closed position, the seal of the cover 22 is in contact with the rim of the housing 2 such that the receptacle 20, and the power pack 18 if inserted into receptacle 20, is sealed from the environment exterior to the surgical stapler. The top seal 24 can be attached to the cover 22 and in some embodiments can be in the form of an elastomer that is compressed by the housing, e.g., tightly fits slightly within the housing or is pressed on the rim of the housing 2. In other embodiments, the elastomer seal 24 can be on the housing 2, i.e., extending around the perimeter of the rim of the compartment 20, and is compressed by the cover 22 to seal between the cover 22 and housing 4. Other seals can also be provided within the surgical stapler to seal/protect the power pack 18 from contaminants, e.g., body fluids. These seals are discussed in more detail below.

Turning now to the power pack of the present disclosure, and with reference to FIGS. 4A-4I, the power pack 18 includes a motor assembly, battery and electronics contained within housing 19. More specifically, as shown in FIGS. 4A-4E, the power pack 18 includes a powering assembly including a motor 32 connected to a planetary gear box 34 configured to gear down the output of the motor 32 for proper drive speeds for firing staples from jaw 8b through the tissue into contact with the anvil of jaw 8a. The planetary gear box 34 drives a lead screw 36 through one or more gears operatively connected to the motor shaft. More specifically, upon rotation of the motor shaft by motor 32 in a first direction, gear 38 is rotated in the same first direction, causing rotation of the gear 30 in a second opposite direction due to the intermeshed teeth of gears 30 and 38. Lead screw 36 is operatively connected to gear 30 so that rotation of gear 30 causes rotation of lead screw 30 in the same direction. The power pack 18 includes a battery 33 which can be rechargeable outside the stapler when the power pack 18 is removed. The power pack 18 in some embodiments can include a power switch which is activated, i.e., turned on, by the clinician to start the motor and effect staple firing. In other embodiments, the motor can automatically turn on when the power pack is fully loaded or upon actuation of another control on the stapler housing 4. In some embodiments, the motor can automatically turn off when the power pack is removed from the stapler housing.

Connected to the end of lead screw 36 (the end opposite the connection to the gear 30) is a drive mechanism 40. The drive mechanism 40 is configured to move in a linear motion (in an axial direction) along the lead screw 36 in response to rotation of the lead screw 36. For example, the drive mechanism 40 may include internal threads that engage external threads of the lead screw 36 and may include slides engaged in a track that prevent the drive mechanism 40 from rotating and therefore cause the drive mechanism 40 to move linearly (axially) in response to rotation of the lead screw 36. As depicted in FIGS. 4A-4G, the power pack 18 has a compact configuration as the lead screw 36 extends alongside, slightly spaced from, the motor 32 and gear box 34, i.e., both the motor 32/gear box 34 and lead screw 36 extending longitudinally with the lead screw 36 parallel to the motor 32. The drive mechanism 40 is connected to a proximal end of lead screw 36 and extends proximally of the proximal end of the motor 32 in the illustrated embodiment.

Figures 4A, 4B, 4C, 4D, 4E, 4F:
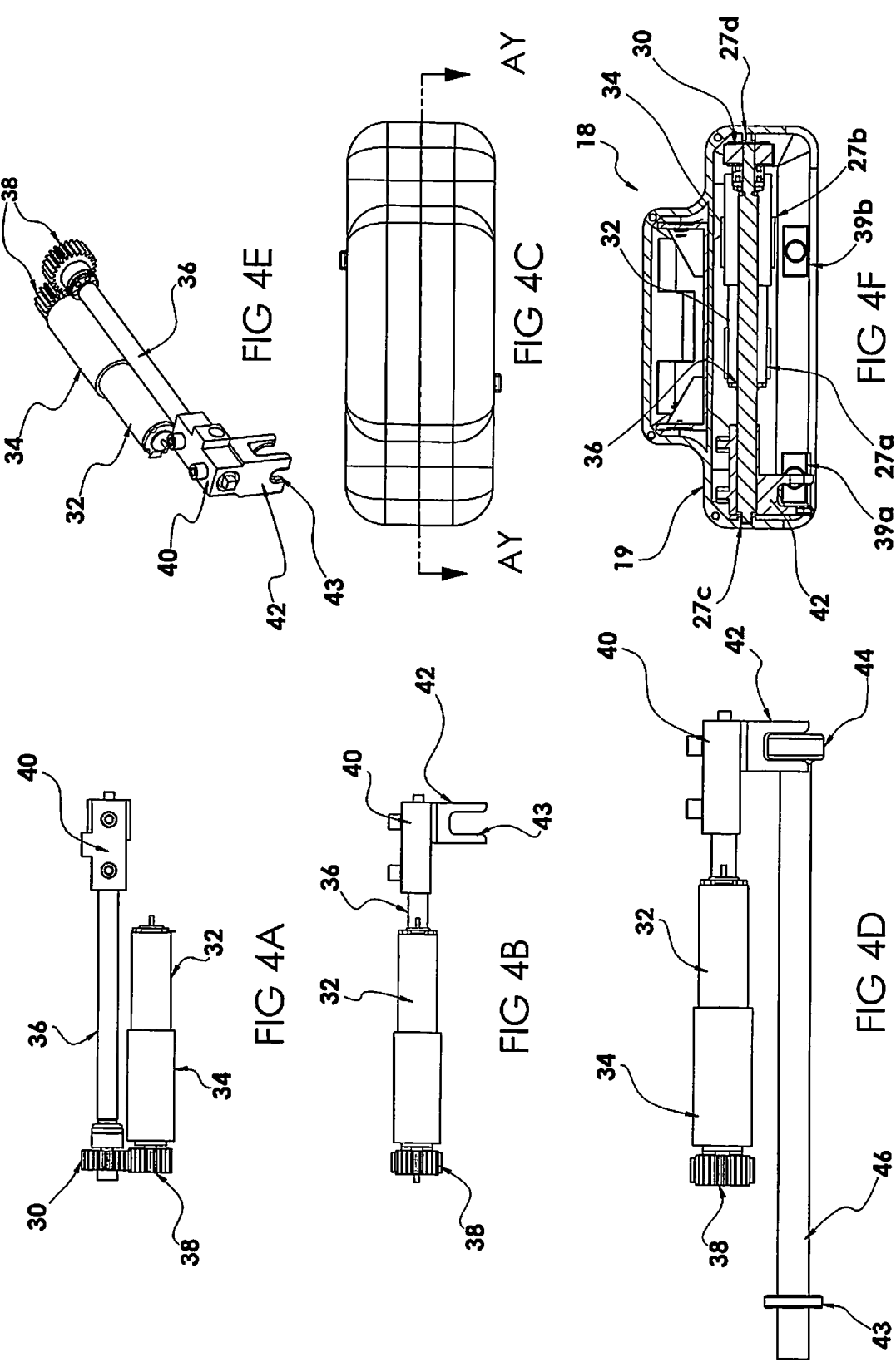
FIG. 4A is a top view of the motor and drive mechanism (assembly) of the power pack of FIG. 3A.
FIG. 4B is a side view of the motor and drive mechanism of the power pack of FIG. 4A.
FIG. 4C is a top view of the power pack of FIG. 3A.
FIG. 4D is a side view of the motor and drive mechanism of FIG. 4A shown engaged with the rod of the firing assembly of the surgical stapler of FIG. 1.
FIG. 4E is a perspective view of the motor and drive mechanism of the power pack of FIG. 3A.
FIG. 4F is a cross-sectional view taken along line AY-AY of FIG. 4C showing the power pack engaging the firing rod of the surgical stapler of FIG. 1.

The power pack 18 can have features/structure to constrain the motor 32. In the embodiment of FIG. 4F, such feature is in the form of proximal rails 27a and distal rails 27b spaced apart axially within the housing 19. Motor 32 is seated within proximal rails 27a and gear box 34 is seated within rails 27b, the rails 27a, 27b retaining the motor and preventing axial and rotational movement within the housing 19. Bearing or bushings 27c and 27d can also be provided to constrain the lead screw 36 at opposing ends, while allowing rotation thereof, thereby also constraining the motor. Other features can additionally or alternatively be provided to restrain the motor from axial movement while allowing rotation of the lead screw.

The drive mechanism 40 includes a first output flag or yoke 42, which is discussed in more detail below, configured to engage a staple firing mechanism, e.g., firing rod 46, extending longitudinally within the handle 4. The staple firing rod 46 is operatively connected to a firing rod in the endoscopic portion 6 which is operatively engageable with a series of staple drivers in jaw 8b to advance the fasteners (staples) from the fastener jaw 8b. Alternatively, the firing rod 46 can extend through the endoscopic portion 6 and itself engage the stapler drivers as shown in FIG. 7C. Thus, as the motor 32 generates rotational motion of the lead screw 36 through the planetary gear box 34 and the gears 38, 30, the drive mechanism 40 moves in linear motion along the lead screw 36. Such linear motion effects linear movement of the firing rod 46 (due to the engagement by the flag 42) which advances the staple driving mechanism to advance (fire) the staples out from jaw 8b through tissue and into contact with the anvil in jaw 8a. As noted above, the firing rod 46 can be a single element extending through the endoscopic portion 6 (see e.g., FIG. 7C) and terminating adjacent jaws 8 or alternatively can be attached to one or more components intermediate the firing rod 46 and jaws 8. In FIG. 7C, camming surface 46a of firing rod 46 engages staple drivers 47 to sequentially fire staples 51 as the firing rod 46 is advanced.

The power pack 18 can also include in some embodiments one or more sensors to indicate the position of the firing rod 46 to indicate to the clinician the status of staple firing. The embodiment of FIG. 4F illustrates an example of such sensors if they are provided. The power pack 18 has within the housing a proximal sensor 39a and a distal sensor 39b to sense the position of yoke 42 of the drive mechanism 40. Thus, sensor 39a senses the initial position of the yoke 42 (and thus the initial position of the firing rod 46) and at the end of the firing stroke, sensor 39b would indicate the end (final) position of the yoke 42 (and thus the final positon of the firing rod 46) which would indicate completed firing of the fasteners. The power pack 18 could also include an audible or visual indicator (viewable though the power pack housing 19 and instrument handle housing 4) actuated by the sensor to indicate to the clinician the position of the flag 42 and thus the completion or status of the firing stroke to fire the fasteners. The power pack 19 can also include sensors to detect the position of the articulation flag in the embodiments discussed below which have powered articulation. The sensor can include a potentiometer to determine the location during the firing stroke. It can also include an encoder to detect the position along the stroke. Alternatively, the stroke can also be identified by motor count. The power pack 18 in all other respects is identical to power pack 18 of FIG. 3A.

It is also contemplated that in alternate embodiments, the sensor(s) can be carried by the handle housing rather than (or in addition to) the power pack and utilized to detect the positioning of the flag 42 and/or firing rod 46 and/or detect the position of the articulation flag and/or articulation rod in the embodiments discussed below which have powered articulation.

It is also contemplated that a sensor(s) can be provided to detect the position of the clamping rod for clamping the jaws. The sensor can be provided in (or supported by) the power pack or alternatively the sensor(s) can be carried by the handle housing rather than (or in addition to) the power pack and utilized to detect the positioning of the jaws by detecting the position of the flag engaging the jaw clamping rod and/or detecting the position of the jaw clamping rod in the embodiments which have powered clamping.

Note the sensor can be provided in some embodiments; in other embodiments, no sensor is provided.

The power pack in some embodiments has a battery pack that is removably mounted in or on the power pack. This is discussed in more detail in conjunction with FIGS. 35-37C.

Turning now to the loading of the power pack 18 into the surgical stapler 1, as seen in FIGS. 6A-6D, the power pack 18 is in the process of being inserted into the receptacle 20 of housing 4. As shown, handle compartment cover 22 is open to provide access to compartment 20. The output flag 42 of the power pack 18 as noted above is driven by the motor assembly and is configured to engage and interact with structure within the handle assembly 2, e.g., firing rod 46, to control operation of the surgical stapler 1 when the power pack 18 is fully inserted into the receptacle 20. As can be appreciated in FIG. 6D, the output flag 42 is not fully engaged with the flange 44 of the firing rod 46. Also shown in FIG. 6D is the clamp bar 49 which is positioned within and concentric with firing rod 46. The clamp bar 49 is operatively connected to the pivotable handle 14 of stapler 1 via linkage 14*a* (pin 14*b* connects one end of handle 14 to the distal end of clamp bar 49). In this manner, movement of pivotable handle 14 toward stationary handle 16 causes the operatively connected jaw clamping mechanism, e.g., clamp rod 49, to be advanced distally to pivot jaw 8*b* toward jaw 8*a* to clamp tissue between the two jaws 8. Note that for clamping, clamp bar 49 slides linearly within a lumen of firing rod 46; for staple firing, firing rod 46 moves linearly over clamp bar 49.

The output flag 42 of power pack 18 is configured to engage a bossed end 44 of the firing rod 46 when the power pack 18 is fully inserted into the receptacle 20 of the handle assembly 2. As shown, the output flag (yoke) 42 has a receiving or mounting feature or member (also referred to as the engagement feature (member) or firing rod engagement feature (member) in the form of two arms 43*a* and a slot 43*b* therebetween, configured to frictionally (and releasably) engage the bossed end 44, the feature aligning with the bossed end 44 during insertion. (The aforedescribed guiding structure on the power pack 18 and internal wall of the compartment 20 aid such alignment).

FIGS. 8A, 8B and 10 show the power pack 18 fully inserted into the compartment 20 of stapler 1. In this position, the output flag 42 is engaged with the bossed end 44 of the firing rod 46. Note the firing rod 46 is able to rotate when the first output flag 42 of the power pack 18 is engaged with the bossed end 44. When the power pack 18 is secured to the firing rod 46 by the first output flag 42, linear motion generated at the first output flag 42 by the motor actuated drive assembly is transferred to the firing rod 46, which moves linearly to actuate the staple firing mechanism. That is, rotation of the gear 30 effects axial (linear) movement of the drive screw 36 which effects axial (linear) movement of the connected drive mechanism 40 to effect axial (linear) movement of the associated drive mechanism (rod) engaging member (i.e., flag 42). It should be appreciated that flag 42 provides one example of the releasable attachment (engagement member) of the motor assembly to the firing rod 46, it being understood that other mounting (engagement) members or features are also contemplated to engage the firing rod to advance it axially.

In use, the cover 22 of stapler 1 is opened and the power pack 18 is inserted into receptacle 20 of sterile handle assembly 2 (of sterile stapler 1), with the output flag 42 of the power pack 18 engaging a corresponding feature, e.g., boss 44 of elongated drive rod 46, in the handle assembly 2 as discussed above. Then, the cover 22 is closed to seal the power pack 18 within the receptacle 20 from the external environment and the surgical stapler 1 may be actuated, i.e., manually clamped, articulated and/or rotated if desired, and the motor actuated to effect staple firing. After applications of fasteners and release (unclamping of the jaws from tissue), the cover 22 can be opened and the power pack 18 removed and charged while the stapler and handle assembly are resterilized if the stapler is a reusable instrument or the stapler and handle assembly are disposed of if the stapler is a single use disposable instrument. The power pack 18, due to its sealed configuration discussed above, can be reused without requiring sterilization by insertion into the receptacle 20 of a resterilized handle assembly or a sterile handle assembly of an unused disposable handle assembly. Thus, as can be appreciated, the removable power pack 18 does not need to be subjected to the sterilization process and, therefore, contact between the harsh temperatures and/or chemicals of the sterilization process is advantageously avoided. Also, by being able to reuse the power pack without sterilization, significant cost savings are achieved compared to if the power pack is not resterilizable, is disposed of along with the disposable stapler.

Note that in the embodiment of FIGS. 1-12 (and FIGS. 14-23B discussed below), rotational motion caused by the motor is translated into linear motion. This is shown schematically in FIG. 5A wherein the drive rod in the handle housing is engaged by the motor driven drive assembly of the power pack 18 (or power pack 90 which is discussed below) moves linearly (axially) to effect linear (axial) movement of the drive member in the stapler, e.g., extending through the endoscopic portion, which effects staple firing. Alternatively, or in addition, a drive assembly of the power pack engages a drive rod in the housing which moves linearly to effect linear movement of a drive rod to effect clamping of the jaws and/or a drive assembly of the power pack engages a drive rod in the housing which moves linearly to effect linear movement of a drive member to effect articulation of the jaw assembly. Alternatively, the intermediate drive member could be omitted and the drive rods directly effect respective clamping and articulation.

Figures 5A, 5B:
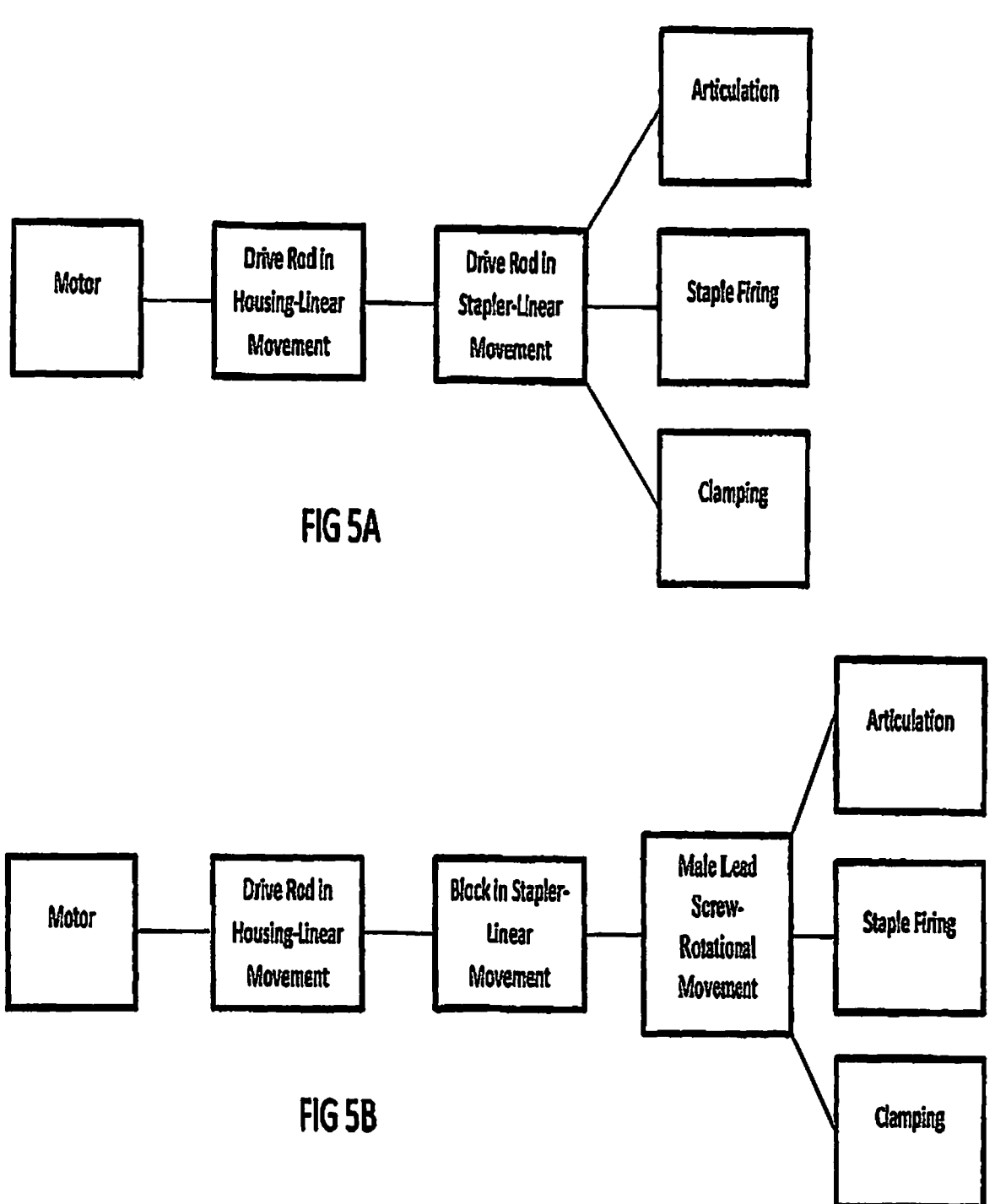
FIG. 5A is a schematic view illustrating transition from rotational movement to linear movement to effect a function of the surgical stapler.
FIG. 5B is a schematic view of an alternate embodiment illustrating transition from rotational movement to linear movement to rotational movement to effect a function of the surgical stapler.
Figures 8C, 8D, 12:
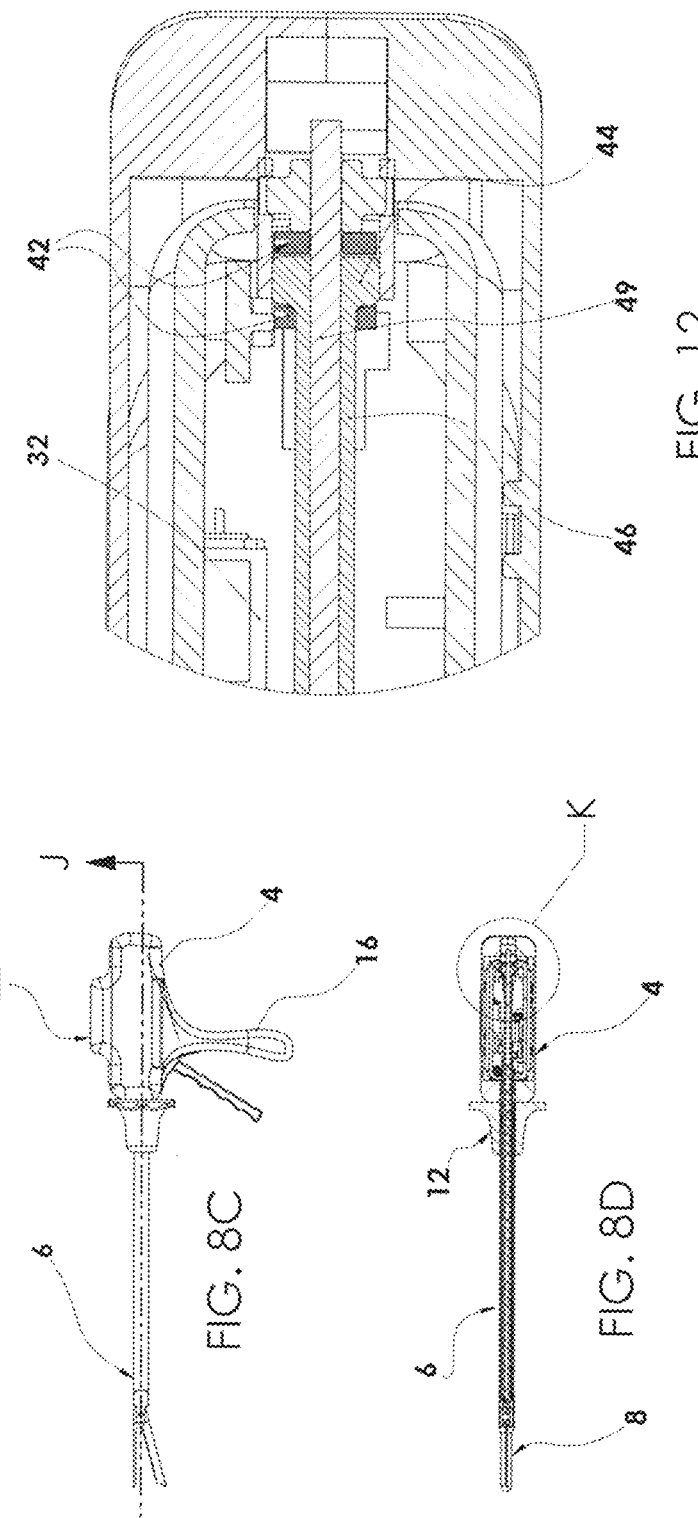
FIG. 8C is a side view of the surgical stapler of FIG. 1 showing the power pack fully inserted in the handle compartment and the compartment cover closed.
FIG. 8D is a cross-sectional view taken along line J-J of FIG. 8C.
FIG. 12 is a close up view of the detail K of FIG. 8D.

In an alternate embodiment, shown schematically in FIG. 5B, linear motion is converted back to rotational movement. That is, the handle housing has a receptacle (compartment) to receive power pack 18 (or power pack 90) which has one or more engagement features to engage or couple to a firing rod for firing staples, a clamping rod for clamping the jaws about tissue and/or an articulation rod to articulate the jaws to angular positions with respect to the longitudinal axis. The drive rod is connected at its distal end to a block in the stapler having a female thread or a slotted guide engagement to prevent rotation of the block and enable linear movement. (The drive rod could alternatively be attached to other structure). The block is connected to a male lead screw which is engaged at its proximal end via threaded engagement to the distal end of the block. The lead screw is connected at its distal end to a component that requires rotation to effect operation of the stapler, such as effecting staple firing, clamping and/or articulation. A bearing can be provided to keep the lead screw on center and control axial motion. In use, actuation of the motor advances the drive assembly of the power pack linearly which is engaged with and advances the drive rod in the handle housing linearly (axially). Linear movement of the drive rod causes linear movement of the block positioned in the endoscopic portion (or alternatively positioned in the handle housing.) Linear movement of the block causes rotation of the male lead screw to engage a staple firing component(s) to effect staple firing. Alternatively, or in addition, the drive assembly, or a separate drive assembly (assemblies), engages a drive rod in the housing which moves linearly to effect linear movement of a block to cause rotation of the lead screw to move a jaw clamping component(s) to effect clamping of the jaws and/or engages a drive rod in the housing which moves linearly to effect linear movement of a block to cause rotation of the lead screw to move an articulation component(s) to effect articulation of the jaws.

In the embodiment of FIGS. 1-12, the power pack 18 actuates the firing rod 46 to fire the staples while other steps are performed manually. In summary, in this embodiment, in use, the jaws 8*a*, 8*b* are moved to the closed (clamped) position manually by a hand actuated lever or control. Also, in this embodiment, the jaws 8 are articulated with respect to the longitudinal axis of the endoscopic portion manually by a hand actuated lever or control. Thus, the clinician would manually clamp the jaws, manually rotate the endoscopic portion and attached jaws 8, and manually articulate the jaws by manipulation of controls at the proximal end of the stapler 1, e.g., at the handle 4.

Figures 13A, 13B:
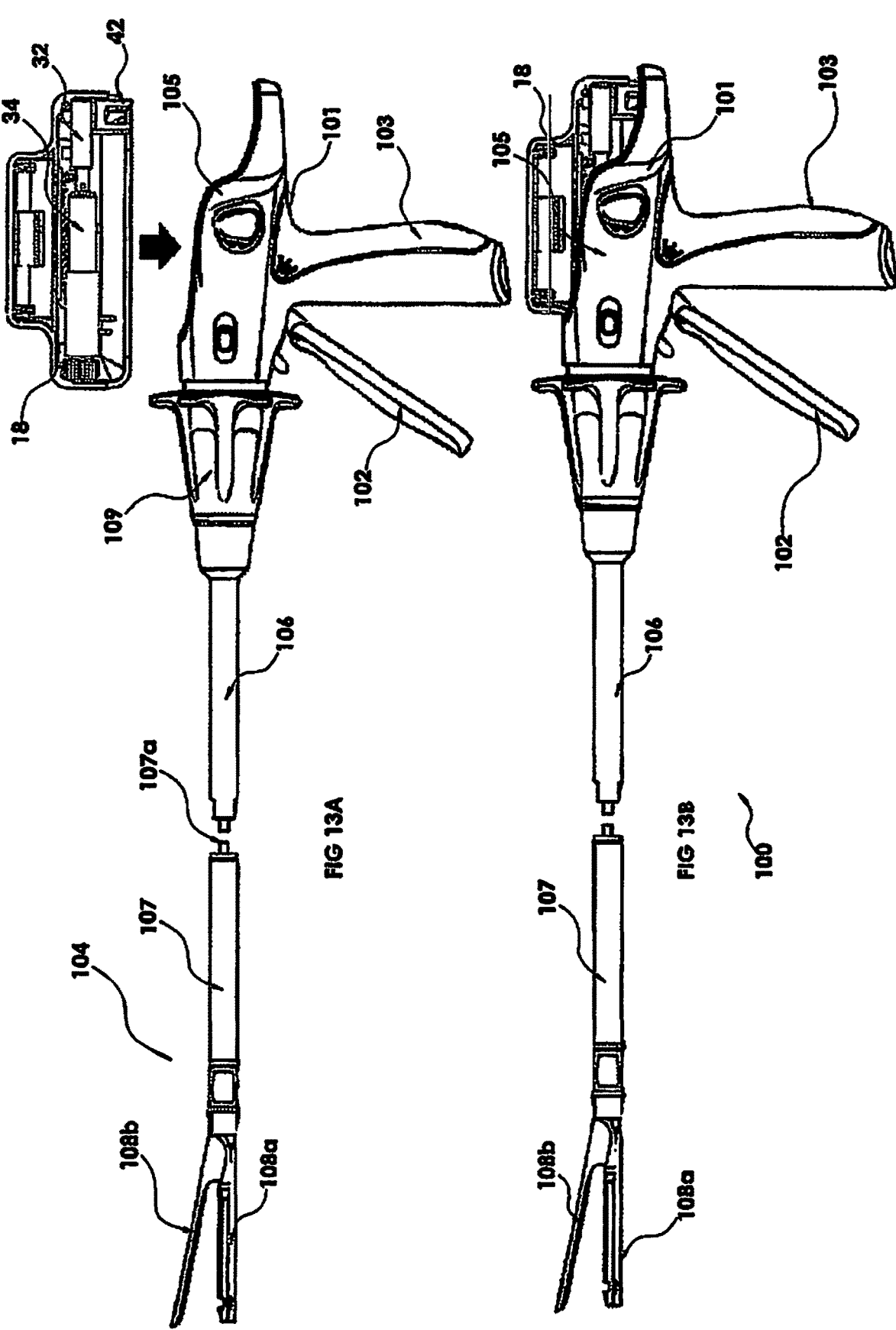
FIG. 13A is a side view of an alternate embodiment of the surgical stapler showing the power pack of FIG. 3A prior to insertion into the handle compartment.
FIG. 13B is a side view similar to FIG. 13A showing the power pack of FIG. 3A inserted into the handle compartment.

FIGS. 1-12 show one embodiment of an endoscopic linear stapler that can be used with the power pack 19 of the present disclosure. However, the power pack 18 is not limited to such endoscopic staplers. For example, FIGS. 13A and 13B illustrate another endoscopic linear stapler, designated by reference numeral 100, that can be powered by power pack 18. Stapler 100 has a handle 102 manually pivotable towards stationary handle 103 for clamping of the jaws 108a, 108b, an endoscopic portion 106 extending from the handle housing 101, a jaw assembly 104 containing jaws 108a, 108b and connector 107a extending proximally from shaft or tube 107 for attachment to the endoscopic portion 106 so that the jaw assembly 104 can be replaced multiple times in a single surgical procedure to provide additional rows of staples to tissue. The stapler 100 also includes a rotation knob 109 for rotation of the endoscopic portion 106, with respect to the handle housing, to rotate the attached jaws 108a, 108b. The stapler 100 can also include an articulation knob to articulate the jaws. Power pack 18 is shown in FIG. 13A prior to loading within the handle housing 101 and shown in FIG. 13B fully loaded (inserted) within the handle housing 101. A cover (not shown) can be provided to seal the power pack 18 from the external environment. As in the embodiment of FIGS. 1-12, the flag 42 extending from lead screw 36 engages a firing rod within the handle housing 101 to effect movement of a firing rod to fire the staples when the motor of the power pack 18 is actuated. Power pack 90 having articulation described below can also be utilized with stapler 100.

Figures 13C, 13D:
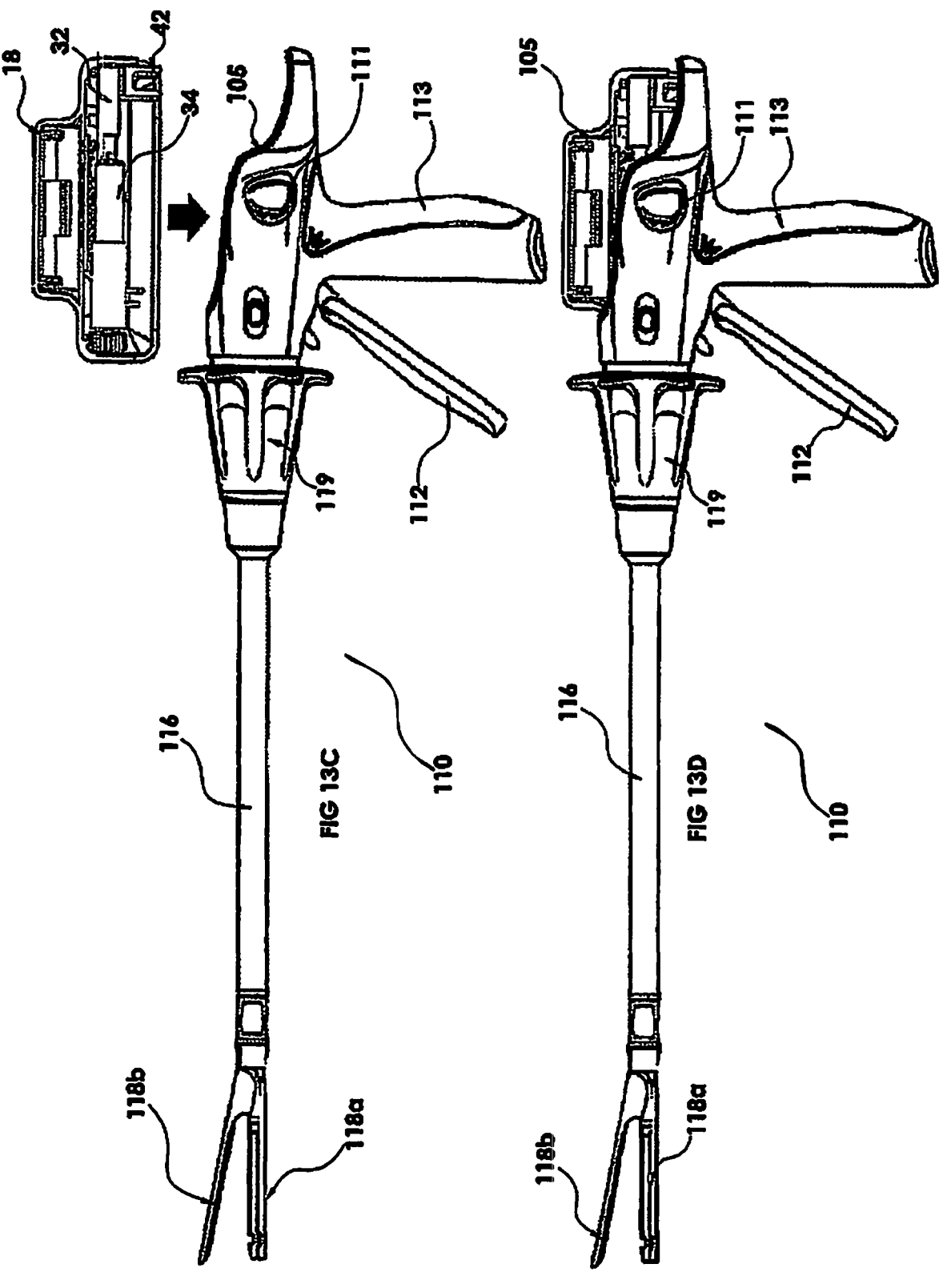
FIG. 13C is a side view of another alternate embodiment of the surgical stapler showing the power pack of FIG. 3A prior to insertion into the handle compartment.
FIG. 13D is a side view similar to FIG. 13C showing the power pack of FIG. 3A inserted into the handle compartment.
Figures 14D, 14E, 14F, 15B:
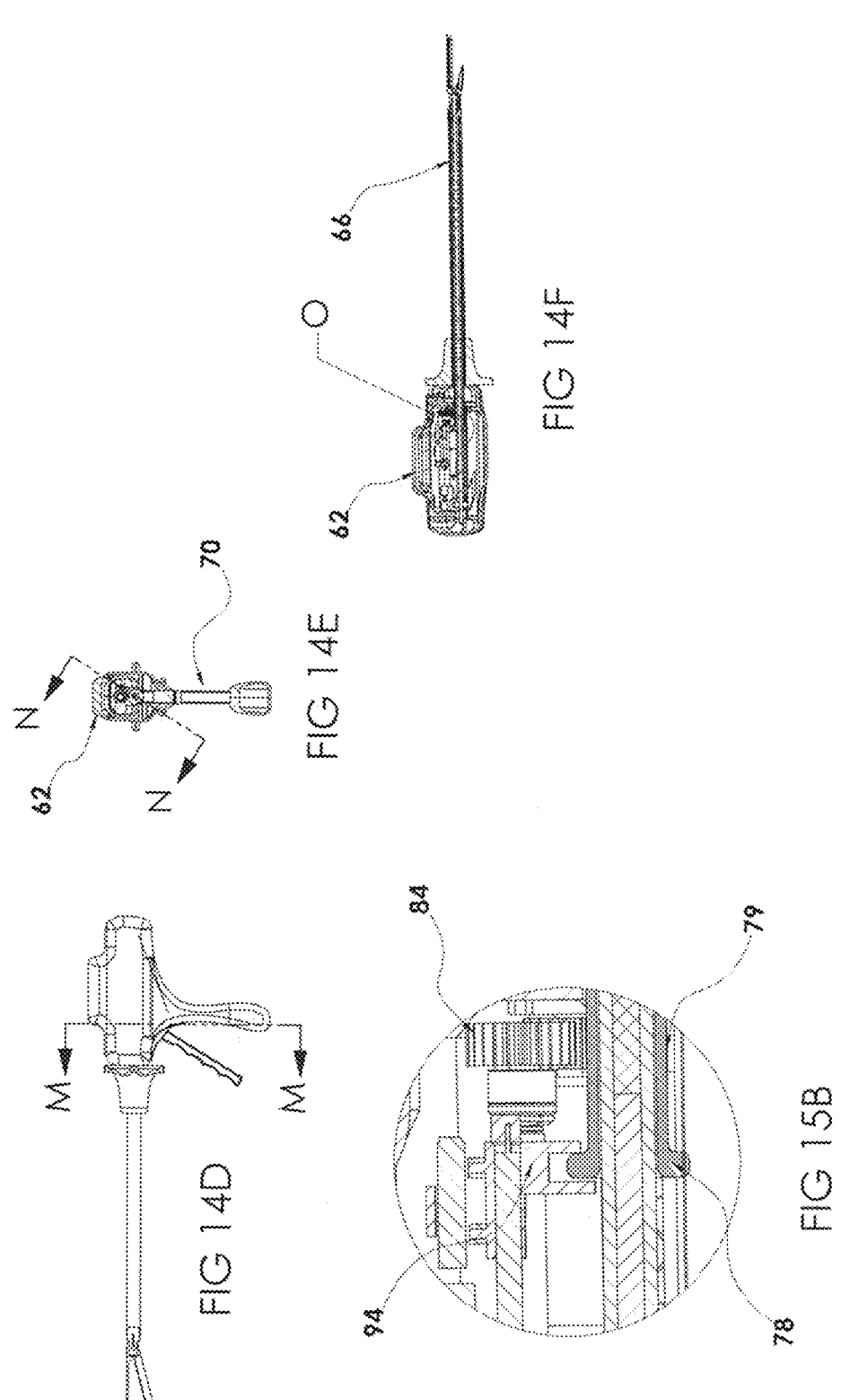
FIG. 14D is a side view of the surgical stapler of FIG. 14A, the view being the same as FIG. 14A but having section line M-M.
FIG. 14E is cross-sectional view taken along line M-M of FIG. 14D.
FIG. 14F is a cross-sectional view taken along line N-N of FIG. 14D.
FIG. 15B is a close up view of the area of detail O of FIG. 14E.
Figures 17, 18A, 18B:
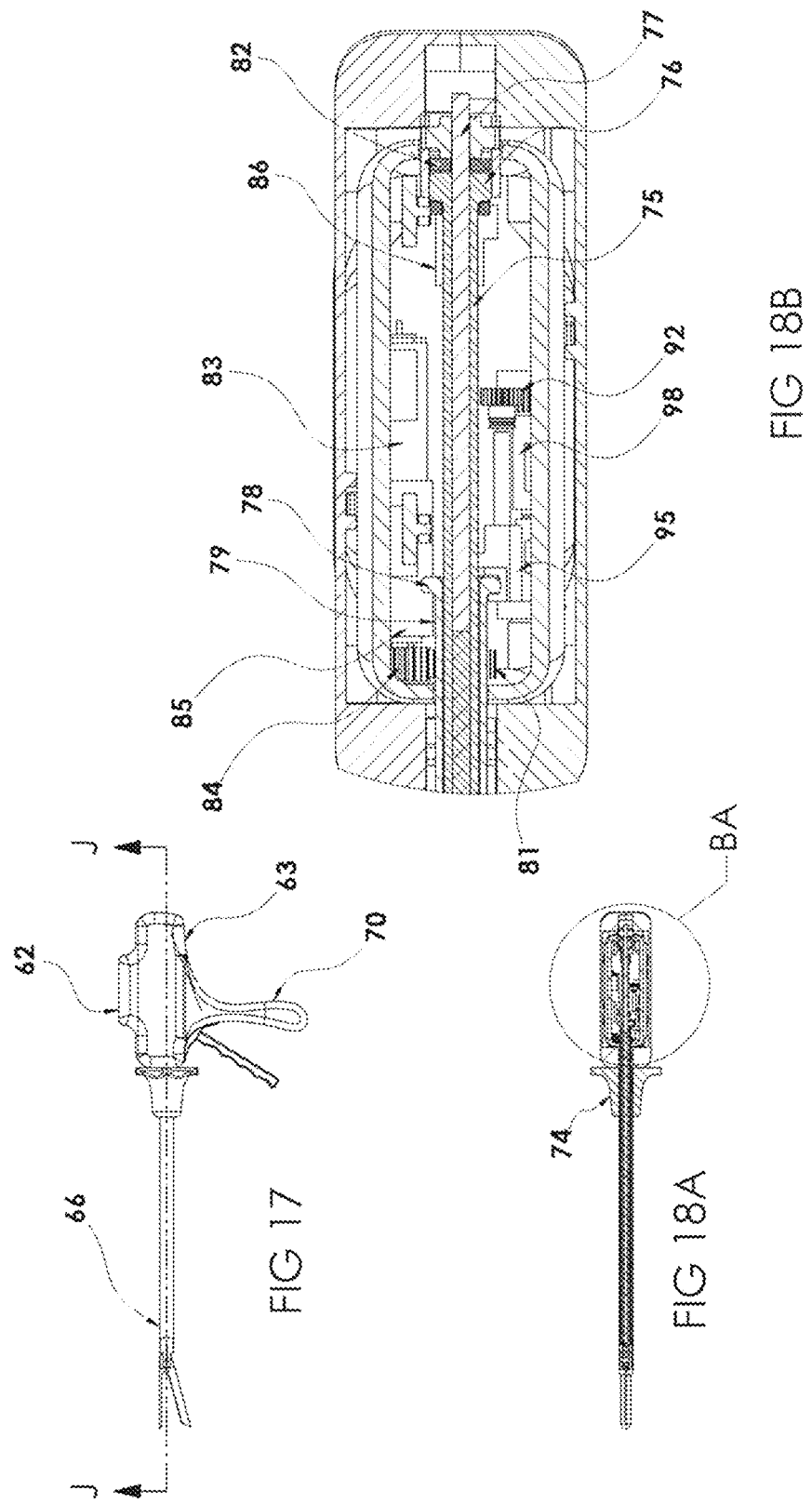
FIG. 17 is a side view of the surgical stapler of FIG. 14A, the view being the same as FIG. 14A but having section line J-J.
FIG. 18A is a cross-sectional view taken along line J-J of FIG. 17.
FIG. 18B is a close up view of the area of detail BA of FIG. 18A.
Figure 19C:
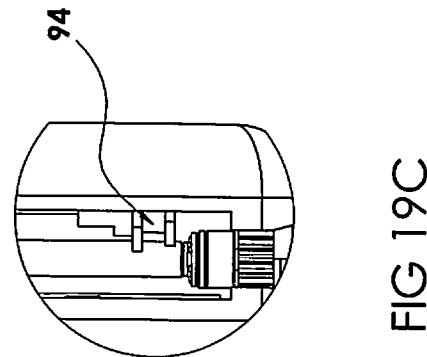
FIG. 19C is an enlarged view of the area of detail AL of FIG. 19A.
Figure 19B:
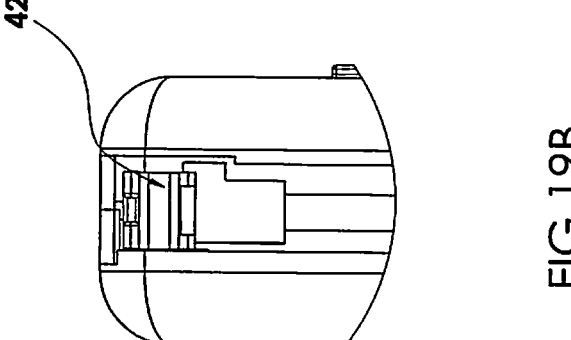
FIG. 19B is an enlarged view of the area of detail AK of FIG. 19A.
Figure 19A:
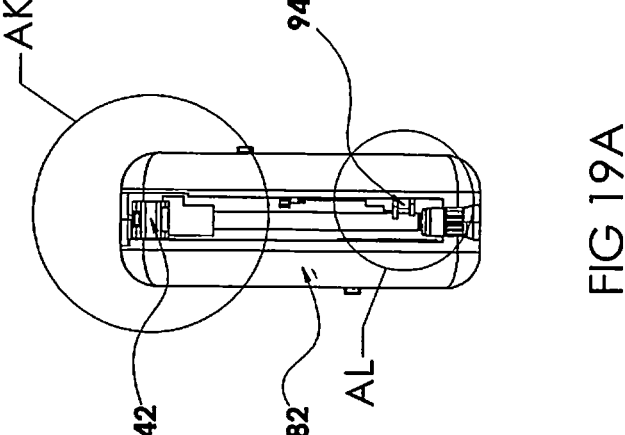
FIG. 19A is a top cutaway view of the power pack of FIG. 14A.
Figures 22A, 22B, 22C, 22D:
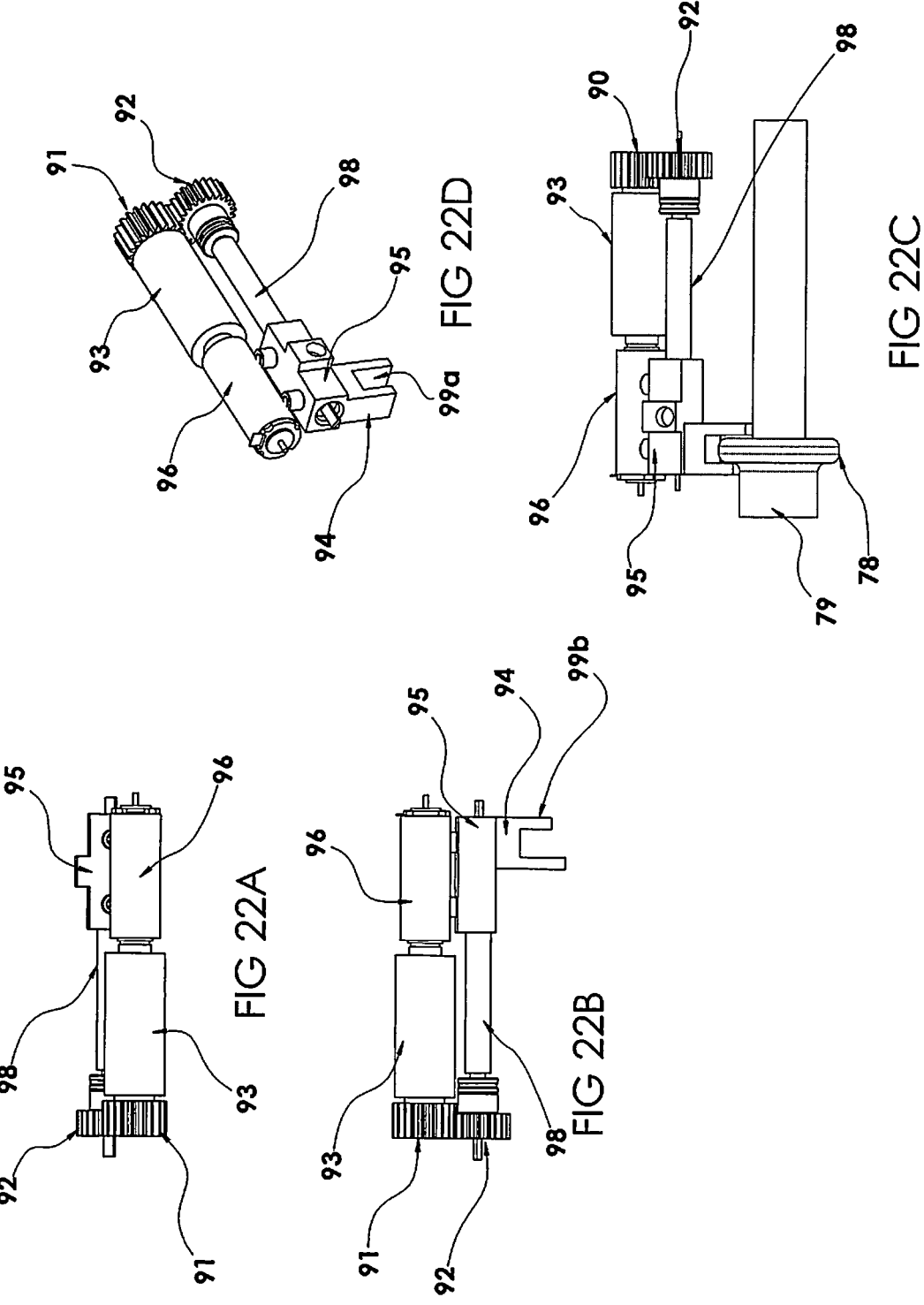
FIG. 22A is a top view of the motor and drive mechanism (assembly) of the power pack of FIG. 14A for effecting staple firing and articulation.
FIG. 22B is a side view of the motor and drive mechanism of the power pack of FIG. 14A.
FIG. 22C is a side view of the motor and drive mechanism of FIG. 14A shown engaged with the articulation rod of the articulation assembly of the surgical stapler of FIG. 14A.
FIG. 22D is a perspective view of the motor and drive mechanism (assembly) of the power pack of FIG. 14A.
Figure 23B:
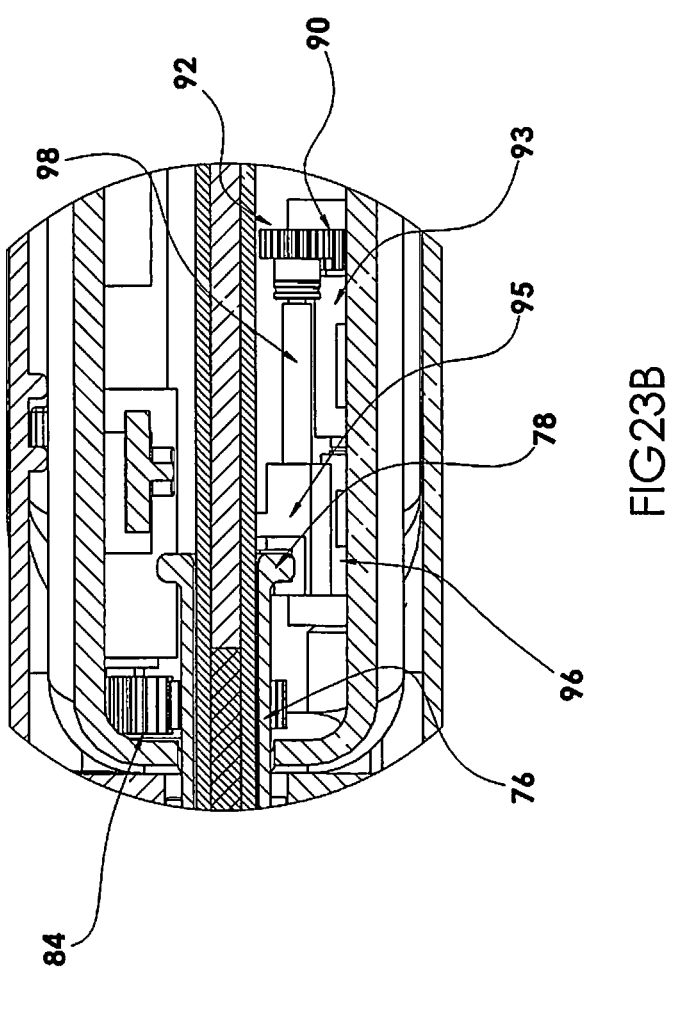
FIG. 23B is an enlarged view of the area of detail AU of FIG. 23A.
Figure 23A:
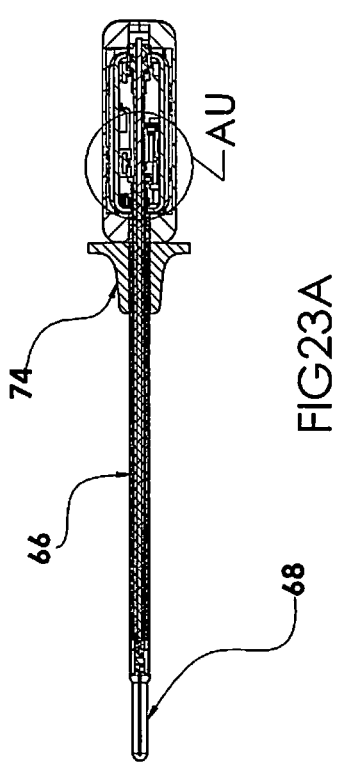
FIG. 23A is a cross-sectional side view of the surgical stapler of FIG. 14A, the view being the same as FIG. 18A but having and identified area of detail AU.
Figures 25A, 25B, 25C, 25D:
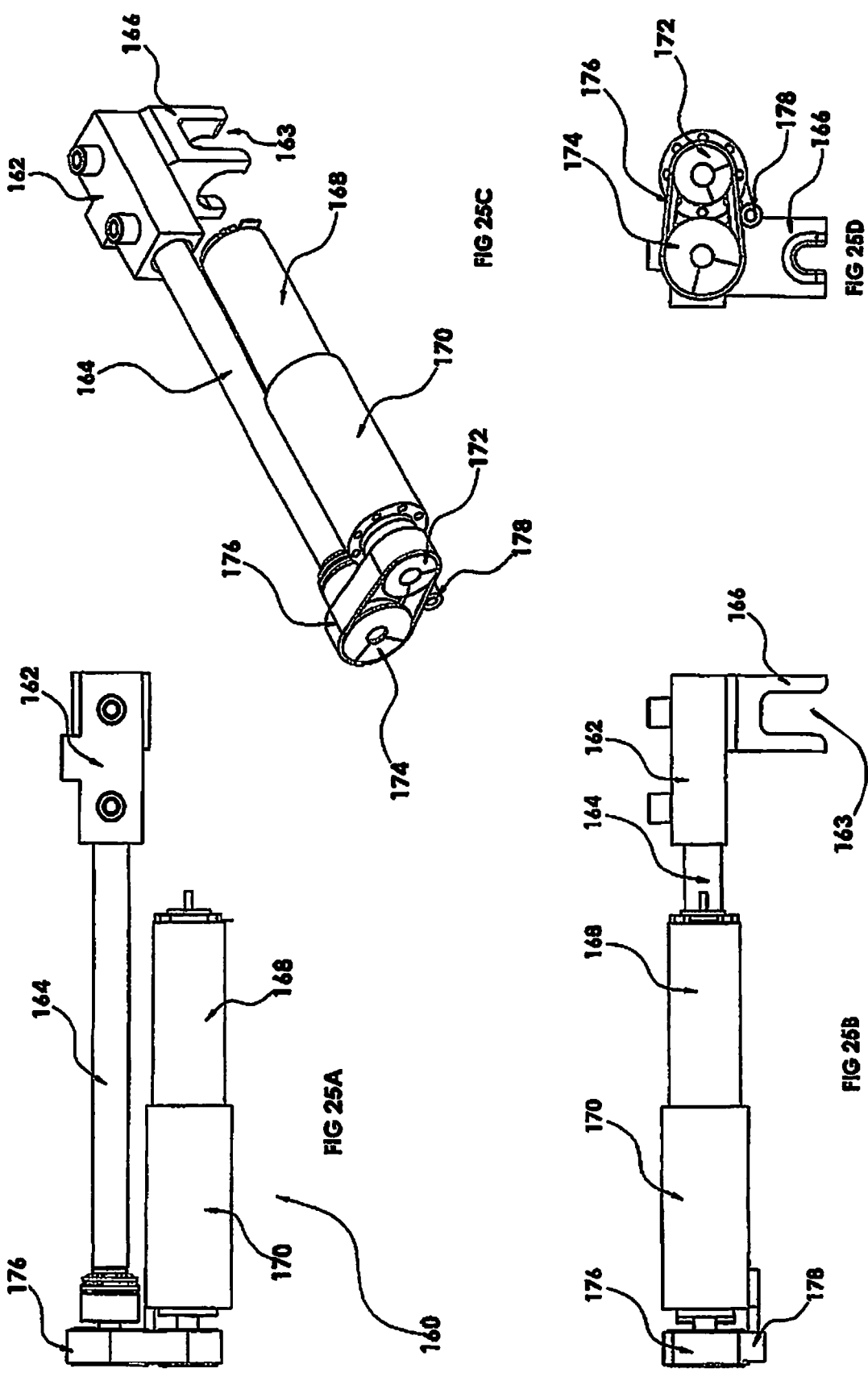
FIG. 25A is a top view of the motor and drive mechanism (assembly) of the power pack of an another alternate embodiment having a belt drive.
FIG. 25B is a side view of the motor and drive mechanism of FIG. 25A.
FIG. 25C is a perspective view of the motor and drive mechanism of FIG. 25A.
FIG. 25D is a front view of the motor and drive mechanism of FIG. 25A.
Figures 28A, 28B, 28C, 28D:
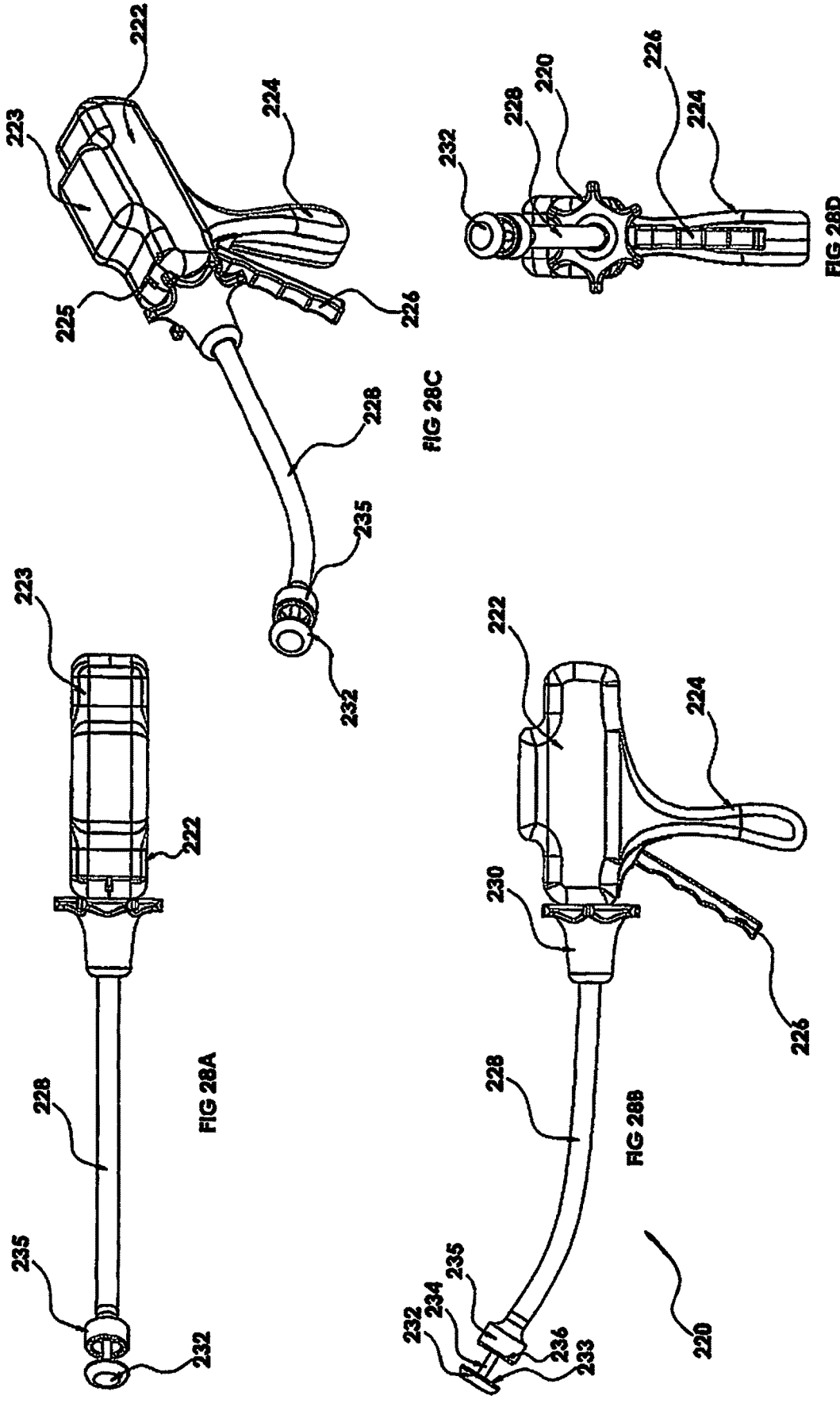
FIG. 28A is a top view of an alternate embodiment of the surgical instrument containing the power pack of FIG. 3A within the handle compartment, the surgical instrument being a circular stapler.
FIG. 28B is a side view of the circular stapler of FIG. 28A.
FIG. 28C is a perspective view of the circular stapler of FIG. 28A.
FIG. 28D is a front view of the circular stapler of FIG. 28A.
Figure 29C:
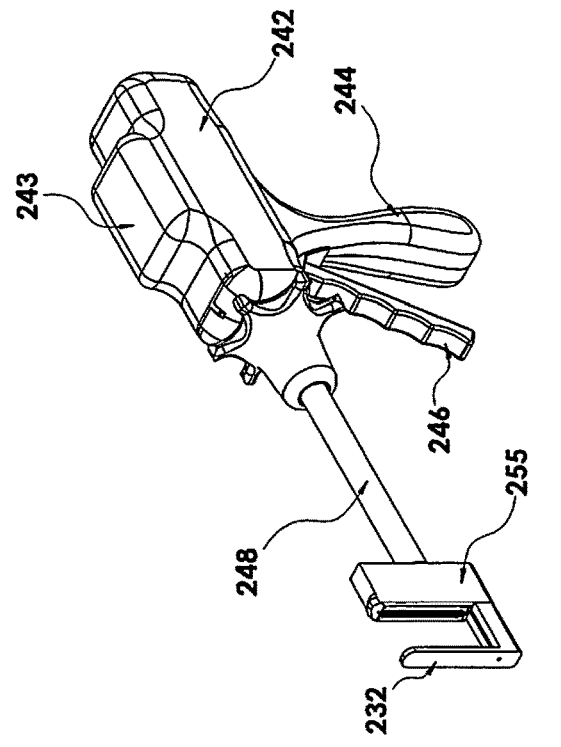
FIG. 29C is a perspective view of the linear stapler of FIG. 29A.
Figure 29D:
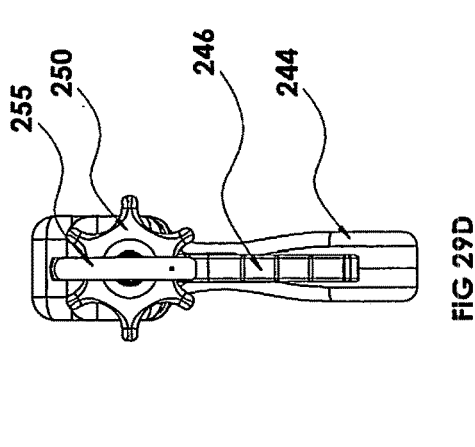
FIG. 29D is a front view of the linear stapler of FIG. 29A.
Figure 29A:
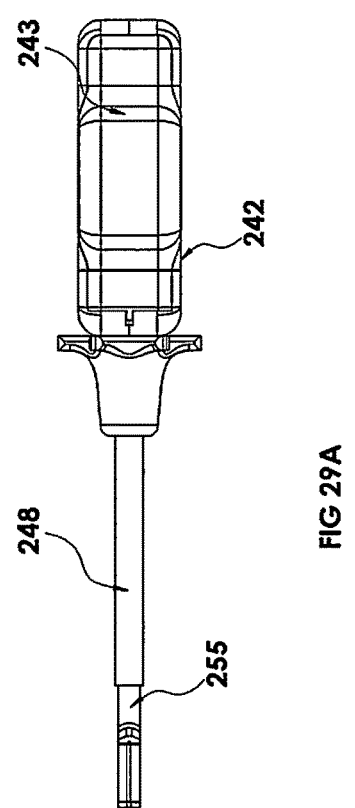
FIG. 29A is a top view of an alternate embodiment of the surgical instrument containing the power pack of FIG. 3A within the handle compartment, the surgical instrument being an open surgery linear stapler.
Figure 29B:
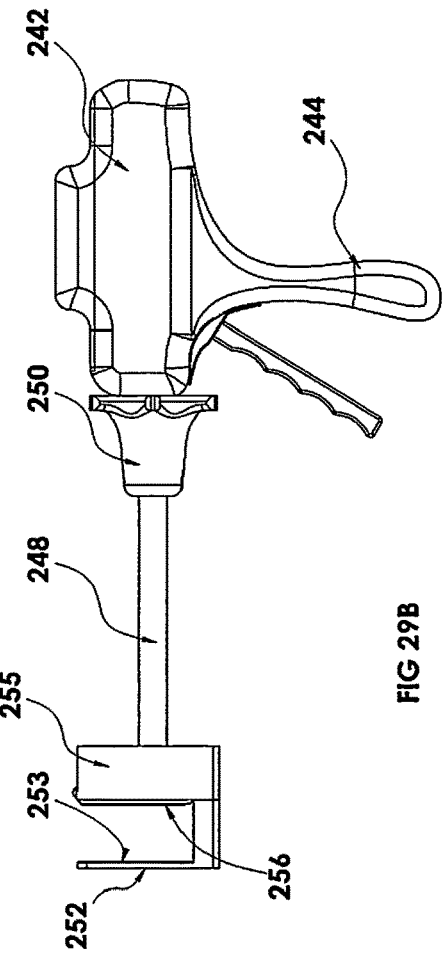
FIG. 29B is a side view of the linear stapler of FIG. 29A.
Figures 30A, 30B, 30C, 30D:
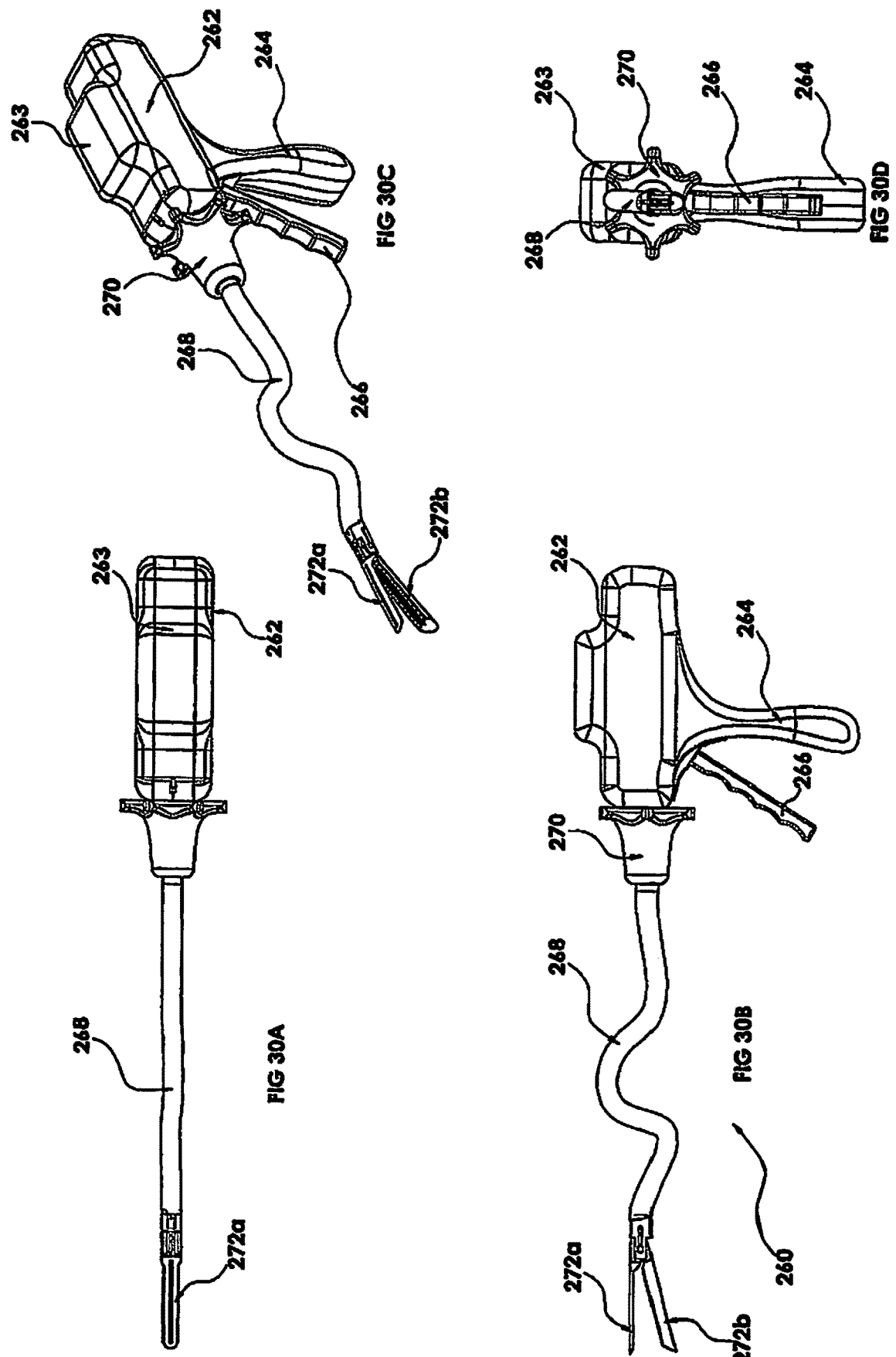
FIG. 30A is a top view of an alternate embodiment of the surgical instrument containing the power pack of FIG. 3A within the handle compartment, the surgical instrument being a flexible endoscopic linear stapler.
FIG. 30B is a side view of the linear stapler of FIG. 30A.
FIG. 30C is a perspective view of the linear stapler of FIG. 30A.
FIG. 30D is a front view of the linear stapler of FIG. 30A.
Figures 31A, 31B, 31C, 31D:
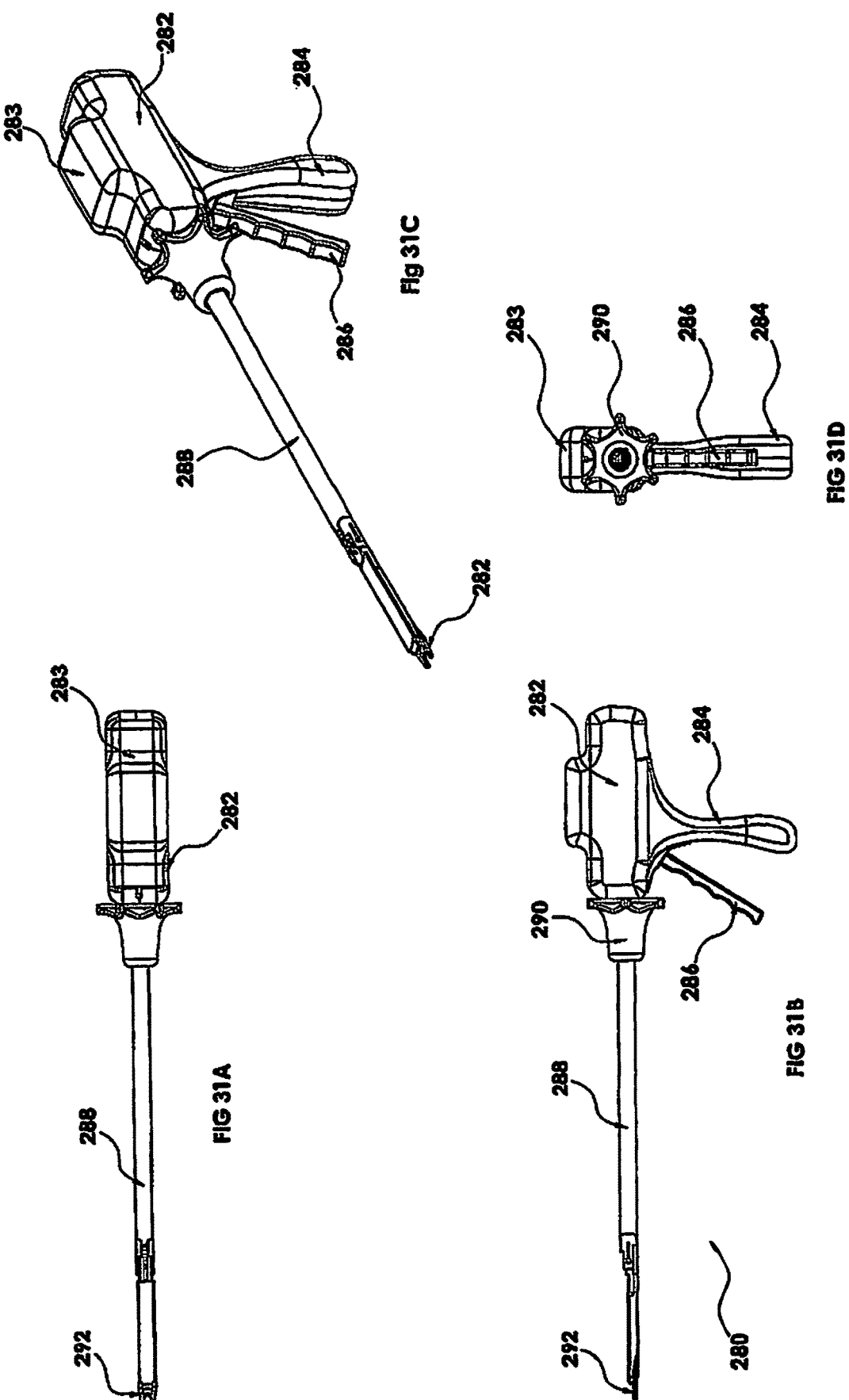
FIG. 31A is a top view of an alternate embodiment of the surgical instrument containing the power pack of FIG. 3A within the handle compartment, the surgical instrument being an endoscopic clip applier.
FIG. 31B is a side view of the clip applier of FIG. 31A.
FIG. 31C is a perspective view of the clip applier of FIG. 31A.
FIG. 31D is a front view of the clip applier of FIG. 31A.
Figures 32A, 32B, 32C, 32D:
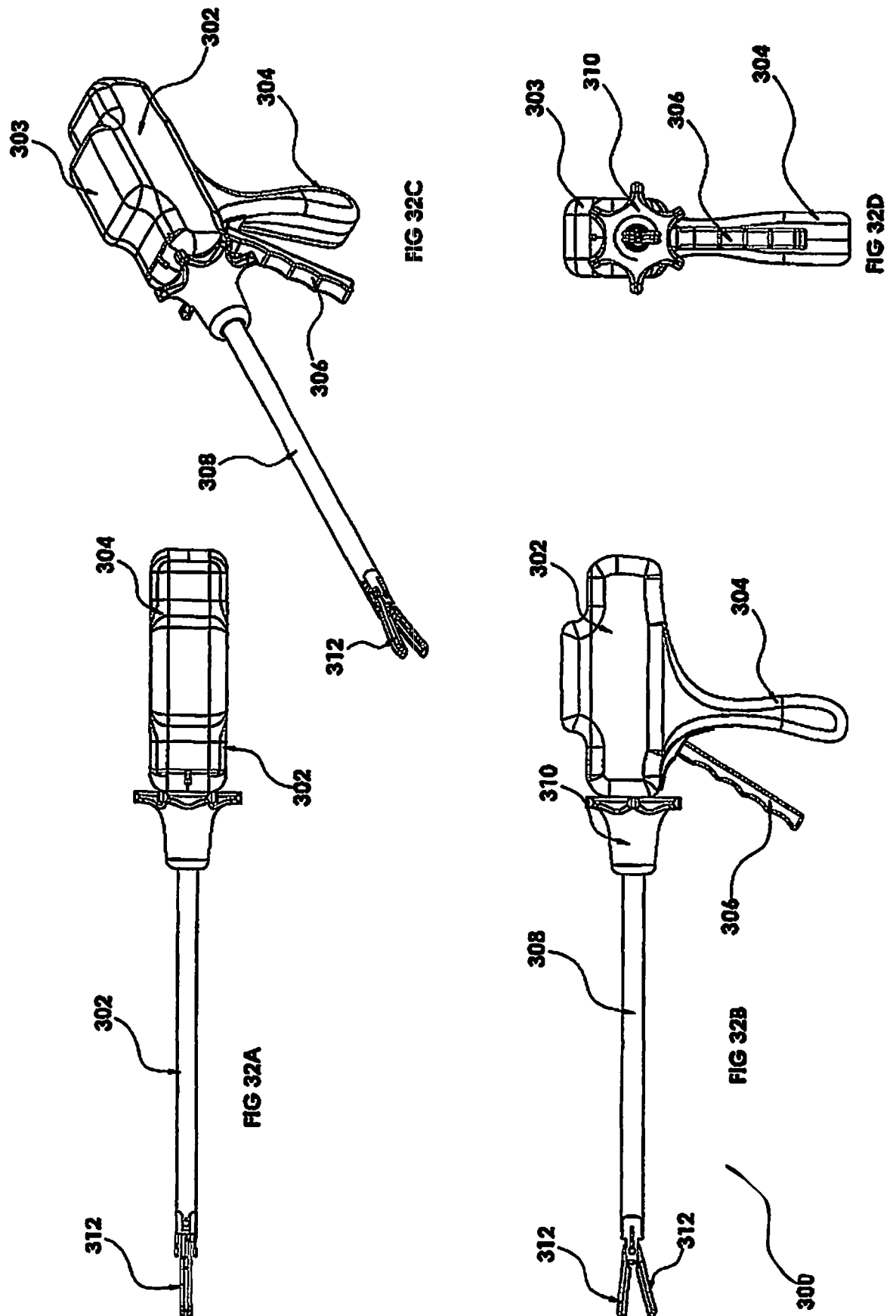
FIG. 32A is a top view of an alternate embodiment of the surgical instrument containing the power pack of FIG. 3A within the handle compartment, the surgical instrument being an endoscopic grasper.
FIG. 32B is a side view of the endoscopic grasper of FIG. 32A.
FIG. 32C is a perspective view of the endoscopic grasper of FIG. 32A.
FIG. 32D is a front view of the endoscopic grasper of FIG. 32A.
Figures 34A, 34B, 34C, 34D:
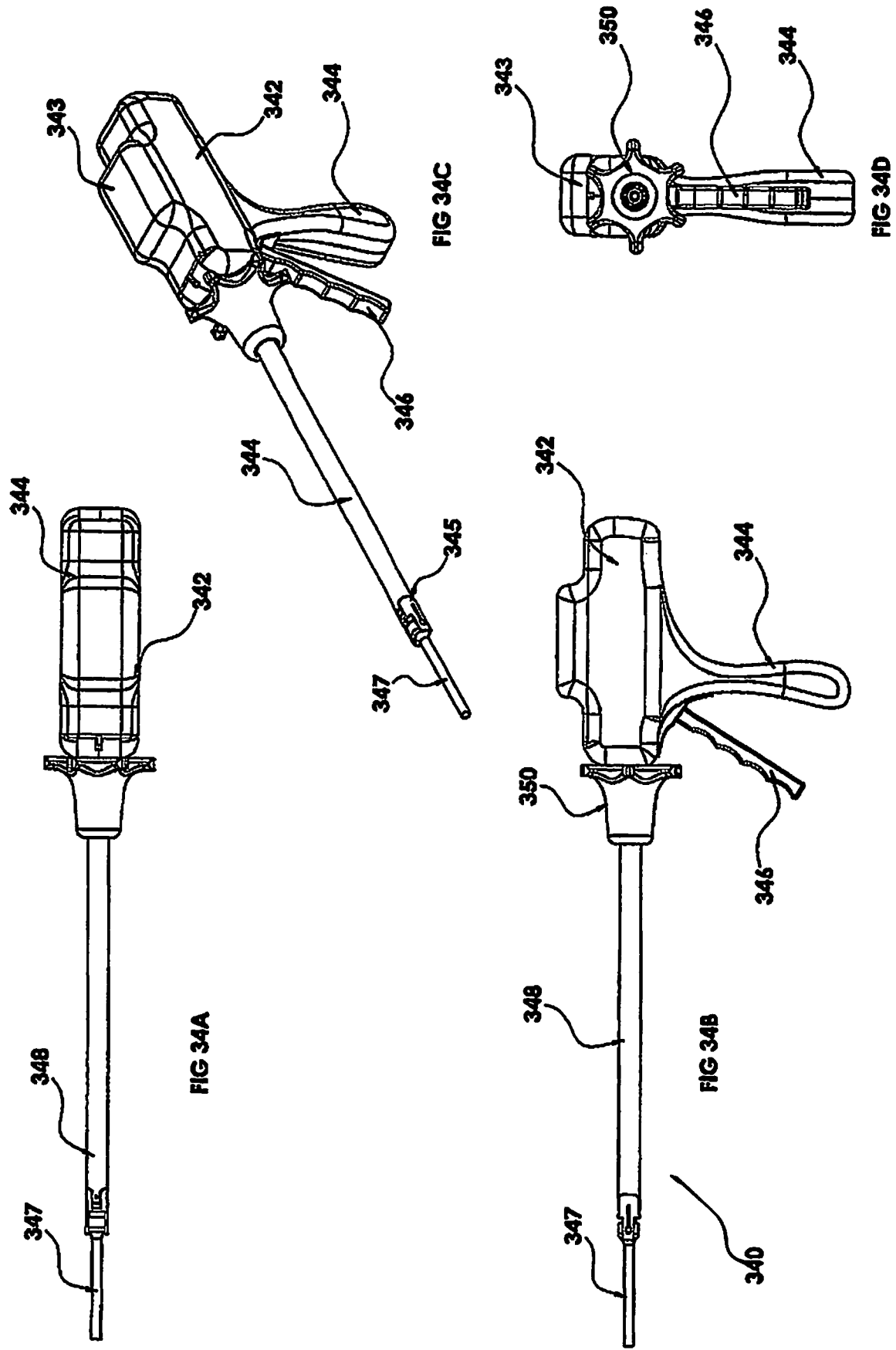
FIG. 34A is a top view of an alternate embodiment of the surgical instrument containing the power pack of FIG. 3A within the handle compartment, the surgical instrument being a fastener applier.
FIG. 34B is a side view of the fastener applier of FIG. 34A.
FIG. 34C is a perspective view of the fastener applier of FIG. 34A.
FIG. 34D is a front view of the fastener applier of FIG. 34A.

FIGS. 13C and 13D illustrate another endoscopic linear stapler that can receive the power pack 18. Endoscopic linear stapler 110 has a handle 112 manually pivotable toward stationary handle 113 for clamping of the jaws 118a, 118b, an endoscopic portion 116 extending from the handle housing 111, and a jaw assembly at the distal end of the endoscopic portion 116. The stapler 110 also includes a rotation knob 119 for rotation of the endoscopic portion 116 to rotate the jaws 118a, 118b. The stapler 110 can also include an articulation knob to articulate the jaws 118a, 118b. Power pack 18 is shown in FIG. 13C prior to loading within the handle housing 112 and shown in FIG. 13D fully loaded (inserted) within the handle housing 112. A cover (not shown) can be provided to seal the power pack 18 from the external environment. As in the embodiment of FIGS. 1-12, the flag 42 extending from lead screw 36 engages a firing rod within the handle housing 111 to effect movement of a firing rod to fire the staples when the motor of the power pack 18 is actuated. Power pack 90 having articulation described below can also be utilized with stapler 110.

FIGS. 30A-30D illustrate another type of endoscopic linear stapler that can receive and be powered by the power pack 18. Stapler 260 has a handle 266 manually pivotable towards stationary handle 264 for clamping of the jaws, an endoscopic portion 268 extending from the handle housing 267, and a jaw assembly containing jaws 272a, 272b. The endoscopic portion 268 is flexible which enables use in various endoscopic procedures. The stapler 260 also includes a rotation knob 270 for rotation of the endoscopic portion 268 to rotate the jaws 272a, 272b. Power pack 18 is shown fully loaded (inserted) within the handle housing 262 and cover 263 closed to seal the power pack 18 from the external environment. As in the embodiment of FIGS. 1-12, the flag 42 extending from lead screw 36 engages a firing rod within the handle housing 262 to effect movement of a flexible firing rod extending through flexible endoscopic portion 268 to fire the staples when the motor of the power pack 18 is actuated. Power pack 90 having articulation described below can also be utilized with stapler 260.

The power pack 18 is also not limited to use with endoscopic linear staplers, nor is it limited to use with staplers. FIGS. 28A-29D illustrate two examples of different staplers. As in the endoscopic linear staplers discussed herein, these staplers can also have a knife bar to cut tissue between the rows of staples applied to the tissue.

By way of example, the power pack 18 can be used with a circular stapler that applies circular arrays of staples such as shown in FIGS. 28A-28D. Surgical stapling instrument 220 can receive and be powered by the power pack 18 of the present disclosure. Stapler 220 has a handle 226 manually pivotable towards stationary handle 264 for clamping of the jaws, an elongated tubular portion 228 extending from the handle housing 222, and a jaw assembly having an anvil (jaw) 232 and a cartridge (jaw) 235 containing circular arrays of fasteners (staples). The anvil 232 has a proximal clamping surface 233 and is movable by anvil rod 234 toward the cartridge 235 to clamp tissue between the anvil clamping surface 233 and distal clamping surface 236 of cartridge 235 by manual movement of handle 226 toward stationary handle 224. The stapler 220 also includes a rotation knob 230 for rotation of the elongated portion (shaft) 228 to rotate the jaws 232, 235. Power pack 18 is shown fully loaded (inserted) within the handle housing 222 and cover 223 is shown closed to seal the power pack 18 from the external environment. As in the embodiment of FIGS. 1-12, the flag 42 extending from lead screw 36 engages a firing rod within the handle housing 222 to effect movement of a firing rod extending through elongated portion 228 to fire the circular arrays of staples when the motor of the power pack 18 is actuated. Power pack 90 having articulation described below can also be utilized with stapler 220.

By way of another example, the power pack can be used with a linear stapler that applies transverse rows of staples in a linear direction, i.e., parallel to the longitudinal axis of the stapler, such as shown in FIGS. 29A-29D. Surgical stapling instrument 240 can receive and be powered by the power pack 18 of the present disclosure. Stapler 240 has a handle 246 manually pivotable towards stationary handle 244 for clamping of the jaws, an elongated tubular portion 248 extending from the handle housing 242, and a jaw assembly containing an anvil (jaw) 252 and a cartridge (jaw) 255 containing linear rows of fasteners (staples) arranged perpendicular to the longitudinal axis of the stapler 240. The proximal anvil clamping surface 253 of anvil 252 and distal clamping surface 256 of cartridge 255 are brought into approximation by manual movement of handle 246 toward stationary handle 244 which advances cartridge 255 toward anvil 252. (Alternatively the anvil could be retracted toward the cartridge). The stapler 240 also includes a rotation knob 250 for rotation of the elongated portion (shaft) 248 to rotate the elongated portion 248 and jaws 252, 255. Power pack 18 is shown fully loaded (inserted) within the handle housing 242 and cover 243 is shown closed to seal the power pack 18 from the external environment. As in the embodiment of FIGS. 1-12, the flag 42 extending from lead screw 36 engages a firing rod within the handle housing 242 to effect movement of a firing rod extending through elongated portion 248 to fire the staples from cartridge 255 when the motor of the power pack 18 is actuated. Power pack 90 having articulation described below can also be utilized with stapler 240.

The power pack 18 can also be used with single firing instruments that fire a single staple, clip, tack, etc. into body tissue. Two examples of such instruments are illustrated in FIGS. 31A-31D and FIGS. 34A-34D. Turning first to the instrument 280 of FIGS. 31A-31D, by way of example, surgical clip applying instrument 280 can receive and be powered by the power pack 18 of the present disclosure. Stapler 280 has a handle 286 manually pivotable towards stationary handle 284 for loading a clip into the jaws, an elongated tubular portion 288 extending from the handle housing 282, and a pair of pivotable jaws 292 which support a clip therebetween. Closing of the jaws 292 crimps the clip about tissue. The clip applier 280 also includes a rotation knob 290 for rotation of the elongated portion (shaft) 288 to rotate the jaws 292. Power pack 18 is shown fully loaded (inserted) within the handle housing 282 and cover 283 is shown closed to seal the power pack 18 from the external environment. As in the embodiment of FIGS. 1-12, the flag 42 extending from lead screw 36 engages a rod within the handle housing 282 operably connected to a clip closing mechanism to effect movement of the clip closing mechanism to close the jaws to apply to tissue a surgical clip supported by the jaws 292. The power pack 18 can also have a motor powered drive assembly for advancing the clip into the jaws 292, the drive assembly engageable with a clip feed mechanism.

Another example of a single firing instrument is illustrated in FIGS. 34A-34D and designated generally by reference numeral 340. Instrument 340 can receive and be powered by the power pack 18 of the present disclosure. Instrument 340 has a handle 346 manually pivotable towards stationary handle 344 for angling the surgical tack and an elongated tubular portion 348 extending from the handle housing 342. Tacker support 345 is pivotable relative to the longitudinal axis by movement of handle 346 which is operably connected to an elongated member which pivots support 345. The instrument 340 also includes a rotation knob 350 for rotation of the elongated portion (shaft) 348. Power pack 18 is shown fully loaded (inserted) within the handle housing 342 and cover 343 is shown closed to seal the power pack 18 from the external environment. As in the embodiment of FIGS. 1-12, the flag 42 extending from lead screw 36 engages a rod within the handle housing 342 operably connected to a tack firing mechanism to effect advancement of the tack 347 into tissue. The power pack 18 can also be provided with a motor powered drive assembly to pivot support 345.

In the embodiments of FIGS. 1-12, a gear mechanism is driven by the motor to rotate the lead screw to advance the drive mechanism to effect firing of the staples. In the alternate embodiments of FIGS. 24A-27D, a belt drive mechanism is used to effect firing. The belt drive mechanism is contained in the power pack 18 in the same manner as the gear mechanism of the foregoing embodiments, and thus the power pack for the belt drive would include the housing 19 of the configuration of FIG. 1 and loaded in the stapler 1 in the same manner as power pack 18 described above. The belt drives of FIGS. 24A-27D are described below for use with stapler 1 of FIG. 1A but can be used in the other surgical staplers and instruments disclosed wherein which are designed to receive power pack 18 or power pack 90 for powered actuation.

Turning first to the embodiment of FIGS. 24A-24D, the belt drive assembly (mechanism) includes a motor 148 connected to a planetary gear box 150 configured to gear down the output of the motor 148 for proper drive speeds for firing staples from jaw 8a through the tissue into contact with the anvil of jaw 8b. The planetary gear box 150 drives a lead screw 144 via the drive belt operatively connected to the motor shaft. More specifically, upon rotation of the motor shaft by motor 148, first rotatable disc 152 (also referred to as the first wheel or pulley) is rotated in a first direction, causing movement of belt 156 and rotation of second rotatable disc 154 (also referred to as the second wheel or pulley). Note the two discs 152, 15 are spaced apart and not in contact. Lead screw 144 is operatively connected to disc 154 so that rotation of disc 154 causes rotation of lead screw 144 in the same direction. The power pack 18 includes a battery which can be rechargeable outside the stapler when the power pack 18 is removed. The motor 148 is actuated in the various ways described above with regard to power pack 18 of FIG. 3A. A tensioner can be provided such as tensioner 158, illustratively in the form of a tension disc or wheel, to apply a force against the belt 156. In the orientation of FIGS. 24C and 24D, the tensioner 158 is positioned underneath the drive belt 156 and applies an upward tensioning force against the belt 156 in a direction toward discs 152, 154. Other types of mechanisms to apply a tensioning force to the belt are also contemplated for use in the embodiments of FIGS. 24A-27D if such tensioning of the drive belt 156 is desired.

Connected to the end of lead screw 144 (the end opposite of the connection to the disc 154) is a drive mechanism 142. The drive mechanism 142, like drive mechanism 40 of FIG. 3A, is configured to move in a linear motion (in an axial direction) along the lead screw 144 in response to rotation of the lead screw 144. For example, as in the drive mechanism 40, drive mechanism 142 may include internal threads that engage external threads of the lead screw 144 and may include slides engaged in a track that prevent the drive mechanism 142 from rotating and therefore cause the drive mechanism 142 to move linearly in response to rotation of the lead screw 144. As shown, the lead screw 144 extends alongside, slightly spaced from, the motor 148 and gear box 150, i.e., both the motor 148/gear box 150 and lead screw 144 extending longitudinally with the lead screw 144 parallel to the motor 148. The drive mechanism 142 extends proximally of the proximal end of the motor 148 in the illustrated embodiment.

The drive mechanism 142, like drive mechanism 140 of FIG. 3A, includes a first output flag or yoke 146 with slot 143 configured to engage a staple firing rod 46 extending longitudinally within the handle 4. The flag 146 is the same as flag 42 of FIG. 4A and engages the staple firing rod 46 in the same manner as flag 42. Therefore, for brevity, further discussion of flag 146 and it engagement with firing rod 46 is not provided as the structure and function of flag 42, and alternative firing rod engagement features, are fully applicable to flag 146 of FIGS. 24A-24D. In brief, as the motor 148 generates rotational motion of the lead screw 144 through the drive belt, the drive mechanism 144 moves in linear motion along the lead screw 144 to effect linear movement of the firing rod 46 which advances the staple driving mechanism to advance (fire) the staples out from jaw 8b through tissue and into contact with the anvil in jaw 8a.

FIGS. 25A-25D illustrate an alternate embodiment of a belt drive mechanism. Belt drive mechanism (assembly) 160 is identical to belt drive 140 except for the different sized discs (wheels). That is, assembly 160 has a motor 168 connected to a planetary gear box 170 configured to gear down the output of the motor 168. The planetary gear box 170 drives a lead screw 164 through the belt drive operatively connected to the motor shaft. Upon rotation of the motor shaft by motor 168, first disc 172 is rotated in a first direction, causing movement of belt 176 and rotation of second disc 174 in the same direction. Lead screw 164 is operatively connected to disc 174 so that rotation of disc 174 causes rotation of lead screw 164 in the same direction. A tensioner 178 like tensioner 158 can be provided to apply tension to the belt 176. The drive mechanism 162, like drive mechanism 40 of FIG. 3A, includes a first output flag or yoke 166 with slot 163 configured to engage a staple firing rod 46 in the same manner as flag 42. Rotation of the motor shaft generates rotational motion of the lead screw 164 through the drive belt, causing the drive mechanism 162 to move in linear motion along the lead screw 164 to effect linear movement of the firing rod 46 which advances the staple driving mechanism to advance (fire) the staples out from jaw 8b through tissue and into contact with the anvil in jaw 8a.

The belt drive 160 differs from belt drive 140 of FIG. 24A in that second disc 174 which is operatively connected to lead screw 164 is larger in diameter than first disc 172. Consequently, instead of providing a one to one ratio of the discs as in discs 154 and 152 of FIG. 24A, a greater ratio of disc 174 to disc 172 is provided which varies the output of motor 168. That is, the rotational output of lead screw 164 is less than the rotational output of the motor shaft due to the differing degree of rotation of discs 174, 178 due to the varying sizes. In all other respects, mechanism 160 is identical to mechanism 140.

FIGS. 26A-26D illustrate an alternate embodiment of a belt drive mechanism. Belt drive mechanism (assembly) 180 is identical to belt drive 140 of FIG. 24A except for the configuration of the drive belt and discs. That is, assembly 180 has a motor 188 connected to a planetary gear box 190 configured to gear down the output of the motor 188. The planetary gear box 190 drives a lead screw 184 through the belt drive operatively connected to the motor shaft. Upon rotation of the motor shaft by motor 188, first disc (wheel or pulley) 192 is rotated in a first direction, causing movement of belt 196 and rotation of second disc (wheel or pulley) 194. Lead screw 184 is operatively connected to disc 194 so that rotation of disc 194 causes rotation of lead screw 184 in the same direction. A tensioner 198 like tensioner 158 can be provided to apply tension to the belt 196. The drive mechanism 182, like drive mechanism 140 of FIG. 3A, includes a first output flag or yoke 186 with slot 183 configured to engage a staple firing rod 46 in the same manner as flag 42. Rotation of the motor shaft generates rotational motion of the lead screw 184 through the drive belt, causing the drive mechanism 182 to move in linear motion along the lead screw 184 to effect linear movement of the firing rod 46 which advances the staple driving mechanism to advance (fire) the staples out from jaw 8b through tissue and into contact with the anvil in jaw 8a.

The belt drive 180 differs from belt drive 140 of FIG. 24A in that discs 192, 194 have teeth to engage ribs or treads on belt 196. As shown, the toothed discs 192, 194 are spaced apart so their teeth/projections do not intermesh—the teeth of disc 192 engage belt 196 and the teeth of disc 194 engage belt 196. Rotation of disc 192 moves drive belt 194 in the same direction due to its engagement with the teeth, which causes rotation of toothed disc 194 in the same direction due to engagement with its teeth to rotate lead screw 184. In all other respects, mechanism 180 is identical to mechanism 140.

FIGS. 27A-27E illustrate an alternate embodiment of a belt drive mechanism. Belt drive mechanism (assembly) 200 is identical to belt drive 180 except for the different sized discs. That is, assembly 200 has a motor 208 connected to a planetary gear box 210 configured to gear down the output of the motor 208. The planetary gear box 210 drives a lead screw 204 through the belt drive operatively connected to the motor shaft. Upon rotation of the motor shaft by motor 208, first disc (wheel or pulley) 212 is rotated in a first direction, causing movement of belt 216 and rotation of second disc (wheel or pulley) 214. Lead screw 204 is operatively connected to disc 214 so that rotation of disc 214 causes rotation of lead screw 204 in the same direction. A tensioner 218 like tensioner 198 can be provided to apply tension to the belt 216. The drive mechanism 202, like drive mechanism 140 of FIG. 3A, includes a first output flag or yoke 206 with slot 203 configured to engage a staple firing rod 46 in the same manner as flag 42. Rotation of the motor shaft generates rotational motion of the lead screw 204 through the drive belt, causing the drive mechanism 202 to move in linear motion along the lead screw 204 to effect linear movement of the firing rod 46 which advances the staple driving mechanism to advance (fire) the staples out from jaw 8b through tissue and into contact with the anvil in jaw 8a.

The belt drive 200 differs from belt drive 180 of FIG. 24A in that second toothed disc 214 which is operatively connected to lead screw 204 is larger in diameter than first toothed disc 172. Consequently, instead of providing a one to one ratio of the discs as in discs 194 and 192, a greater ratio of disc 214 to disc 212 is provided which varies the output of motor 208. That is, the rotational output of lead screw 204 is less than the rotational output of the motor shaft due to the differing degree of rotation of discs 214, 212 due to the varying sizes. In all other respects, mechanism 200 is identical to mechanism 180.

It should be appreciated that the foregoing belt drive mechanisms can be used as an alternative to the gear mechanism in power pack 18 as well as an alternative to one or both of the gear mechanisms of power pack 90 discussed below.

In the foregoing embodiments, the power pack 18 was described for powering staple firing. In an alternate embodiment, the power pack can include a drive mechanism for effecting articulation. This motor powered articulation can be in addition to the motor powered staple firing, or alternatively, the power pack can be used solely for powered articulation. The embodiment of FIGS. 14A-23B illustrate a surgical stapler and power pack which powers both staple firing and articulation. If only for articulation, the power pack described below (power pack 90) would not include the gear mechanism engageable with the firing rod 46 for staple firing.

With initial reference to FIGS. 14A-14C, surgical stapler 61 is identical to surgical stapler 1 of FIG. 1A except for the power pack mounted in the stapler 61 and the articulation rod in the stapler 61 which is engaged by the power pack. Thus, like stapler 1, stapler 61 has a handle assembly 63, an endoscopic portion 66 extending distally therefrom and a pair of jaws 68a, 68b, (collectively "jaws 68") with at least one of the jaws movable relative to the other jaw, e.g., jaw 68b containing the staples (fasteners) movable toward stationary jaw 68a containing the anvil pockets. Handle 72 like handle 14 of stapler 1 is pivotable toward stationary handle 70 to approximate jaws 68a, 68b to clamp tissue between the closed jaws 68a, 68b. Handle assembly 63 includes a housing 64 and cover 62 which is identical to cover 22 of stapler 1, i.e., pivotably mounted to the housing 64 to move from a closed to an open position for top loading (or alternatively other directional loading) a power pack into the compartment within the housing 64. The compartment, like compartment 25 described above, retains the power pack and can include guiding structure for alignment of the power pack similar to guiding structure 28 described above to receive guides 90a, 90b of power pack 90. Stapler 61 also includes a rotation knob 74 which functions in the same manner as rotation knob 12 of stapler 1 described above to rotate tubular portion (shaft) 66. The jaw assembly, i.e., jaws 68a, 68b, articulate about joint 69 to move the jaws 68a, 68b to angular positions with respect to the longitudinal axis of stapler 61.

The power pack in the embodiment of FIGS. 14A-23B is designated by reference numeral 90 and has a motor assembly and drive mechanism for firing staples which is identical to that of the power pack 18 of FIG. 3A. However, power pack 90 differs from power pack 18 in that it additionally has a motor assembly and drive mechanism for articulating the jaws. The addition of the articulation assembly can be appreciated by a comparison of the cross-sectional view of FIG. 4H, which only effects firing of the fasteners (staplers), and the cross-sectional view of FIG. 15F which effects firing of fasteners and articulation of the jaw assembly.

Figures 4G, 4H, 4I:
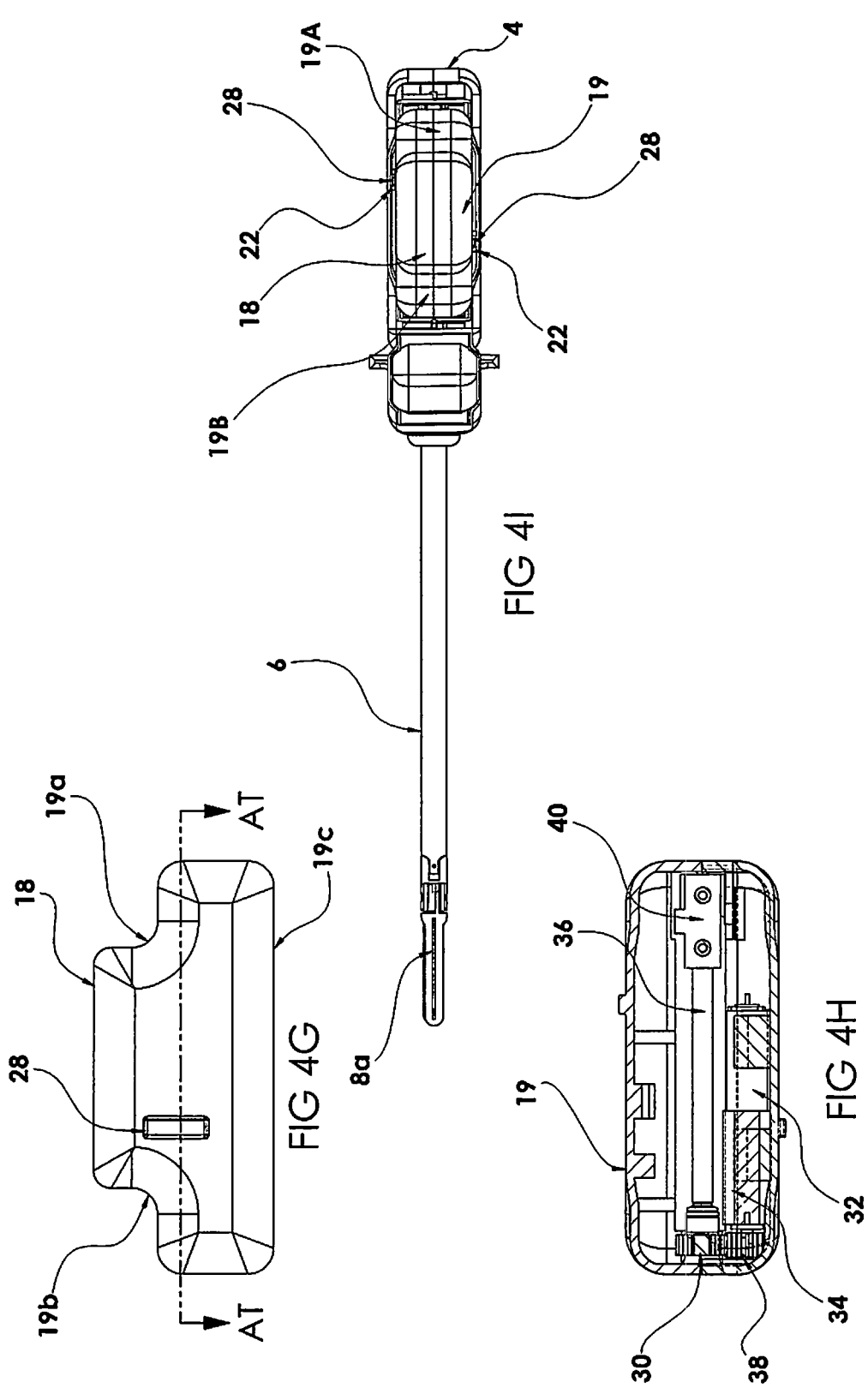
FIG. 4G is a side view of the power pack of FIG. 3A.
FIG. 4H is a cross-sectional view taken along line AT-AT of FIG. 4G.
FIG. 4I is a top view of the surgical stapler of FIG. 1.

More specifically, with reference to FIGS. 15A-15F and 18B, the powered staple firing assembly like the firing assembly of power pack 18 of FIG. 4H, includes a motor 83 connected to a planetary gear box 85 configured to gear down the output of the motor in the same manner as motor 32 and gear box 34 of power pack 18. The planetary gear box 85 drives a lead screw 86 through one or more gears operatively connected to the motor shaft. More specifically, upon rotation of the motor shaft by the motor 83 in a first direction, gear 81 is rotated in the same first direction, causing rotation of the gear 84 in a second opposite direction due to the intermeshed teeth of gears 81 and 84. Lead screw 86 is operatively connected to gear 84 so that rotation of gear 84 causes rotation of lead screw 86 in the same direction. The power pack 18 includes a battery 33 which can be rechargeable outside the stapler when the power pack 18 is removed. The power pack 90 in some embodiments can include a power switch which is activated, i.e., turned on, by the clinician to start the motor and effect staple firing. In other embodiments, the motor can automatically turn on when fully loaded or upon actuation of another control on the stapler housing 4.

Connected to the end of lead screw 86 (the end opposite the connection to the gear 84) is a drive mechanism 80 which is configured to move in a linear motion (in an axial direction) along the lead screw 86 in response to rotation of the lead screw 86. Drive mechanism 80 includes a flag or yoke 82 identical to yoke 42 of power pack 18 discussed above, which engages flange or boss 76 of firing rod 75 within housing 64 of stapler 61. The connection of the flag 82 to the firing rod 76, the motor and gear mechanism, and the drive mechanism 80 of power pack 90 are the same as the power pack 18 and therefore the aforedescribed functions and features/components of power pack 18 for staple firing are fully applicable to the function and features/components of power pack 90 for staple firing so for brevity are not fully repeated herein. It should also be appreciated that the alternative mechanisms for motor powered stapled firing, such as the various belt drive mechanisms discussed above and/or illustrated in the Figures, can also be used in the power pack 90 to effect staple firing. Additionally, the various sensors discussed above with regard to sensing the firing stroke can also be provided in power pack 90 for the same uses.

Power pack 90 also has an articulation assembly, shown in detail in FIGS. 22A-22D. The articulation assembly includes a powering assembly including a motor 96 connected to a planetary gear box 93 configured to gear down the output of the motor 96. The planetary gear box 93 drives a lead screw 98 through gears 91, 92 operatively connected to the motor shaft. More specifically, upon rotation of the motor shaft by motor 96 in a first direction, gear 91 is rotated in the same first direction, causing rotation of the gear 92 in a second opposite direction due to the intermeshed teeth of gears 92 and 91. Lead screw 98 is operatively connected to gear 92 so that rotation of gear 92 causes rotation of lead screw 98 in the same direction. The power pack 90 in some embodiments can include a power switch which is activated, i.e., turned on, by the clinician to start the motor and effect articulation.

Connected to the end of lead screw 98 (the end opposite the connection to the gear 92) is a drive mechanism 95 configured to move in a linear motion (in an axial direction) along the lead screw 98 in response to rotation of the lead screw 98. For example, the drive mechanism 95, like drive mechanisms 40 and 80 described above, may include internal threads that engage external threads of the lead screw 98 and may include slides engaged in a track that prevent the drive mechanism 95 from rotating and therefore cause the drive mechanism 95 to move linearly (axially) in response to rotation of the lead screw 98. As depicted, the power pack 90 has a compact configuration as the lead screw 98 extends alongside, slightly spaced from, the motor 96 and gear box 93, i.e., both the motor 96/gear box 93 and lead screw 98 extending longitudinally with the lead screw 98 parallel to the motor 96. The drive mechanism 95 is connected to a proximal end of lead screw 98. The drive mechanism 95 has an articulation rod engagement feature in the form of a flange or yoke 94 extending therefrom having legs 99a and a recess 99b to engage an articulation rod 79 within the housing 63. In the illustrated embodiment (see e.g., FIGS. 15B and 22C), the articulation rod 79 includes a flange 78 which is engageable by the flag 94. The output flag 94 can engage the bossed end 78 of the articulation tube 79 in substantially the same manner as the output flag 42 engages the bossed end 44 of the firing rod 46 as discussed above.

The articulation assembly of the power pack 90 is oriented in the opposite direction from the staple firing assembly to minimize the space required in the power pack 90, thereby providing the power pack with a compact configuration. As can be appreciated by reference to FIGS. 15A and 15F, the drive assembly 80 and associated flag 82 are at a proximal end of the assembly for firing staples with the lead screw 86 extending distally toward the gears 81, 84. The driving assembly 95 with associated flag 94 of the assembly for articulation are at a distal end with the lead screw 98 extending proximally toward gears 91, 92. Also as can be appreciated by reference to the orientation of FIGS. 15A and 15F, the articulation assembly is above (closer to the cover 22) than the firing assembly, and the articulation assembly in the illustrated embodiment is positioned axially proximal of gears 81, 84 and axially distal of drive mechanism 80, radially spaced from lead screw 86.

The power pack 90, like power pack 18 can have features/structure to constrain the motors 84 and 96. In the embodiment of FIG. 15D, such feature is in the form of proximal rails 97a and distal rails 97b spaced apart axially within the housing of the power pack 90. Gear box 93 is seated within proximal rails 97a and motor 96 is seated within distal rails 97b, the rails 97a, 97b retaining the motor and preventing axial and rotational movement within the housing of power pack 90. Bearing or bushings 98a, 98b can also be provided to constrain the lead screw 98 at opposing ends, while allowing rotation thereof, thereby also constraining the motor. Other features can additionally or alternatively be provided to restrain the motor from axial movement while allowing rotation of the lead screw.

The power pack 90 can include guides, e.g., projections 90a, 90b, either axially aligned or axially offset, similar to guides 28 of power pack 18 for alignment with guiding structure in the compartment of stapler 61. This can prevent misloading of the power pack.

In use, with the cover 62 of stapler 61 in the open position, power pack 90 is loaded into the compartment of the handle housing 63. The cover 62 is closed to seal the power pack 90 from contaminants in same manner as cover 22 of stapler 1. Upon loading of the power pack 90, flag 82 of the drive mechanism 80 of the staple firing assembly engages flange 76 of firing rod 75 and flag 94 of drive mechanism 95 of the articulation assembly engages flange or bossed end 78 of articulation rod 79. Actuation of the motor 96 effects linear motion of the flag 94 which moves the articulation rod 79 linearly (axially). The articulation rod 79 is either directly coupled to the joint 69, or coupled to another member or multiple members which are coupled to the joint 69. When moved linearly, the articulation rod 79 effects movement of the jaws 68A, 68b of the stapler 61 to angular positions with respect to the longitudinal axis of the stapler 61. Note the articulation drive assembly operates in a similar manner as the firing drive assembly of power pack 18 in that when the power pack 90 is secured to the tube 79 by the second output flag 94, linear motion generated at the second output flag 94 is transferred to linear motion of the tube 79.

Actuation of the motor 83 effects linear motion of the flag 82 which moves the firing rod 75 linearly (axially). The firing rod 75 either extends through the elongated portion 66 for engagement of the firing mechanism in the jaw 68b or is coupled to another elongated component(s) extending through the endoscopic portion 66 to engage the firing mechanism in the jaw 68b. Note that the articulation rod or tube 79 can be configured to receive the firing rod 75 so that the firing rod 75 can move within the tube 79 to effect firing and the articulation rod 79 can slide linearly over the firing rod to effect articulation.

After use, the cover 62 can be opened and the power pack 90 removed and charged while the handle assembly 63 (and stapler 61) is sterilized or disposed of if the stapler is a disposable instrument. The power pack 90, like power pack 18 described above, may be reused without requiring sterilization by being inserted into the receptacle of the now-sterilized handle assembly 63 or a different sterile handle assembly. Thus, the removable power pack 90, like power pack 18, does not need to be subjected to the sterilization process and, therefore, contact between the harsh temperatures and/or chemicals of the sterilization process is advantageously avoided.

One or more seals are utilized for sealing power pack 18 and power pack 90 within the handle assembly 2 or 63 so that the power pack remains sterile and is not exposed to bodily fluids during surgical procedures. For example, as discussed above, in the stapler 1 of FIG. 1, the top seal 24 is positioned at the interface between the cover 22 and the housing 4 of the handle assembly 2 where the cover 22 closes for sealing the opening into the receptacle 20 and, therefore, power pack 18 from the environment when positioned therein. Similarly, in the stapler 61 of FIG. 14A, the top seal is positioned at the interface between the cover 62 and the housing 64 of the handle assembly 63 wherein the cover 62 closes for sealing the opening into the receptacle and, therefore, power pack 90 from the environment when positioned therein. As shown in FIGS. 21A-21C, further seals can be provided to further seal the receptacle and thus the power pack. An O-ring 56 is placed around the articulation rod 79 to seal the space around the rod 79. A flexible trigger seal 58 surrounds the lever 72 for sealing the internal components of the handle assembly 63 throughout the range of positions of the movable lever 72. Thus, all of the openings into the receptacle of the handle assembly 63 are sealed from the external environment. The O-ring seal 56 and trigger seal 58 can also be used in stapler 1 so the openings into the receptacle 20 of handle assembly 2 are sealed from the external environment. Elastomeric seal 59a seals cover 62 from U-channel 59 within the handle which supports the power pack 90. Additional seals can be provided to prevent flow of body fluid through the endoscopic portion 66 (and endoscopic portion 6). Other types of seals and seals in different locations are also contemplated.

FIGS. 35-37C illustrate alternate embodiments of the power pack having a removable battery pack. Each of the power packs (power trains) 406, 420 and 430 in the embodiments of FIGS. 35-37C can have a motor assembly and drive mechanism for firing staples which is identical to that of the power pack 18 of FIG. 3A or alternatively can have a motor and drive mechanism for firing staples and additionally a motor assembly and drive mechanism for articulating the jaws as in power pack 90 of FIG. 14A described above. The surgical staplers for receiving power packs 406, 420 or 430 are the same as the surgical stapler 1 (except for the compartment and cover) so that it has been labeled with like reference numerals. The power packs 406, 420 and 430 could also be used with the other surgical staplers described herein or with other surgical instruments such as those described herein. Therefore, further discussion of the surgical staplers is not provided herein as the description of the stapler 1 components (e.g., shaft 6, jaws 8a, 8b, handle 12, etc.) and its functions, as well the description of other staplers, are fully applicable to the stapler receiving power packs 406, 420 or 430.

Figure 35:
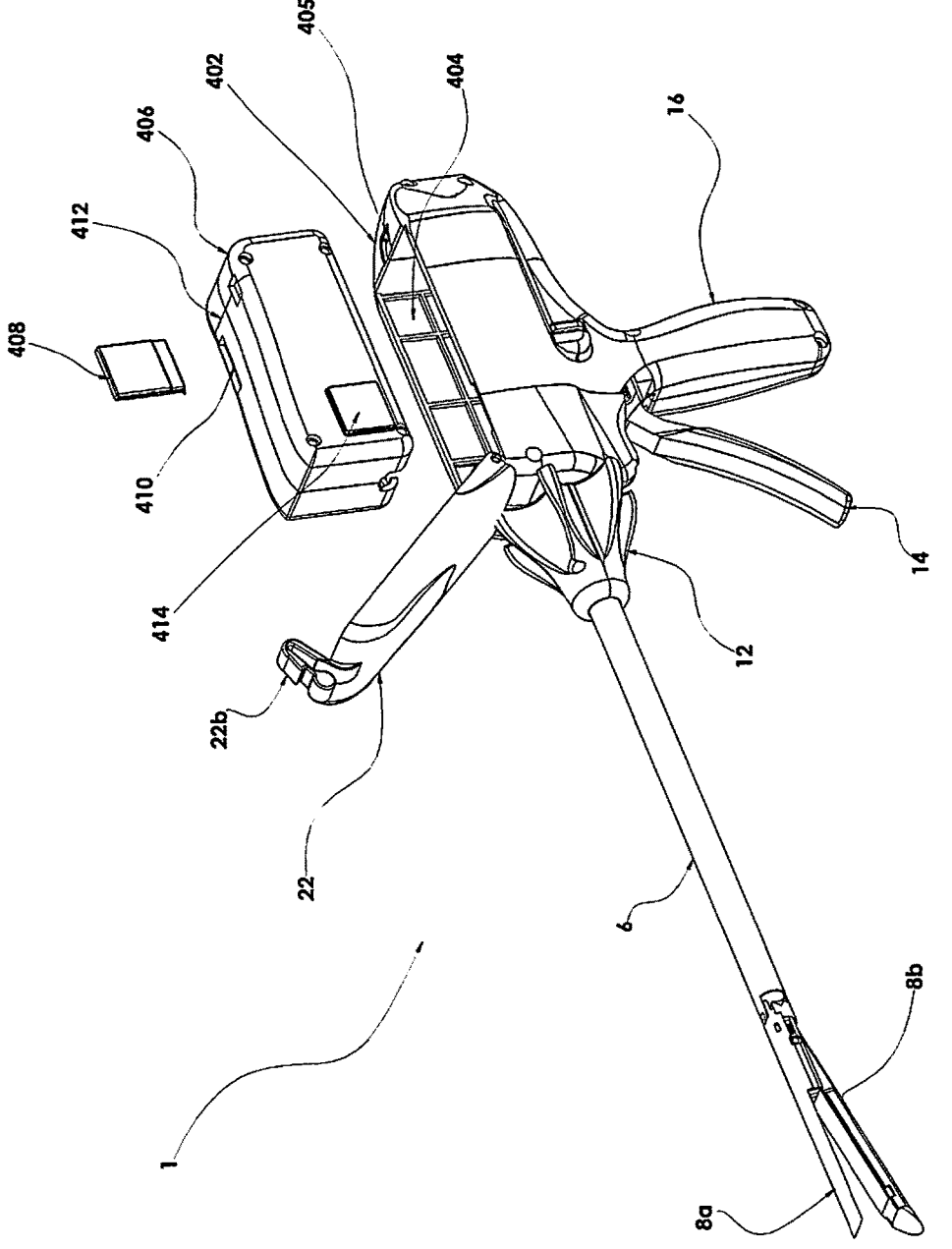
FIG. 35 is a perspective view of an alternate embodiment of the surgical instrument of the present invention having a replaceable battery pack.

Turning first to the embodiment of FIG. 35, the power pack 406 has an upper surface 412 having a cavity 410 to slidably receive card-like battery pack 408. Battery pack 408 is slid into the cavity and engages a contact within the housing to enable actuation of the motor to power the drive mechanism within the power pack 406 to effect staple firing and/or jaw articulation in the same manner as described above (via engagement by the flag or yoke). Power pack 406 is placed into the cavity 404 of housing 402 in a similar manner as described above, e.g., top loaded into the compartment, and the hinged cover 407 is closed to seal the power pack 406 from the external environment. Cover 407 differs from cover 22 in that it includes a spring loaded latch 409 received in latch cavity 405 of housing 402 to retain the cover 407 in the closed position. The latch 409 is released by pressing latch 409 to disengage the latch 409 so the cover 407 can be opened to access the power pack 406. Raised surface (tab) 414 on one or both sides of the power pack 406 aligns with a recess in the compartment 404 for alignment of the power pack 406 during insertion.

In use, the battery pack 408 can be aseptically preloaded in the power pack 406, either by a user or packaged with the battery pack 408 preloaded, and the power pack 406 is aseptically preloaded into the surgical instrument. During a surgical procedure, in the event of a battery failure, the cover 407 can be opened and the power pack 406 can be removed intraoperatively from compartment 404, the battery pack 408 removed from cavity 410, a new (second) charged battery (battery pack) aseptically placed in cavity 410 and the power pack 406 with the replacement battery pack reloaded into compartment 404. In an alternative use, during a surgical procedure, in the event of a battery failure, the cover 407 can be opened and with the power pack 406 remaining in compartment 404, the battery pack 408 is removed from cavity 410 of the power pack 406 and a new (second) charged replacement battery (battery pack) aseptically placed in cavity 408 while the power pack 406 remains loaded (positioned) within the compartment 404 of the surgical instrument.

Figure 36:
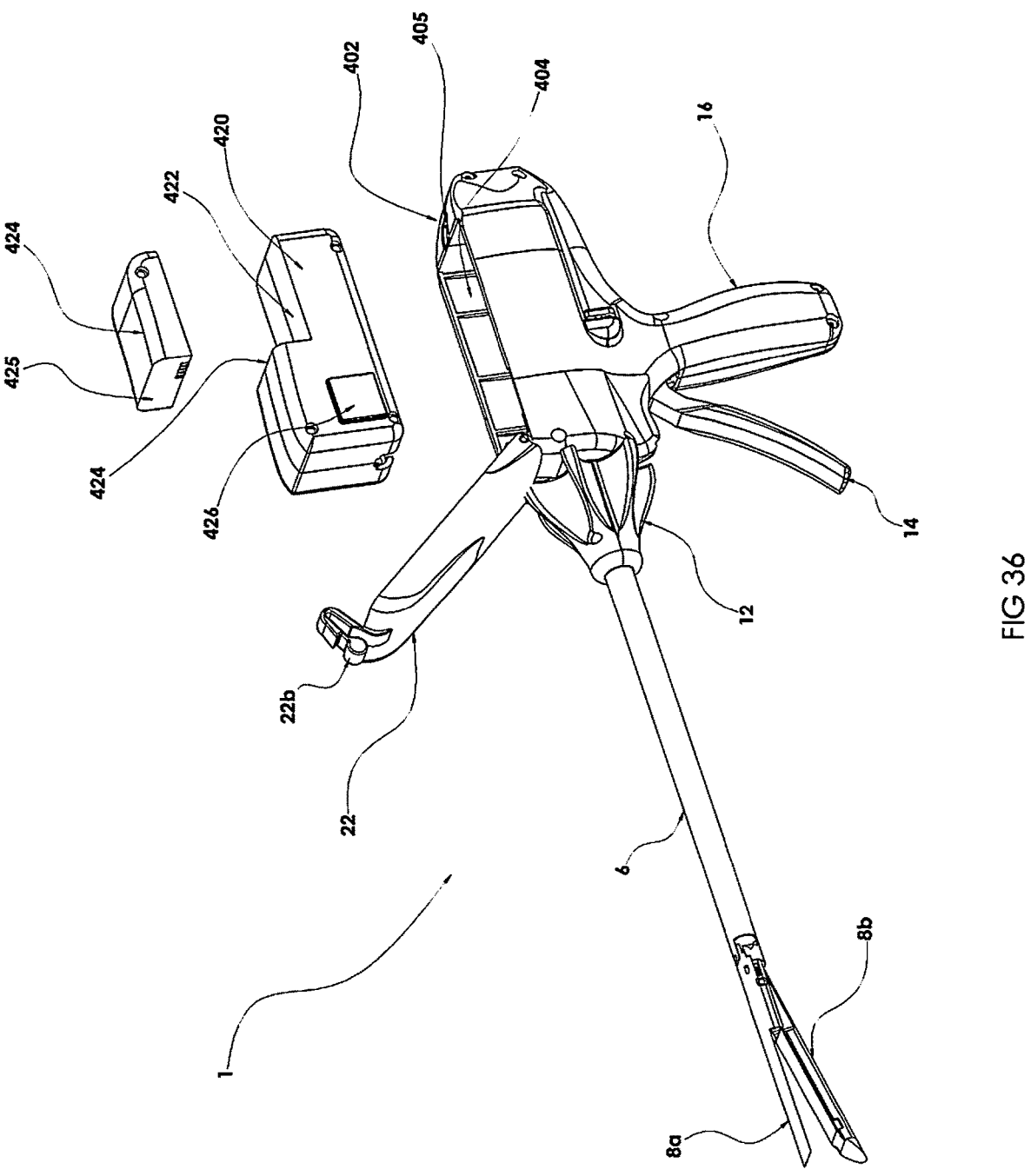
FIG. 36 is a perspective view of another alternate embodiment of the surgical instrument of the present invention having a replaceable battery pack.

In the alternate embodiment of FIG. 36, the stapler 1 is the same as in FIG. 35, the difference being the power pack and battery pack. More specifically, power pack 420 has an outer upper surface 422 extending proximally from wall 428, on which the battery pack 424 is mounted. Wall 425 of battery pack 424 can be placed in abutment with wall 428, and the power pack 420 and battery pack 424 can be dimensioned so that the battery pack 424 becomes part of the outer contour of the power pack 420, e.g., the upper surface 427 of the power pack can be substantially flush with the upper surface 429 of the power pack 420, although in alternate embodiments the upper surface can be below or above the upper surface 429. Power pack 422 can have an alignment tab 426 on one or both sides to aid insertion/alignment. The battery pack 424 can include an engagement feature 420 interacting with the power pack/to secure the battery pack 424 on the power pack 420.

In use, as with power pack 406 described above, the battery pack 420 can be preloaded, i.e., pre-mounted, onto the power pack 406 (by the user or prepackaged) and can be removed and replaced with another (second) charged battery (battery pack) during a surgical procedure by first removing the power pack 406 from the compartment 404 of stapler 1 or alternatively the battery pack 420 can be removed from the power pack 406 and replaced by another charged battery pack while the power pack 406 remains in the compartment 404.

Figure 37A:
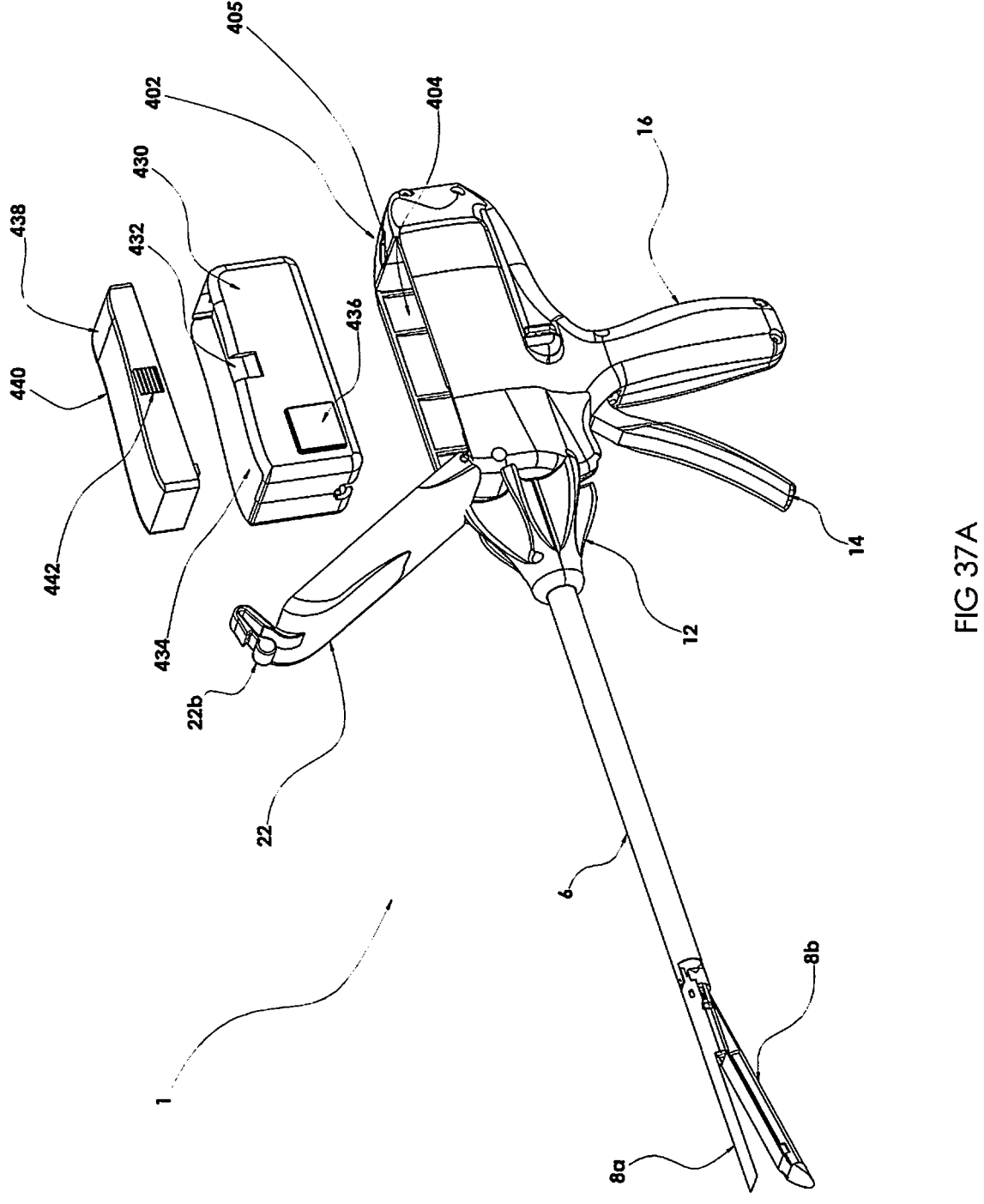
FIG. 37A is a perspective view of another alternate embodiment of the surgical instrument of the present invention having a replaceable battery pack.
Figure 37B:
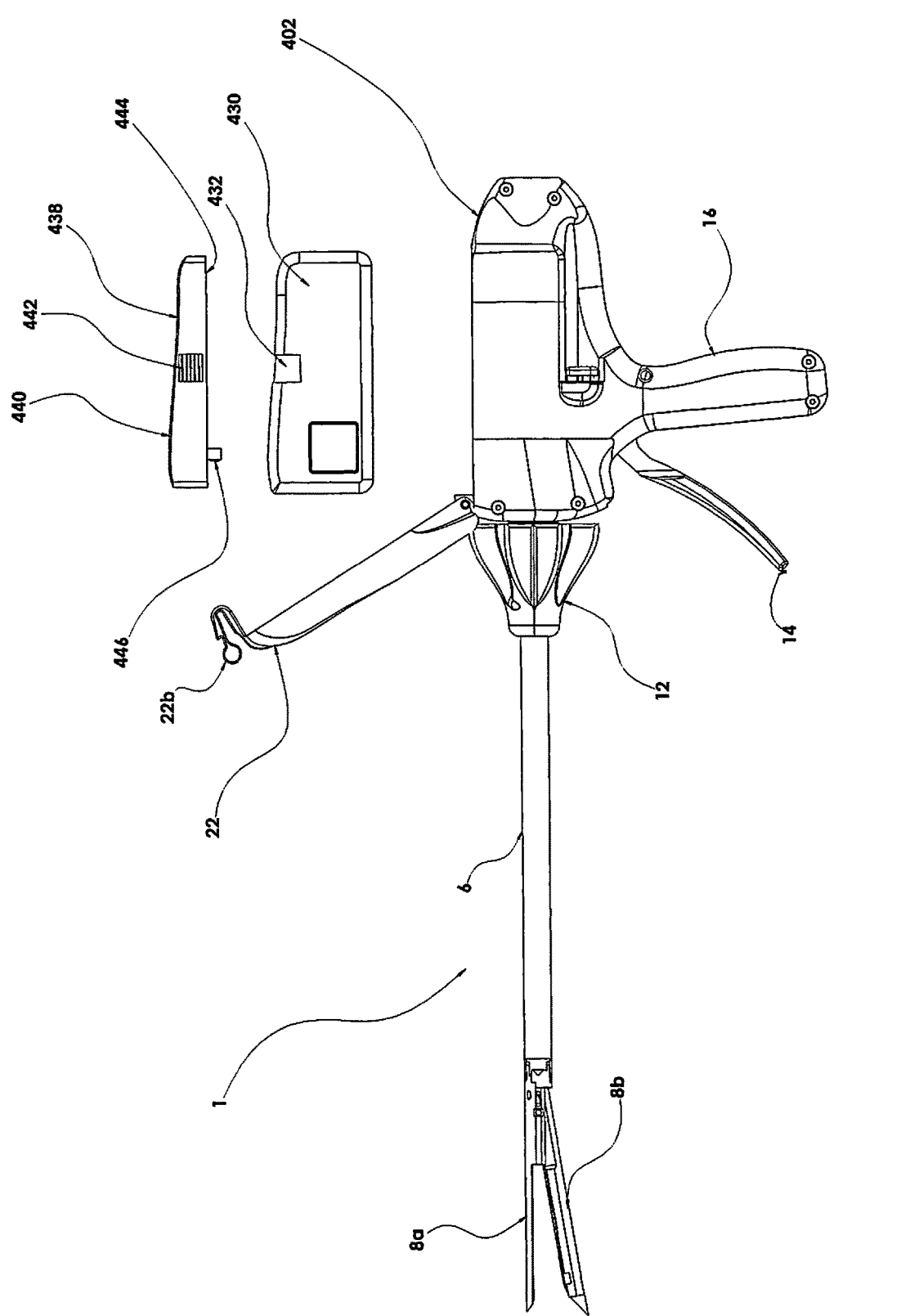
Figure 37C:
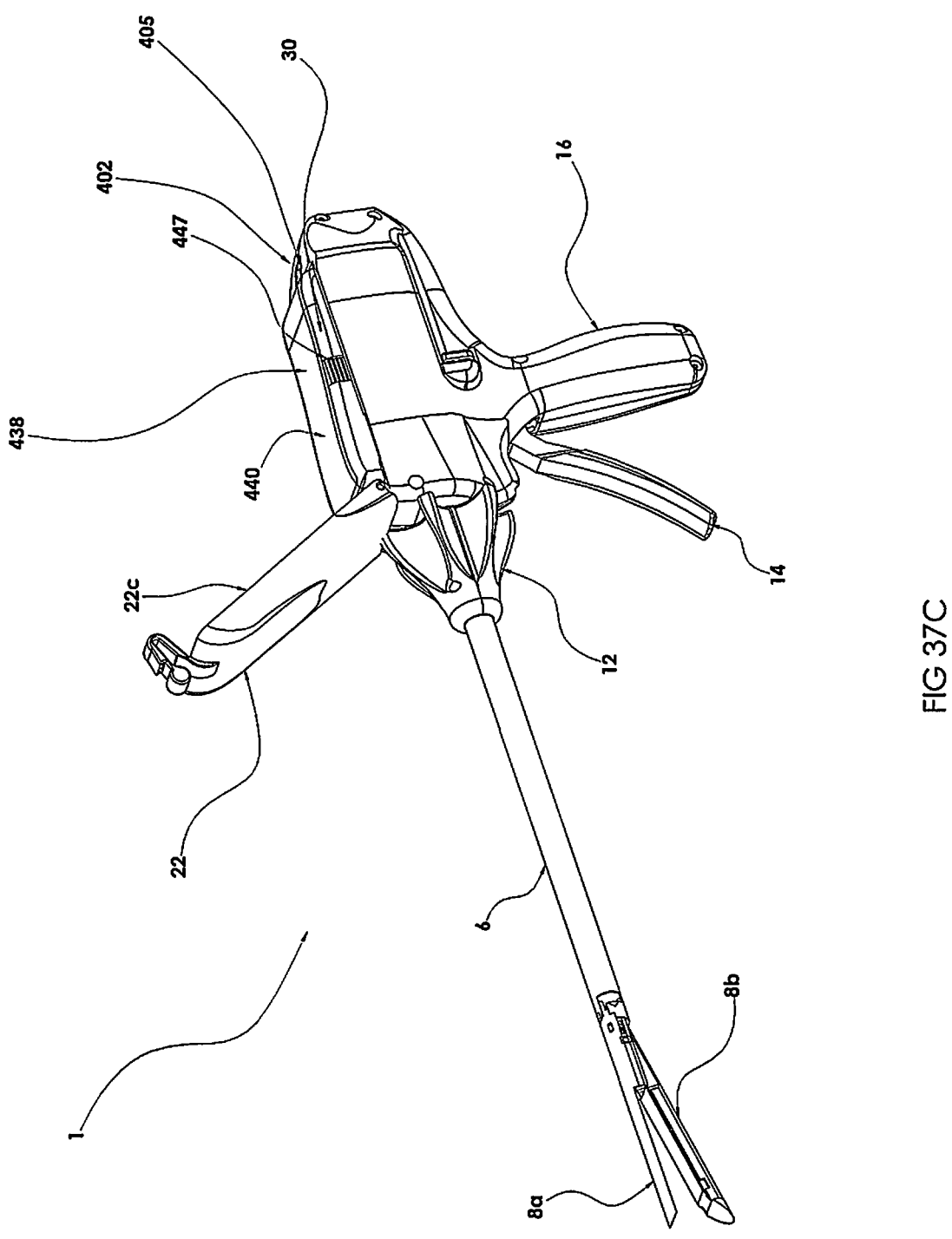

In the alternate embodiment of FIGS. 37A-37C, the battery pack 440 is mounted into a cavity (receptacle) in the power pack 430. Note the stapler 1 of FIGS. 37A-37C is the same as in FIG. 35, the difference being the power pack and battery pack. Power pack 430 has a cavity 432 extending along its length dimensioned to receive battery pack 440. The power pack 430 and battery pack 440 can be dimensioned so that the battery pack 440 becomes part of the outer contour of the power pack 430. Irregular gripping surface or tab 442 on side wall 443 of battery pack 440 is received in cutout 432 on the side wall of power pack 430. The gripping surface can be grasped by the user to facilitate removal as the battery pack 440 is removed from the power pack 430. In some embodiments, a gripping surface or tab like surface 442 can also be provided on the opposing side wall (received in another cavity like cavity 432 positioned on the opposing side) for facilitating grasping both sides of the battery pack 440 for removal from the power pack.

In the loaded position, the battery pack can protrude slightly above the plane of the top edges 404*a* of the compartment 402 as shown in FIG. 37C or alternatively can be flush or below the plane of the compartment edges 404*a*. In any case, the power pack and mounted battery pack 440 are placed sufficiently within the compartment 402 so that the cover 407 can be completely closed to seal the power pack 430 and battery pack 440 from the external environment.

In use, the battery pack 440 can be preloaded in the power pack 430, either by a user or packaged with the battery pack 440 preloaded. During a surgical procedure, in the event of a battery failure, the cover 407 can be opened, power pack 430 removed from compartment 404, the battery pack 440 removed from cavity 434, a new (second) charged battery (battery pack) aseptically placed in cavity 434 and the power pack 440 with a replacement battery pack reloaded into compartment 404. In an alternative use, during a surgical procedure, in the event of a battery failure, the cover 407 can be opened and with the power pack 430 remaining in compartment 404, the battery pack 440 is removed from cavity 434 of the power pack 440 and a new (second) charged battery (battery pack) aseptically placed in cavity 434 while the power pack 430 remains loaded (positioned) within the compartment 404.

Note the battery packs disclosed herein can include custom cells or alternatively off the shelf batteries. The use of the term battery pack as used herein encompasses different types of batteries and different housings for the batteries which are mounted on or inserted either fully or partially into the power pack housing (which contains the powertrain therein) to operatively connect with the motor in the power pack.

The battery packs can be retained, e.g., locked, in or on the power pack housing in various ways such as a latch, spring loaded engagement, frictional engagement, interlocking tabs, etc., and such mountings can also include a release button for disengaging/removing the battery pack from the power pack.

As noted above, the power pack 90 can be used with the other staplers disclosed herein, e.g. circular staplers, linear staplers, as well as other instruments wherein two powered functions are desired. The first motor assembly can effect linear motion of a first elongated member to effect a first function of the stapler, e.g., clamping, articulation, firing, and the second motor assembly can effect linear motion of a second elongated member to effect a second different function of the stapler, e.g., clamping, articulation, firing. In the embodiment of FIG. 14A, one function is articulation and another function is staple firing. Note the power pack 90 can also be used with surgical instruments other than surgical staplers such as those illustrated in FIGS. 33A and 34A.

FIGS. 38-41 illustrate an alternate embodiment of the stapling instrument having an encoder with switching devices to effect articulation and firing. Operation of the instrument is illustrated schematically in the concept diagrams of FIGS. 38-40.

Figure 38:
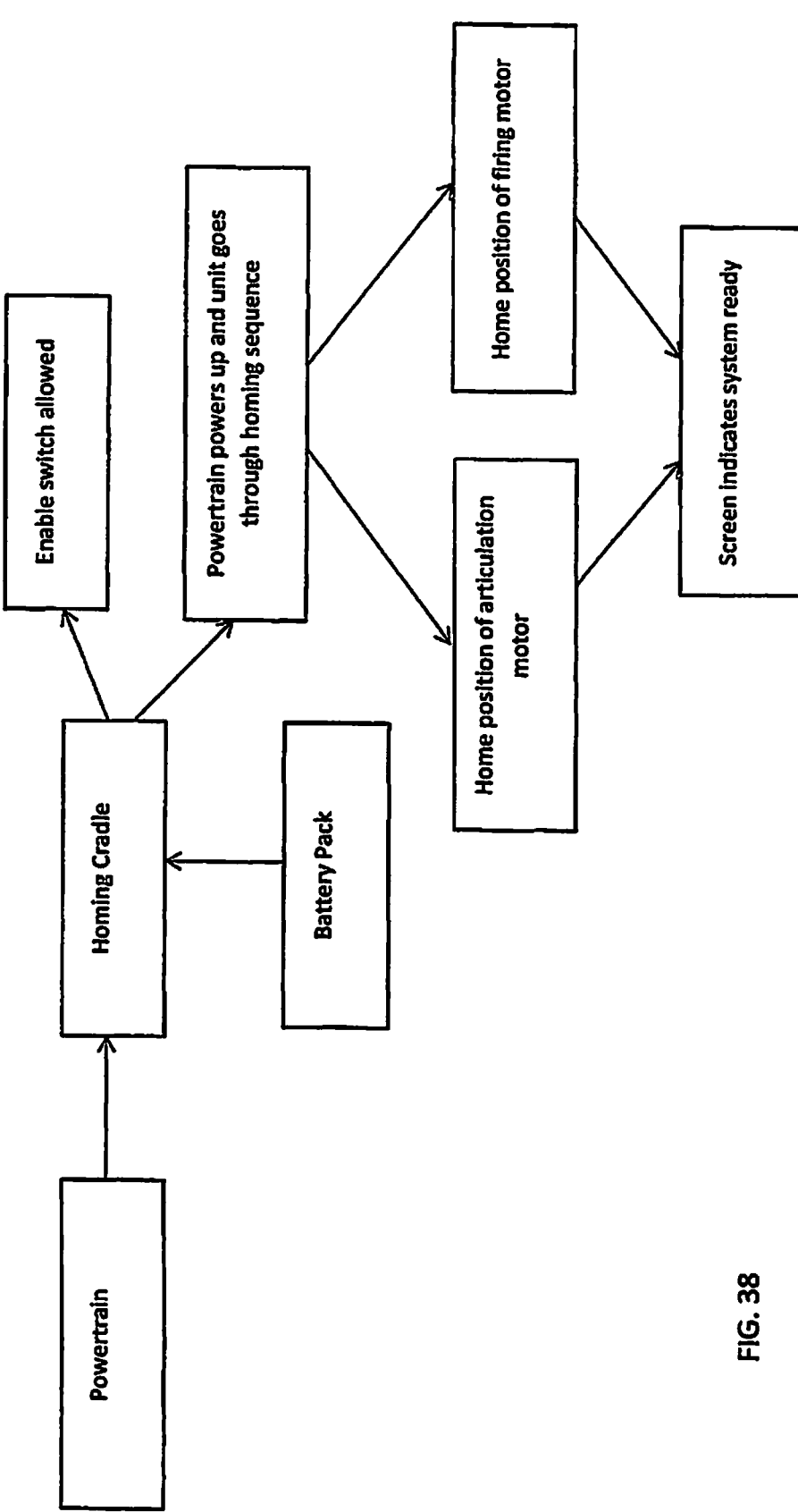

Initially, with reference to FIG. 38, the powertrain (also referred to herein as the power pack) is inserted into a homing cradle. The powertrain has an external homing switch engaged with the homing cradle. The replaceable battery can be inserted into the cradle either before or after the battery is loaded into the powertrain. A CD to DC converter can be provided to boost battery voltage from for example 7.6V to 18V. A safety (thermosensor) can be provided on the battery pack to prevent overheating. For example, a battery life indicator (e.g., a gas gauge) can be provided as part of a battery management system to prevent battery overheating. A circuit board in the charger monitors the thermosensor so if the temperature exceeds a predetermined threshold, it automatically shuts down the charge to the battery. Indicator lights providing battery status can be provided. Within the homing cradle, the enable switch is allowed. The powertrain powers up and the unit goes through a homing sequence so that the articulation motor and the firing motor are both in the home position. A screen can be provided on one or more of the powertrain or the cradle to indicate the articulation and firing are in the home positions and the system is ready for use (enabled), i.e., ready for loading into the surgical instrument compartment for powering the surgical functions of the instrument. The switches are enabled within the homing cradle but cannot be actuated within the cradle. A screen/window can also be provided on the instrument, e.g., instrument housing, to indicate the home position.

Figure 39:
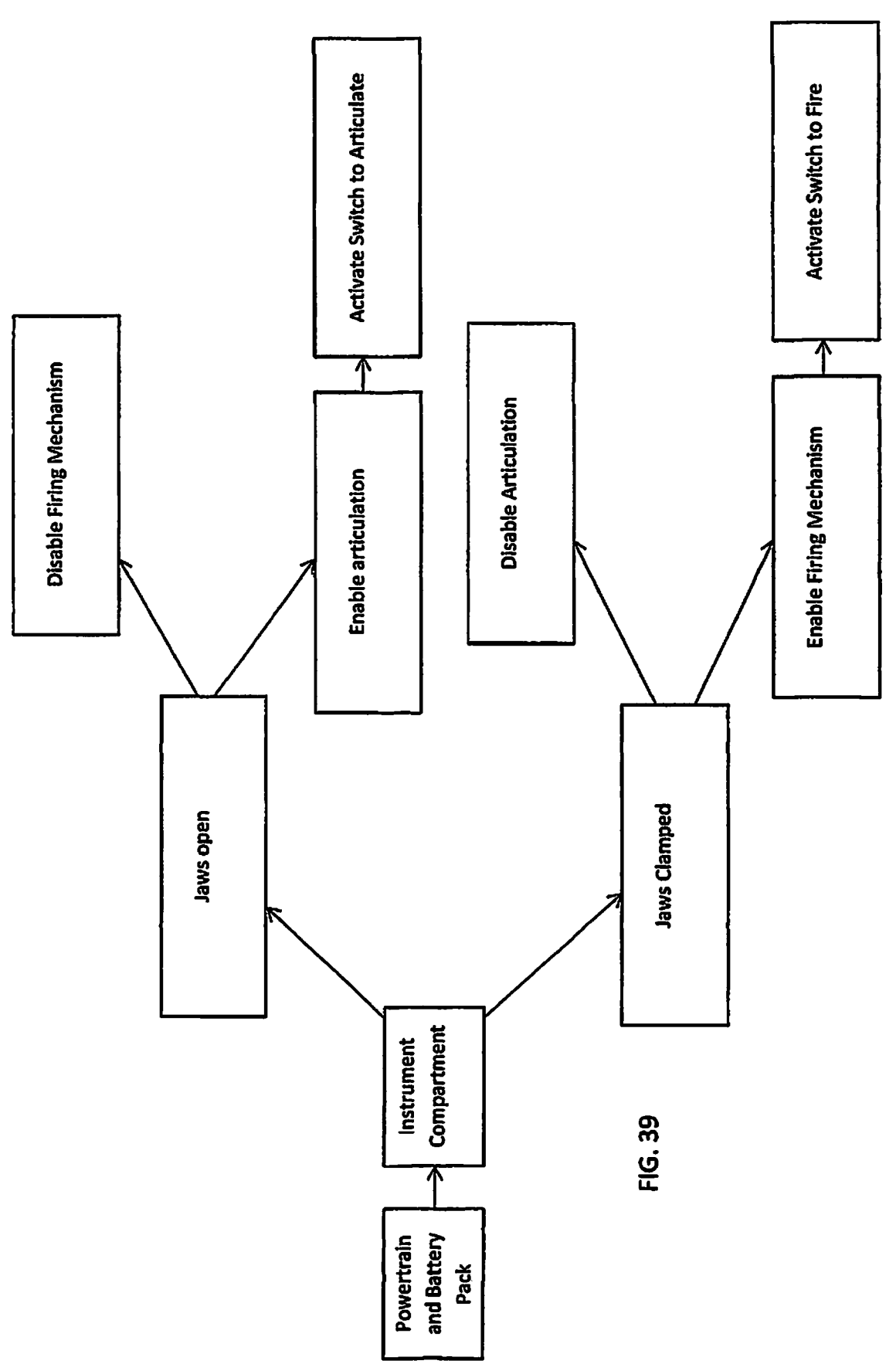

FIG. 39 illustrates schematically how the surgical functions are enabled/disabled based on the position of the instrument jaws. This is achieved through software in the powertrain (power pack). With the powertrain loaded in the compartment, if the instrument jaws are open, the firing mechanism, i.e., the firing switch, is disabled. This ensures that the staples cannot be advanced from the staple receiving jaw and the knife bar cannot be advanced distally unless the jaws are properly clamped on tissue. In the open position of the instrument jaws, the articulation mechanism, i.e., the articulation switch, is enabled so that the cartridge and anvil jaw assemblies can be articulated by actuation of the articulation motor to various angles with respect to the longitudinal axis of the surgical instrument.

With continued reference to the diagram of FIG. 39, with the powertrain loaded in the compartment, if the instrument jaws are moved to the closed (tissue clamping position), the firing mechanism, i.e., the firing switch, is enabled. This enables the firing motor to be actuated so the firing mechanism and cutting blade can be advanced distally to fire the staples and cut tissue clamped between the jaws. In the closed position of the instrument jaws, the articulation mechanism, i.e., the articulation switch, is disabled so that the cartridge and anvil jaw assemblies cannot be articulated.

The foregoing is shown in the stapler of FIGS. 41A and 41B, wherein in the open position of the jaws (FIG. 41A), the manually actuated clamping handle 514 is in the open position with the engagement surface 510 spaced from the switch 512. When the clamping handle 514 is moved to the closed position (FIG. 41B), the engagement surface 510 comes into contact with the switch 512 to complete the circuit for activation of the firing mode. In this clamped position, the firing button 518 can be actuated to effect staple firing. With the engagement surface 510 spaced from the switch 512, the circuit is open such that actuation of the firing button 518 will not actuate the motor and thus not initiate firing. Alternatively, the switch can be in the "closed position" in both handle positions with the software detecting the clamped position of the handle.

The steps for loading the powertrain and using the instrument will now be described in conjunction with the flow chart of FIGS. 40A-40C. The powertrain is inserted into the homing cradle followed by insertion of the battery into the homing cradle. This moves the articulation and firing motors into the home position. If the screen indicates completion of the homing sequence, i.e., ready for use, the powertrain and charged battery are removed from the cradle and placed into the compartment of the instrument housing as described above with respect to the other staplers. Once the powertrain is properly seated in the compartment, the compartment cover can be closed which then enables subsequent actuation of the switches. If not properly seated, the switches are not enabled. In some embodiments, as described below, closing of the cover automatically activates an enable switch.

To use the stapler, the clamping handle is closed to move the jaws to the closed position for insertion through the trocar. Once inserted, if articulation is desired, the handle is unclamped to move the jaws to the open position and the articulation switch, e.g., a rocker switch or other switches preferably accessible on either side of the instrument, is pivoted to move the jaws from the 0 position to the left or right. The encoder via a motor count detects the articulated position of the jaws which in some embodiments can be visually displayed on an instrument or power pack screen. After reaching the articulated position of the jaws, tracked via the motor count, the articulation switch is released to maintain the jaws in this position. In some embodiments a double pump articulation switch can be utilized.

Next, the jaws are clamped via the manually actuated handle, which enables activation of the firing mode. With the jaws closed, the firing switch is actuated, to advance the firing rod and knife bar to apply staples and cut tissue. A motor count tracks the position of the firing rod. That is, the motor encoder detects motor location within a full stroke, i.e., informs what portion of the cycle (revolutions) of the complete cycle the firing mechanism is in along the firing stroke. The count correlates to the amount of spins of the driveshaft, effectively controlling the distance of the drive mechanism, e.g., collar. The number of revolutions is tied into a predetermined (selected) speed and a predetermined time. The motor speed can be automatically adjusted during use. Note as the motor operates, if there is a spike in amperage, the central processing unit will slow down the motor rpm, and the time cycle will be adjusted accordingly, along with the encoder detection of the full stroke.

In some embodiments, to effect firing, the firing trigger needs to be pressed a first time as a pre-actuation mode and then pressed a second time to advance the firing rod and knife bar. After application of staples, the firing rod and knife bar are retracted to the home position. The articulation switch is then actuated to return the articulation motor and thus the jaws to the home position. The jaws are closed by the clamping handle and the instrument is removed from the patient's body through the trocar. Note an abort switch can be provided to reverse motor rotation to retract the firing mechanism and knife bar during the procedure.

After removal of the instrument, the jaws are open and the spent cartridge is removed. If additional staples are required a fresh cartridge is loaded into the cartridge receiving jaws and the instrument jaws are closed and the instrument is inserted through the trocar (returning to block 7 of the diagram of FIG. 40—"manually pull handle to clamp jaws and insert through trocar.")

As noted above, in some embodiments, a switch is located on the power pack which is actuated by the instrument cover when the cover is closed. This is shown in FIGS. 77-82B. Instrument 900, like instrument 61 of FIG. 14A described above, has an elongated member 902, a pair of jaws 907, 905 at a distal portion and rotation knob 914. Pivotable handle 924 is movable toward stationary handle 922 to close the jaws for clamping onto tissue. A clamp release button 926 releases the clamp lever to open (unclamp) the jaws, Pivotable cover 912 has a projection or boss 934 extending at a proximal region which engages activation (power enable) switch 932 on the power module (power pack) 950 when the cover 912 is moved from its open position of FIG. 77 to the closed position. The power module 950 can be the same as power pack 700 discussed below or any of the other power packs disclosed herein. In this manner, when the motors within the power pack cannot be activated unless the cover 912 is in the closed position. Power pack 950 includes a screen 952 like screen 704 disclosed herein. A pair of articulation buttons/switches 930, symmetrical about the axis, are disposed on each side of the instrument housing 920 to articulate the jaws 905, 907 in either direction, e.g., button 905 articulates the jaws to the left and the button on the opposing side (not shown) articulates the jaws to the right. In alternate embodiments, the opposite buttons can articulate the jaws to left and right. Once the cover is closed and boss 934 engages the power enable switch 932, the firing mechanism can be activated via switch 928 which in communication with the motor operatively connected to the drive mechanism within the power pack. The electromechanical switch 934 is mounted to PCB board which is fixed within the power pack which communicates with the CPU within the power pack.

The cover can have a seal about its periphery and/or a seal around the periphery of the opening to the compartment can be provided, as discussed above, to seal the power pack within the compartment to prevent entry of contaminants.

Below is a chart summarizing the safety mechanisms of the surgical instrument in accordance with some embodiments:

When the motor is actuated to rotate the deployment screw 818 as described herein to advance the collar 756 and firing mechanism, the static (fixed) code wheel 814 reads the discrete positions of the encoder and sends a signal to the CPU within the power pack indicative of such reading/ position. Such rotation count determines the location of the firing mechanism and thus the location of the I-beam firing the staples from the cartridge. Note the number of discrete positions can vary and in some embodiments there are 64 discrete positions.

In the alternate embodiment of FIGS. 74-76B, encoder 846 is fixably attached to collar 846 of deployment screw 848. (Deployment screw 848 and collar 846 are otherwise the same as screw 818 and collar 830). As the collar 846 moves axially distally when the deployment screw is actuated by the motor as described in the embodiments above, the positon of the collar 846 is detected by scale 850. Scale 850 is attached to the chassis 856 of the power pack housing, and runs along the length of the stroke. The detected axial position of the encoder is sent to the PCB within the power pack for determination of firing mechanism location. Note in this embodiment, the encoder 846 us positioned in an indentation at a proximal end of the collar 852 adjacent nut 854, but can alternatively be mounted to the collar in other ways/locations.

| Pre-loading of power train into instrument | Can't activate switch when powertrain in cradle |
| | Thermosensor in battery pack monitored by electronics in charger to shut down charger if overheating |
| | Viewable screen indicates ready/not ready condition of powertrain |
| | Can't activate switch if powertrain not properly loaded and instrument compartment cover not fully closed |
| | Loading into instrument prevented if firing and articulation not in home position |
| Once powertrain loaded | Opening of jaws breaks circuit to disable firing mode |
| | Closing of jaws disables articulation mode |
| | Cant actuate firing switch if articulation switch activated |
| | Can't actuate articulation switch if firing button activated |
| | Encoder following error if resistance in firing |
| | Encoder detects proper functioning of motor |
| | Encoder detects position and completion of firing stroke via motor count |
| | Encoder detects articulated jaw position via motor count |
| | Fire button needs to be depressed first as initial step before firing |
| | Copycat position so can resume where left off if power pack replaced |
| | Firing abort button to cease advancement of firing rod and retract to home position |
| Removal of Powertrain | Can't remove powertrain if articulation driver not in home position |
| | Can't remove powertrain if staple driver not in home position |

FIGS. 68-76C illustrate two embodiments utilizing an encoder to measure either rotational movement of the ball screw (FIGS. 68-73) or linear movement of the collar/drive mechanism (FIGS. 74-76B). This provides a failsafe if the motor loses communication with the CPU.

Turning first to FIG. 68, the deployment screw 818 has a collar 830 extending therefrom which functions like collar 94 of the deployment screw of FIGS. 22A-22D in that it forms an engagement member for engaging and advancing the firing rod (firing mechanism) in the housing of the surgical stapler. This collar configuration is similar to that of collar 756 of FIG. 59A of application Ser. No. 16/792,110, filed May 15, 2020, the entire contents of which are incorporated herein by reference.

Deployment screw 818 differs from these deployment screws in that it supports an electromechanical encoder 810. More particularly, the encoder 810 is mounted to encoder holder 812 which has a post 813 inserted into opening 826 at a proximal (back) end of screw 818. Other ways to mount the encoder to the screw are also contemplated. Code wheel 814 is mounted in opening 816a of proximal chassis 816.

Note an encoder similar to that of FIG. 68-73 or 74-76B can also be utilized with the articulation screw to determine the positions of the articulation mechanism and thus the articulation angle of the jaws. The encoder could be mounted for example to the articulation screw or collar.

A screen can be provided on the top of the powertrain to indicate the firing, clamping and/or articulation modes/ positions. The screen can be visible through a clear window in the housing of the instrument. An example of the screen is shown in FIGS. 55 and 57A wherein screen 704 is on a proximal portion of the housing 706 of power pack 700. The screen in this embodiment angles toward the user. It is covered when instrument compartment cover 702 is closed, and cover 702 has a transparent portion or window (such as window 913 of cover 912 of FIG. 79) so that the screen 704 is visible when the cover 702 is closed. As can be appreciated, the screen can be provided in other positions and portions of the power pack 700. The screen 704 can show various features and parameters via numeric designations light or other indicators. For example, the screen can show one or more of firing position, articulation position (degree of articulation), the type (staple size and length) of cartridge selected, battery life, clamping position, tissue range, confirmation of home positon of articulation mechanism and/or firing mechanism when loaded and/or when ready for removal from the instrument compartment, confirmation that the cover is in the fully closed position, and/or other conditions of the motor or other components of power pack or instrument.

In alternate embodiments of the present invention, the surgical instruments have features to aid staple size selection. These instruments can also provide motor speed adjustments to accommodate different tissue thicknesses.

These features include a measurement device such as a force gauge, a strain gauge pressure sensor or other gauges/sensors to measure one or more of i) the clamping force on tissue clamped between the instrument jaws; ii) the clamping pressure on the tissue clamped between the jaws and/or iii) tissue density within the jaws of the instrument. The gauges/sensors can be placed on various locations of the instrument, including proximal and distal portions. Alternatively, the sensors/gauges can be placed on the loadable power pack. These variations are discussed in detail below with reference to FIGS. 42A-45F. Note that the instruments of FIGS. 42A-44C show several gauges/sensors within the instrument to illustrate examples of possible locations for the gauges/sensors. It is not intended that all of the depicted gauges/sensors need to be in a single instrument as it is contemplated that only one of the gauges/sensors is in the instrument. However, it is also contemplated that more than one gauge/sensor can be provided in the instrument.

In some embodiments a screen is located in the handle housing (see screen 613 of FIG. 42D) or on the power module to provide a visual indicator to the clinician of the measured parameter(s). For example, clamping forces, tissue or clamping pressures, and/or tissue densities measured or calculated by the sensors/gauges as disclosed herein can be displayed on the power module TTF, LCD or Human Machine Interface screen to give real-time feedback to the surgeon. This real-time feedback can be used along with tactile manual clamping. This can induce faster learning for the surgeon on acceptable tissue being clamped.

Turning first to FIGS. 42A-42F, several different possible locations for the force measurement device are provided. For brevity of the drawings, as noted above, FIG. 42D and identical FIG. 43A show in a single drawing multiple possible locations for the gauges/sensors. Note only one of these locations can be utilized or alternatively, gauges/sensors can be placed on more than one of the identified locations, as well as in other locations. These locations can be on a movable part related to clamping of the jaws or on a joint where there is a transfer of force. As used herein, the term measurement device will be used to denote gauges or sensors or other devices to measure one or more of clamping force, clamping pressure, tissue density and/or other parameter.

The instrument 600 of FIGS. 42A-43C is identical to the instrument of FIG. 14A described above except for the measurement features and the cam pin/slot arrangement for opening and closing the jaws.

The cartridge jaw 607 is shown in the open position in FIGS. 42A, 42B and 42D, spaced from anvil (or anvil jaw) 605, i.e., the cartridge received in cartridge receiving channel of cartridge jaw 607 is spaced from anvil forming surface 605a of anvil 605. The anvil forming surface 605a deforms the staples fired from the cartridge jaw 607. In the open (unclamped) position, the clamp pin 604 is at a distal end of clamp pin slot 603 (see FIG. 51). In this position, the clamp rod (clamp shaft) 620 and the clamp laminates 616 are in the distal position. Clamp laminates 616 connect clamp rod 620 to the distal clamp adapter 622 via hook engagement of hook 616a at the distal end of clamp laminates 616 and a hook at the proximal end of the clamp adapter 622. The clamp laminates 616 can be fixedly attached to the clamp rod 620 and clamp adapter 622 or alternatively floatably attached to these components. The flexibility of the clamp laminates 616 allows for articulation of the jaws 605, 607.

Upon manual clamping of the handle 609, i.e. movement toward stationary handle 611, to effect closure of the cartridge jaw 607, the clamp rod 620, which is operatively connected to the clamping handle 609, is pulled proximally, thereby pulling the attached clamp adapter 622 proximally. This moves the through pin 604 which is attached to clamp adapter 622, proximally within the cam slot 603 to move the cartridge jaw 607 toward the anvil jaw 605 to a clamped (closed) position as the cartridge jaw 607 pivots about pivot pin 624. The clamp pin 604 translates in the slot 603 relative to the location of the clamp rod position. The cartridge jaw 607 rotates around the pivot pin 624 relative to the location of the clamp pin 604 in the cam slot. The pin/slot arrangement is shown in FIGS. 49-51. Further details of the clamp pin/slot structure for closing and opening the jaws are described in application Ser. No. 16/792,110 and provisional application Ser. No. 62/900,146, filed Sep. 13, 2019, the entire contents of which are incorporated herein by reference.

In the embodiments of FIGS. 42E and 42F, the measuring device is placed distal of the handle housing 602. More specifically, in FIG. 42E. the load pin (clamp pin) 604, which is movable within the cam slot 603 as described above based on the axial movement of the clamp rod 620, measures force as the cartridge jaw 607 is moved to the closed position.

In an alternate embodiment, the load cell 606 is located in the distal clamp adapter 610. The load cells herein can form transducers for converting force into a measurable electrical signal. The distal clamp adapter 610 is actuated, i.e., moved axially, by the clamp laminates 616 which are connected to the clamp rod 620 which is movable to close and open the cartridge jaw 607. Note the laminates have slots which interact with the wall of the clamp rod 620 to move with the clamp rod, thus they are floatably connected to the clamp shaft. The load cell 606 is shown located at a proximal portion of the clamp adapter 610 where it is hooked to the clamp laminates 616, however it could be located at other regions of the clamp adapter 610. Axial movement of the clamp rod 620 moves the clamp adapter 610 to measure force as the cartridge jaw 607 is moved to the closed position.

In an alternate embodiment, the load cell 608 is located at a distal end of the clamp rod 620. It is shown at the distalmost end of the clamp rod 620, where the clamp rod 620 is hooked to the clamp laminates 616, but alternately can be located at other regions of the clamp rod 620. Axial movement of the clamp rod 620 measures force as the cartridge jaw 607 is moved to the closed position.

Note these load cells 604, 606 and 608 are positioned at the distal region of the instrument adjacent and proximal of the instrument jaws 605, 607 and proximal of the jaw pivot pin 624. Note load cell 604 provides an example of the measurement device on a load cell pin of the instrument; load cells 606, 608 provide an example of the measurement device on an axially movable part tied into jaw movement placed under load during clamping of the jaws on tissue. In this manner, clamping pressure or clamping force can be measured. Tissue density can also be measured.

The measurement device can alternatively be positioned further proximally of the jaws 605, 607 as shown for example in FIG. 42F. As shown, strain gauge 626 is located in the clamp shaft (clamp rod) 620 distal of the handle seal. That is, it is adjacent the handle 602 and distal thereof (and distal of the rotation knob 615). The clamp shaft 620 is movable axially to effect jaw opening and closing and thereby enabling gauge 626 to measure the force. Alternatively, the strain gauge can be located in a proximal region of the clamp shaft 620 proximal of the handle seal as shown for example in FIG. 43B discussed below.

In the foregoing embodiments, the measurement devices are positioned distal of the handle housing 602. In the alternate embodiments of FIGS. 43A-44C, the measurement devices are positioned in the handle portion with FIG. 43B illustrating the measurement device within the handle housing 602 and located in/on the axially movable clamp rod 620 and FIGS. 43C, 44B and 44C illustrating the measurement device on the manually actuated clamping handle or linkage.

More specifically, FIG. 43B illustrates strain gauge 630 positioned in the proximal region of the axially movable clamp rod 620 within the handle housing 602. Thus, the gauge 630 is positioned proximal of the handle seal. FIG. 43C illustrates a) strain gauge 638 located at the proximal end of the proximal clamp adapter 632; and b) strain gauge 634 located at the distal end of the clamp adapter 632. Proximal clamp adapter 632 is actuated by the clamp pivot plate 640. Strain gauge 634 is actuated by the proximal lip of the clamp rod 620 which is attached to proximal clamp adapter 632. The clamp adapter 632, clamp rod 620 and clamp pivot plate 640 are shown in the enlarged view of FIGS. 46-48.

In alternate embodiments, the load pin can be located at one or more of the pin locations on the clamp pivot plate 640. The pivot plate 640 is connected at one end to link or clamp yoke 645 via pin 642a and at the other end to clamp adapter 632 via pin 642c. Link 645 is connected to clamping handle 609 at the opposing end. Pin 642b, positioned between pins 642a and 642c connects to the adapter 632. Pins 642a, 642b, 642c form load pins for force measurement based on movement of the pivot plate during clamping of the jaws 607, 605 initiated by manual movement of handle 603. It should be appreciated that only one, only two or all three load pins 642a, 642b and 642c could be used in a single instrument. When clamping handle 609 is moved toward stationary handle 611, it causes movement of yoke 645 which pivots the plate 640 clockwise about pivot pin 642b to move the proximal clamp adapter 632 proximally to effect proximal movement of the clamp rod 620 which moves the cam pin 604 (FIG. 51) proximally within cam slot 603 to move cartridge jaw 607 toward anvil jaw 605 to clamp the jaws.

In the embodiment of FIG. 44A, the load pin 646 is located at the clamp pivot location, i.e., it connects handle 603 with the clamp yoke (link) 645. Movement of handle 609 effects movement of clamp yoke 645 as described above. In FIG. 44C, the load cell 648 is located in or on the clamp yoke 645 which can be in the form of a split yoke or complete yoke. It is outside the sterile portion of the handle housing 602a and is positioned on yoke 645 between the handle 609 and the pivot plate 640. The load cell can alternatively be positioned in other regions of the link 645.

As in the embodiments above, when provided on the instrument, the measurement device, e.g., the force gauge/strain gauge can be in line with the clamp linkage of the disposable instrument and/or in line with the clamp rod. It can be in the front of the clamp stroke, in the middle or in the back at or near the proximal clamp adapter. It can be inside or outside the handle housing. It can also be offset from the clamp rod such as below or side by side with the clamp bar. It could also be in line in the tube, distal of the handle so it does not need to rotate. It can also be inside the distal jaws of the instrument.

As noted above, the load cell can in alternative embodiments be located in the removable power pack as shown in FIGS. 45A-45F. The force gauge/strain gauge 654 is inside the reusable power module 652 and connected to the clamp linkage of the disposable instrument either through a split clamp linkage or at end of the clamp linkage stroke supported with a spring. As described above, the power module 654 is loaded into the compartment of the handle housing 602a and cover 656 seals the compartment. The measurement device e.g., load cell 654, within power module 652 measures clamp linkage linear movement/distance to determine the theoretical gap between the jaws for force measurement. That is, the load cell 654 mates with the clamp rod 620 as it drops into the linkage and translates with the clamp rod 620 during axial movement of the clamp rod 620 to measure clamp force. This can be used together with strain gauge/force gauge reading to calculate tissue density through the entire clamp stroke.

The force gauge is powered from power module and communicates with the power module microprocessor.

FIGS. 56-66B illustrate another alternate embodiment wherein the load cell is positioned in the power pack. In this embodiment, the deployment screw 710 and articulation screw 750 are supported by axial bearings and thrust bearings.

Thrust (axial) bearings and radial bearings on opposing ends of the screw 710 provide centering and axial alignment of the screw 710 during use. These thrust and radial bearings function in the same manner as thrust bearings 768, 780 and radial bearings 757, 782 of screw 754 of the embodiment of FIG. 59B of co-pending application Ser. No. 16/792,110, filed May 15, 2020, the entire contents of which are incorporated by reference as noted above. As shown. thrust bearing 716 is mounted at the distal end of screw 710 and thrust bearing 736 is mounted at the proximal end of the screw 710, proximal of collar 712, to resist any axial force applied to the rotating screw 710 and maintain its axial position. Radial bearings 724, 734 are provided to resist radial loads (forces that are perpendicular to the direction of the screw) and are located on the respective distal and proximal ends of the screw 710 with radial bearing 724 distal of thrust bearing 716 and radial bearing 734 proximal of thrust bearing 736. The thrust bearings 716, 736 are slip fit over the outer diameter of the deployment screw 710 (FIG. 59), at distal and proximal ends, respectively, and thus float relative to the screw 710. They are sandwiched together with the chassis. The radial bearings are press fit into openings in distal plate 744 and proximal plates as in application Ser. No. 16/792,110. The deployment screw 710 has a reduced diameter portion at the proximal end (FIG. 57C) and distal end (FIG. 57B) to form a shoulder 713 and 715, respectively, at the larger diameter portions which abut, i.e., contact, thrust bearings 736, 716, respectively. Thus, the thrust bearings 716, 736 can rotate freely within the housing, but are constrained by the steps (shoulders) of the ball screw 710 so they cannot move along the axis of the screw. The belt 723 and pulley 722 of the deployment (firing) mechanism are shown in FIG. 57B and are the same as in the foregoing embodiments.

Collar 712 has mounted thereto a pair of left and right track bearings 714 which function in the same manner as left track bearings 779 and a pair right track bearings 778, e.g., traveling along tracks in the 760, 762, described in detail in the Ser. No. 16/792,110 application, thereby preventing rotation out of the track as forces are translated linearly along shaft as the nut translates forward and backward. The tracks can be attached to or integrated (monolithic) with the chassis. The collar 712, like collar 756 of FIG. 59A of the Ser. No. 16/792,110 application includes a blade/tab extending inwardly from the wall which engages a circumferential recess (groove) in the deployment disk of the stapler which is attached to (or extends from) the firing rod of the stapler. In this manner, axial movement of collar 712 (via ball screw 710 when actuated by the motor) moves the deployment disk axially, the collar traveling along the respective left and right tracks (runners) via respective left and right bearings 714.

The deployment screw 710 includes a load cell or strain gauge 730 at the proximal end which is sandwiched between distal and proximal plates 738b, 738a. The deployment screw 710 further includes a load cell or strain gauge 720 at the distal end which is sandwiched between distal and proximal plates 718b, 718a. These load cells behind the thrust bearings measure force during firing. This can prevent the motor from being faulted. If the load cell detects an energy spike, a signal is sent to the microprocessor within the power pack 700 to slow down the motor.

The articulation screw 750 has distal thrust and axial bearings 762,763 (FIG. 62B) and proximal thrust and axial bearings 772,776 (FIG. 62C), similar to the thrust and axial bearings of the articulations screw 752 of FIG. 60A of the Ser. No. 16/792,110 application. Articulation screw has a load cell or strain gauge 760 (FIG. 62B) at the distal end which is sandwiched between distal and proximal plates 764b, 764a. The articulation screw 750 further includes a load cell or strain gauge 770 at the proximal end which is sandwiched between distal and proximal plates 774a, 774b. These load cells behind the thrust bearings measure articulation force. This can prevent the motor from being faulted. If the load cell detects an energy spike, a signal is sent to the microprocessor within the power pack 700 to slow down the motor.

The present invention can also provide a system that indicates to the user acceptable ranges for fastener application. Forces, tissue or clamping pressures, and/or tissue densities measured or calculated by the sensors/gauges as disclosed herein can are displayed on the power module TTF, LCD or Human Machine Interface screen on the instrument housing to give real-time feedback to the surgeon. Based on forces, measured pressure and densities pre-calculated from tissue testing which provide a baseline and maximum and interim values, the Human Machine Interface (HMI) screen will indicate if the measurement is within an optimal range for acceptable staple line outcome. This can be understood with reference to the diagram of FIG. 52. FIG. 52 shows the gauges can be provided a) in the clamp linkage (which includes components effecting mechanical clamping of the jaws (e.g., the manual clamp handle, cam pivot plate, adapter, clamp rod etc.) and/or b) in the power module, e.g., the component(s) therein tied into clamp rod movement; and/or c) in the instrument jaws. For (a) and (b) the clamp linkage movement, e.g., linear or pivotal movement is measured; for (c) the jaw movement toward the opposing jaw is measured. This can provide sufficient information for force determination. However, the information can also be used to determine tissue density as depicted in the optional last boxes of the diagram of FIG. 52.

FIG. 54 provides a flow chart depicting one embodiment of a system where the instrument determines if the staple size is appropriate based on the preset ranges where the values are pre-calculate/predetermined. More particularly, the jaws are clamped on tissue in the manners discussed herein and a parameter, e.g., clamping force, pressure and/or tissue density is measured utilizing one or more of the measurement devices disclosed herein. The measured parameter is compared by the microprocessor (e.g., a microprocessor in the power module) to the pre-set range. If the measured parameter is within the acceptable range, then firing is enabled and articulation is disabled. The microprocessor, based on the measured parameter, will then account for motor speed accordingly. That is, the microprocessor will control and adjust the motor speed, i.e., the microprocessor using AI will control or change the firing speed of the deployment motor based on the range detected whereas thin tissue will fire at faster speeds, medium tissue at nominal speeds and thick tissue will fire at slower speeds to enable tissue fluid to egress and reduce the forces on the stapler system.

If the measured parameter is outside the acceptable range, then firing is disabled and the instrument recommends, e.g., via a screen or other indicator on the instrument or power module, alternative size staple load either smaller or larger in size.

Note the Human Machine Interface screen will indicate whether it is in the acceptable range (thin/less dense/low pressure or medium/average density/nominal pressure or thick/more dense/high pressure). It is contemplated that in some systems, the optimal force/pressure/density of tissue would be staple load size agnostic and the same ranges would apply to all load sizes. In other systems, a staple size selector switch on the power module is provided so the forces/pressure/density would be staple load size specific and in certain applications provide more precise indications/motor controls.

In some embodiments, if a strain gauge reading records a force/pressure or tissue density within a predetermined range so the stapling function is indicated, i) the power module microprocessor will enable the firing sequence of the device to deploy staples and ii) the power module microprocessor will disable the articulation functionality of the device. On the other hand, if a strain gauge reading records a force/pressure or tissue density outside a predetermined range so the stapling function is not indicated, the power module microprocessor will disable the firing sequence of the device putting it in a lockout condition not allowing staple firing.

In some embodiments, the surgeon will be provided the option to override the device.

A gauge in the form of a cartridge can be provided in some embodiments so the surgeon can load and clamp on tissue prior to selecting a cartridge load size. This cartridge load gauge enables the surgeon to select a proper cartridge size without potentially wasting the wrong size cartridge. The surgeon will load the gauge (dummy cartridge) into the instrument. Then the surgeon palpates tissue with the jaws to determine staple height size and the device will indicate an optimal cartridge size such as via an output on the screen. The surgeon then removes the dummy cartridge and inserts the indicated staple cartridge in the cartridge jaw. These steps are shown in the flow chart of FIG. 53.

A clamp indicator in the window/can be provided to show where in the range the tissue falls based on the cartridge selected. The firing speed via AI (machine inference) can be controlled based on the cartridge selected and/or clamp indication measurements.

In some embodiments, the power pack can have a reader, such as an RFID reader, for detecting a type of staple cartridge prior to loading the staple cartridge in the instrument. The staple cartridge can have a code or tag, such as an RFID tag, and would be held adjacent the loaded power pack for detection of the type of cartridge, i.e., the size of the staples in the cartridge and/or the length of the arrays of staples within the cartridge. When detected, a signal is sent to the control module within the power pack to indicate which cartridge size is selected so the clamp force can be adjusted accordingly, and in some embodiments, indicated in the window/screen of the power module. The micropro- cessor can also preset the motor to correspond to the type of cartridge selected. The control module can be configured so that if a cartridge is loaded without its chip being read by the RFID reader, then the instrument cannot be actuated, e.g., cannot be fired. It can also be configured, so that the reader will detect if the cartridge has been fired (spent), i.e., devoid of staples, and if spent, the instrument cannot be actuated e.g., cannot be fired. The RFID tag can be on the plastic cartridge cover to minimize interference or assembled into the cartridge. Note alternatives to RFID readers to identify cartridge type, e.g., size, are also contemplated, with such identifiers communicating with the microprocessor in the power pack to adjust the clamping and/or firing parameters.

The logic circuit in some embodiments could be as follows: 1) load the power pack (in the home position) into the instrument compartment (the instrument cannot be actu- ated unless a power pack is loaded); 2) close the cover to enable the switch for articulation and the switch for firing (an enable mode); 3) select a cartridge and hold it adjacent the power pack to activate the load cells and to send a signal to the microprocessor confirming the cartridge has not been previously fired and to set the firing speed and adjust for other parameters, e.g., staple line length and firing stroke; 4) once all is active, place the cartridge in the instrument jaw; 5) the articulation switch and firing switch can be activated for performing the surgical procedure.

In some embodiments, a supercapacitor on the PCB can be provided to store enough energy to maintain micropro- cessor memory if the battery is exchanged or if the wrong size cartridge is utilized (wasted).

The load cell can be utilized in some embodiments for data acquisition to provide post procedure evaluation. In the manual option, the sales/OR staff will download case data from the power module via data transfer interface (e.g., USB). Data will be sent to HQ for trending and optimization for future cases. The feedback can be used to provide surgeons with ideal load selection. Note this would require staff present to input outcomes. In an alternative automatic option, the sales/OR staff will connect to the device via Bluetooth/wireless on their iPad or other mobile device and the data will be sent from the sales staff iPad (or other device) for trending and optimization for future cases. Other data collected and stored for such uses can further include biometrics, number of devices fired by the power pack; the length of the surgical procedures, forces generated, tissue information, operation of the stapling components and power pack components and other parameters of the tissue, surgical procedure, stapling instruments and/or power pack.

The foregoing measurement devices were discussed for use in surgical staplers. They can be used in open and endoscopic and laparoscopic staplers. However, they can also be used to measure pressure, force and/or tissue density in other instruments with clampable jaws such as graspers, energy devices, shears, clip appliers (where the measure- ment would prompt the surgeon to check clip closure based on force feedback of clip deployment).

Note the output can be digital. The output can be serial. It can be measured by voltage output.

A firing profile graph can be shown through HMI on the power module, visible through an instrument screen. High/ low lines as with a statistical process control chart (SPC) will allow the surgeon to maintain a "safe" firing speed. That is, the graph (see below) will provide an indication to the surgeons where they are during the stroke. For example, if force is too high, they may want to take action to reduce the force or pause firing. In FIG. 83, line A represents motor speed, line C represents the measured force and line B represents the optimal force. As shown, in FIG. 83, if the force spikes, the motor speed is slowed accordingly.

In the foregoing embodiments, use of the power pack of the present disclosure to fire staples such as in endoscopic linear staplers, open surgery linear staplers, circular staplers, as well as firing single clips or tacks were disclosed as examples. It should be appreciated that the power packs of the present disclosure can also be used to power functions of other surgical instruments. FIGS. 33A-34D illustrate two examples of such instruments.

In FIGS. 32A-32D an endoscopic scissors, designated generally by reference numeral 300, can receive and be powered by the power pack 18 (or power pack 90) of the present disclosure. Scissors 300 has a handle 306 manually pivotable towards stationary handle 304 to effect closing of the jaws, an elongated tubular portion 308 extending from the handle housing 302, and a pair of pivotable jaws 312 with cutting edges. Closing of the jaws 312 severs tissue between the jaws. The scissors 300 include a rotation knob 310 for rotation of the elongated portion (shaft) 308 to rotate the jaws 312. Power pack 18 is shown fully loaded (inserted) within the handle housing 302 and cover 303 is shown closed to seal the power pack 18 from the external environ- ment. As in the embodiment of FIGS. 1-12, the flag 42 extending from lead screw 36 engages a rod within the handle housing 302 operably connected to a jaw closing mechanism to effect movement of jaws 312 toward each other to sever tissue between the jaws 312. Either one or both jaws 312 can be movable.

In FIGS. 33A-33D an endoscopic grasper, designated generally by reference numeral 320, can receive and be powered by the power pack 18 (or power pack 90) of the present disclosure. Grasper 320 has a handle 326 manually pivotable towards stationary handle 324 to effect closing of the jaws 332, an elongated tubular portion 328 extending from the handle housing 322, and a pair of pivotable jaws 332 with grasping surfaces that can include teeth, roughened surfaces, ribs, etc. Closing of the jaws 332 grasps tissue between the grasping surfaces of jaws 332. Either one of the jaws can be movable, i.e., pivotable, or both jaws can be movable (pivotable) toward and away from each other, for movement between closed and open positions. The graspers 320 includes a rotation knob 330 for rotation of the elon- gated portion (shaft) 328 to rotate the jaws 332. Power pack 18 is shown fully loaded (inserted) within the handle hous- ing 322 and cover 323 is shown closed to seal the power pack 18 from the external environment. As in the embodi- ment of FIGS. 1-12, the flag 42 extending from lead screw 36 engages a rod within the handle housing 322 operably connected to a jaw closing mechanism to effect movement of jaws 332 to close the jaws to grasp tissue between the jaws 332. It should be appreciated that the aforedescribed variations of the power packs can also be used with the surgical instruments of FIGS. 32A and 33A.

The power packs 18 and 90 disclosed herein can be used in surgery where the clinician manually clamps the jaws and actuates the motor or motors to provide powered staple firing and/or powered jaw articulation. It is also contemplated that the power packs 18 and 90 can be used with robotic driven surgical staplers wherein clamping, motor actuation and any other functions of the instrument are performed robotically, including remote robotic control.

The staplers disclosed herein, or certain components thereof, can be made of environmental friendly biodegradable materials. For example, the handle can be made of biodegradable material. Such material can include for example corn based lactic acid. The packaging for the surgical staplers and/or the packaging for the power packs and/or the battery packs can also be composed of biodegradable materials to minimize the carbon footprint.

Although the apparatus and methods of the subject disclosure have been described with respect to preferred embodiments, those skilled in the art will readily appreciate that changes and modifications may be made thereto without departing from the spirit and scope of the present disclosure as defined by the appended claims.

Additionally, persons skilled in the art will understand that the elements and features shown or described in connection with one embodiment may be combined with those of another embodiment without departing from the scope of the present invention and will appreciate further features and advantages of the presently disclosed subject matter based on the description provided.

Throughout the present invention, terms such as "approximately," "generally," "substantially," and the like should be understood to allow for variations in any numerical range or concept with which they are associated. For example, it is intended that the use of terms such as "approximately" and "generally" should be understood to encompass variations on the order of 25%, or to allow for manufacturing tolerances and/or deviations in design.

Although terms such as "first," "second," "third," etc., may be used herein to describe various operations, elements, components, regions, and/or sections, these operations, elements, components, regions, and/or sections should not be limited by the use of these terms in that these terms are used to distinguish one operation, element, component, region, or section from another. Thus, unless expressly stated otherwise, a first operation, element, component, region, or section could be termed a second operation, element, component, region, or section without departing from the scope of the present disclosure.

Each and every claim is incorporated as further disclosure into the specification and represents embodiments of the present disclosure. Also, the phrases "at least one of A, B, and C" and "A and/or B and/or C" should each be interpreted to include only A, only B, only C, or any combination of A, B, and C.

What is claimed is:

1. A surgical fastener applier comprising:
a power pack having a motor, a drive mechanism driven by the motor, a first switch and a second switch;
a housing containing a compartment therein, the compartment having an openable cover to provide access to the compartment for removably loading the power pack;
an elongated member extending distally from the housing;

a first jaw and a second jaw adjacent a distal portion of the elongated member, at least the first jaw movable with respect to the second jaw to clamp tissue between the first and second jaws;
a fastener firing mechanism positioned within the housing, the firing mechanism movable by a linear output motion of the drive mechanism of the power pack loaded into the compartment, the firing mechanism movable between a first position and a second position, wherein in the second position, the firing mechanism effects firing of fasteners into the tissue clamped between the first and second jaws, the firing mechanism actuated by the first switch; and
an articulation mechanism movable between a first position and a second position to angle the first and second jaws to an angled position with respect to a longitudinal axis of the elongated member, the articulation mechanism actuated by the second switch;
wherein the first switch cannot be activated if the second switch is activated and the second switch cannot be activated if the first switch is activated.

2. The surgical fastener applier of claim 1, wherein the drive mechanism is engageable with the firing mechanism, and the power pack cannot be removed from the compartment if the drive mechanism is not in a home position.

3. The surgical fastener applier of claim 1, wherein the power pack has a second drive mechanism engageable with the articulation mechanism, and the power pack cannot be removed from the compartment if the articulation mechanism is not in a home position.

4. The surgical fastener applier of claim 1, wherein opening of the jaws disables a firing mode.

5. The surgical fastener applier of claim 1, wherein closing of the jaws disables an articulation mode.

6. The surgical fastener applier of claim 1, wherein the power pack can be removed from the compartment only if first and second engagement members of the power pack are in a home position, the first engagement member engageable with the fastener firing mechanism and the second engagement member engageable with the articulation mechanism.

7. The surgical fastener applier of claim 1, further comprising an interchangeable battery pack removably connectable with the power pack for powering the motor.

8. The surgical fastener applier of claim 1, wherein the cover includes a first seal to seal about the cover in a closed position of the cover to seal the power pack positioned within the compartment.

9. The surgical fastener applier of claim 1, wherein neither the first switch nor the second switch can be activated if the cover is not in a closed position.

10. The surgical fastener applier of claim 1, further comprising a manually actuable handle, the handle movable from a first position to a second position to effect clamping of tissue between the first and second jaws, wherein movement of the handle to the second position enables firing.

11. The surgical fastener applier of claim 10, wherein in the first position of the handle, the first switch is enabled and the second switch to enable articulation is disabled.

12. The surgical fastener applier of claim 10, wherein the power pack has a removable and replaceable battery.

13. A surgical fastener applier comprising:
a power pack having a motor, a first switch and a second switch
a housing containing a compartment therein, the compartment having an openable cover to provide access to the compartment for removably loading the power pack, the power pack loadable to engage a fastener firing mechanism and an articulation mechanism positioned within the housing;

an elongated member extending distally from the housing;

a first jaw and a second jaw adjacent a distal portion of the elongated member, at least the first jaw movable with respect to the second jaw to clamp tissue between the first and second jaws;

the fastener firing mechanism positioned within the housing movable by the motor of the power pack loaded into the compartment, the firing mechanism movable axially between a first position and a second position, wherein in the second position, the firing mechanism effects firing of fasteners into the tissue clamped between the first and second jaws, the firing mechanism actuated by the first switch; and the articulation mechanism movable between a first position and a second position to angle the first and second jaws to an angled position with respect to a longitudinal axis of the elongated member, the articulation mechanism actuated by the second switch;

wherein the first switch is not activatable if the second switch is activatable and the second switch is not activatable if the first switch is activatable.

14. The surgical fastener applier of claim 13, further comprising a manually actuable handle, the handle movable from a first position to a second position to effect clamping tissue of between the first and second jaws, wherein movement of the handle to the second position enables firing.

15. The surgical fastener applier of claim 13, wherein neither the first switch nor the second switch can be activated if the cover is not in a closed position.

16. The surgical fastener applier of claim 15, wherein opening of the jaws disables a firing mode.

17. The surgical fastener applier of claim 16, wherein closing of the jaws disables an articulation mode.

18. The surgical fastener applier of claim 17, further comprising a manually actuable handle, the handle movable from a first position to a second position to effect closure of the jaws to the closed position, wherein movement of the handle to the second position enables firing.

19. The surgical fastener applier of claim 13, wherein the power pack loadable in the compartment has a removable and replaceable battery.

\* \* \* \* \*